United States Patent
Overes et al.

(10) Patent No.: US 8,591,513 B2
(45) Date of Patent: Nov. 26, 2013

(54) ANCHOR-IN-ANCHOR SYSTEM FOR USE IN BONE FIXATION

(75) Inventors: Tom Overes, Langendorf (CH); Robert Frigg, Bettlach (CH); Silas Zurschmiede, Grenchen (CH); Andreas Appenzeller, Biel (CH)

(73) Assignee: DePuy Synthes Products, LLC, Raynham, MA (US)

( * ) Notice: Subject to any disclaimer, the term of this patent is extended or adjusted under 35 U.S.C. 154(b) by 396 days.

(21) Appl. No.: 12/631,293

(22) Filed: Dec. 4, 2009

(65) Prior Publication Data

US 2010/0145397 A1 Jun. 10, 2010

Related U.S. Application Data

(60) Provisional application No. 61/120,138, filed on Dec. 5, 2008.

(51) Int. Cl.
*A61B 17/86* (2006.01)
*A61B 17/58* (2006.01)
*A61F 2/08* (2006.01)
*A61F 2/30* (2006.01)

(52) U.S. Cl.
USPC .......................................... 606/64; 606/319

(58) Field of Classification Search
USPC ......... 606/300, 301, 304, 305, 309, 310, 313, 606/314, 315, 318, 319, 60, 62, 64, 65, 66, 606/67
See application file for complete search history.

(56) References Cited

U.S. PATENT DOCUMENTS

| | | | |
|---|---|---|---|
| 928,997 A | 7/1909 | Muller | |
| 3,474,537 A | 10/1969 | Christensen | |
| 4,338,835 A | 7/1982 | Simons | |
| 4,759,766 A | 7/1988 | Buettner-Janz et al. | |
| 5,038,978 A | 8/1991 | Kolton et al. | |
| 5,140,877 A | 8/1992 | Sloan | |
| 5,207,529 A | 5/1993 | Bailey | |
| 5,425,767 A | 6/1995 | Steininger et al. | |
| 5,443,469 A | 8/1995 | Smith | |
| 5,505,731 A * | 4/1996 | Tornier | 606/261 |
| 5,984,681 A | 11/1999 | Huang | |
| 5,993,463 A | 11/1999 | Truwit | |
| 6,013,078 A | 1/2000 | Lin | |
| 6,113,637 A | 9/2000 | Gill et al. | |

(Continued)

FOREIGN PATENT DOCUMENTS

CN 102292043 A 12/2011
EP 0330328 8/1989

(Continued)

OTHER PUBLICATIONS

Rajasekaran et al., "Translaminar Facetal Screw (Magerl's) Fixation", Neurology India, Dec. 2005, 53(4), 5 pages.

*Primary Examiner* — Anu Ramana
(74) *Attorney, Agent, or Firm* — Woodcock Washburn LLP

(57) ABSTRACT

An anchor-in-anchor fixation system is provided for securing underlying structure, such as bone. The fixation system includes a first bone anchor having a shaft for fixation to underlying bone, and a head that defines an internal bore. A second bone anchor extends through the bore and into underlying bone. A fixation assembly is also provided that includes one or more fixation systems coupled to an auxiliary attachment member configured for long bone fixation, spinal fixation, or fixation of other bones as desired.

27 Claims, 41 Drawing Sheets

(56) References Cited

U.S. PATENT DOCUMENTS

| | | |
|---|---|---|
| 6,168,598 B1 | 1/2001 | Martello |
| 6,467,919 B1 | 10/2002 | Rumsey et al. |
| 6,648,892 B2 | 11/2003 | Martello |
| 6,695,844 B2 | 2/2004 | Bramlet et al. |
| 6,849,093 B2 | 2/2005 | Michelson |
| 7,004,629 B2 | 2/2006 | Shrader |
| 7,094,242 B2 | 8/2006 | Ralph et al. |
| 7,163,540 B2 | 1/2007 | Martello |
| 7,198,643 B2 | 4/2007 | Zubok et al. |
| 7,198,644 B2 | 4/2007 | Levieux |
| 7,326,248 B2 | 2/2008 | Michelson |
| 7,524,326 B2 | 4/2009 | Dierks |
| 7,883,513 B2 | 2/2011 | Ralph et al. |
| 7,887,590 B2 | 2/2011 | Levieux |
| 7,981,114 B2 | 7/2011 | Zander |
| 2003/0135216 A1 | 7/2003 | Sevrain |
| 2003/0171753 A1 | 9/2003 | Collins et al. |
| 2003/0199876 A1 | 10/2003 | Brace et al. |
| 2004/0111161 A1 | 6/2004 | Trieu |
| 2005/0107791 A1 | 5/2005 | Manderson |
| 2006/0052787 A1 | 3/2006 | Re et al. |
| 2006/0064095 A1 | 3/2006 | Senn et al. |
| 2006/0116676 A1 | 6/2006 | Gradel et al. |
| 2006/0189991 A1 | 8/2006 | Bickley |
| 2007/0112354 A1 | 5/2007 | Iwasaki et al. |
| 2007/0191952 A1 | 8/2007 | Bernero |
| 2007/0213729 A1 | 9/2007 | Lindemann et al. |
| 2008/0140130 A1 | 6/2008 | Chan et al. |
| 2008/0221623 A1 | 9/2008 | Gooch |
| 2008/0221624 A1 | 9/2008 | Gooch |
| 2009/0120852 A1 | 5/2009 | Ellsworth et al. |
| 2009/0326545 A1 | 12/2009 | Schaffhausen |
| 2010/0121324 A1 | 5/2010 | Tyber et al. |
| 2010/0121325 A1 | 5/2010 | Tyber et al. |
| 2010/0145397 A1 | 6/2010 | Overes et al. |
| 2010/0160924 A1 | 6/2010 | Soliman |
| 2010/0167240 A1 | 7/2010 | Benzon et al. |
| 2010/0256638 A1 | 10/2010 | Tyber et al. |
| 2010/0256639 A1 | 10/2010 | Tyber et al. |
| 2010/0312280 A1 | 12/2010 | Overes |
| 2010/0324556 A1 | 12/2010 | Tyber et al. |
| 2011/0022066 A1 | 1/2011 | Sevrain |
| 2011/0118739 A1 | 5/2011 | Tyber et al. |
| 2011/0125153 A1 | 5/2011 | Tyber et al. |
| 2011/0137312 A1 | 6/2011 | Mantovani et al. |
| 2011/0160729 A1 | 6/2011 | Overes et al. |
| 2011/0184470 A1 | 7/2011 | Gorek et al. |
| 2011/0213367 A1 | 9/2011 | Tyber et al. |
| 2011/0230884 A1 | 9/2011 | Mantzaris et al. |
| 2011/0230920 A1 | 9/2011 | Gorek et al. |
| 2011/0282398 A1 | 11/2011 | Overes et al. |

FOREIGN PATENT DOCUMENTS

| | | |
|---|---|---|
| EP | 1658816 | 5/2006 |
| EP | 1779794 A1 | 5/2007 |
| JP | 2006-514238 | 4/2006 |
| KR | 10-2011-7015221 | 12/2009 |
| WO | WO 99/47061 A1 | 9/1999 |
| WO | WO 00/38586 A1 | 7/2000 |
| WO | WO 00/69352 | 11/2000 |
| WO | WO 2006/016384 | 2/2006 |
| WO | WO 2006/119092 | 11/2006 |
| WO | WO 2007/048038 A2 | 4/2007 |
| WO | WO 2007/098288 | 8/2007 |
| WO | WO 2009/092907 | 7/2009 |
| WO | WO 2009/149371 | 12/2009 |
| WO | WO 2010/065855 | 6/2010 |
| WO | WO 2011/155931 | 12/2011 |

\* cited by examiner

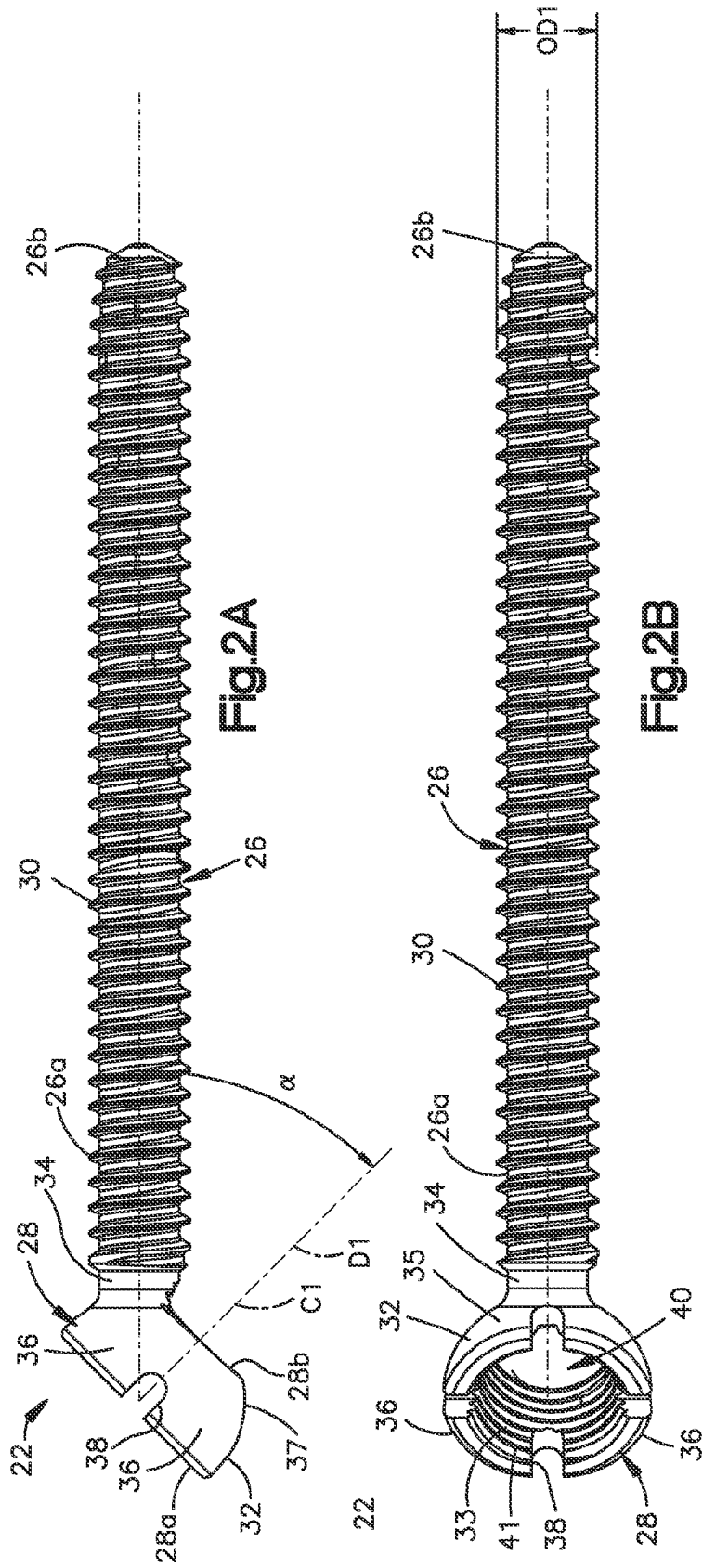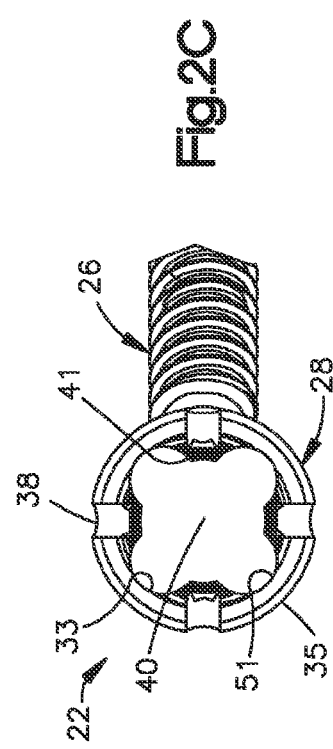
Fig.2A
Fig.2B
Fig.2C

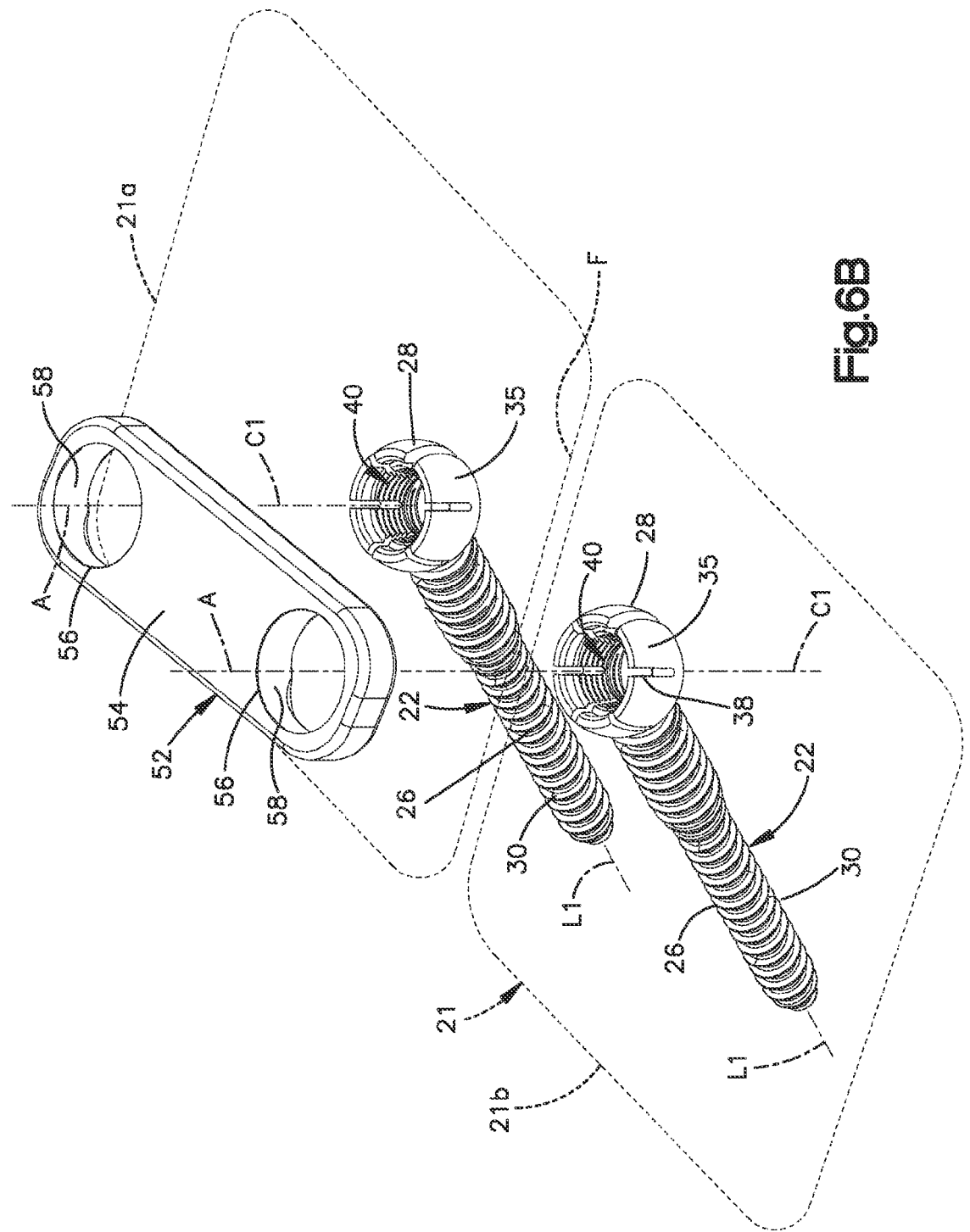

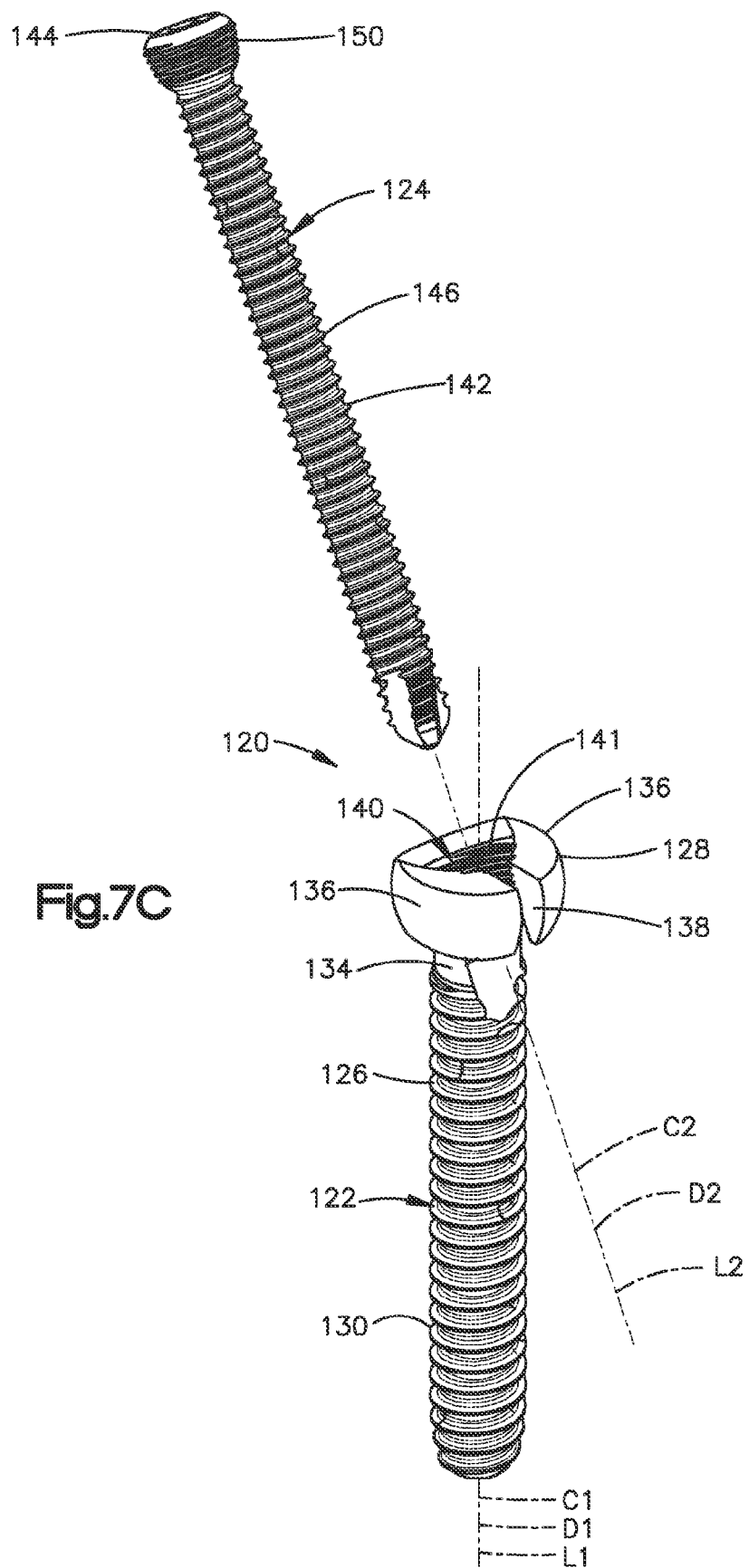

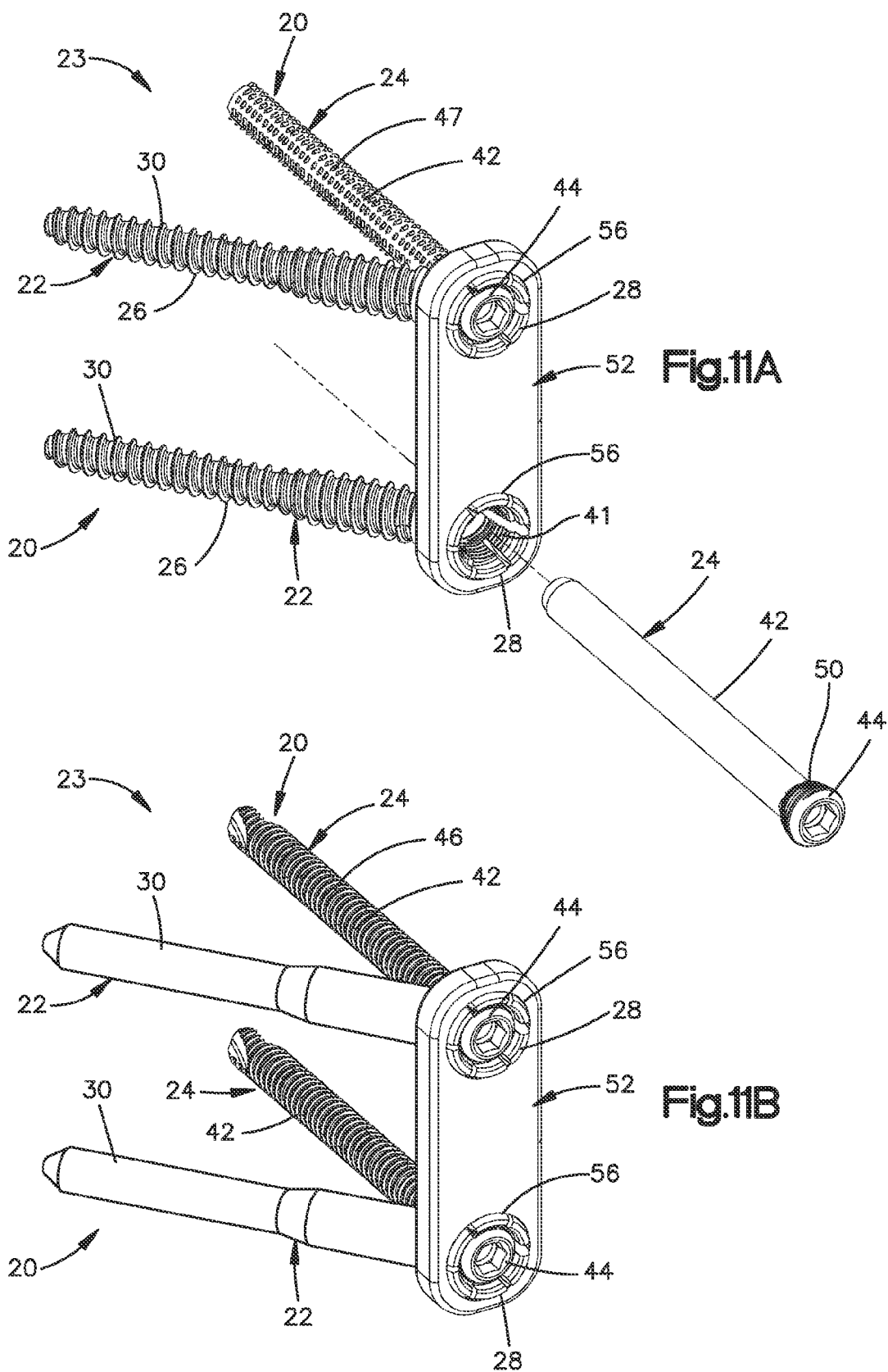

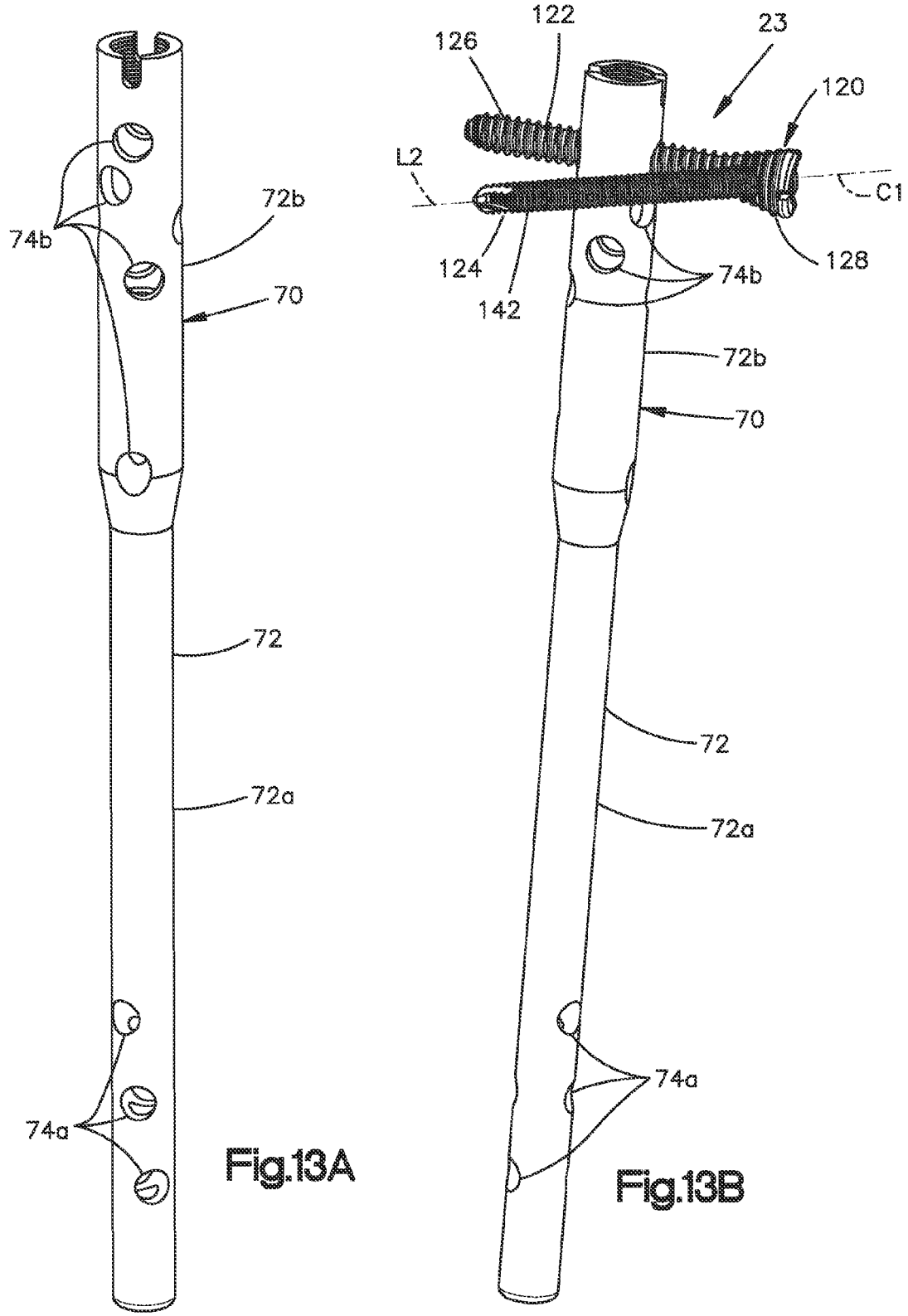

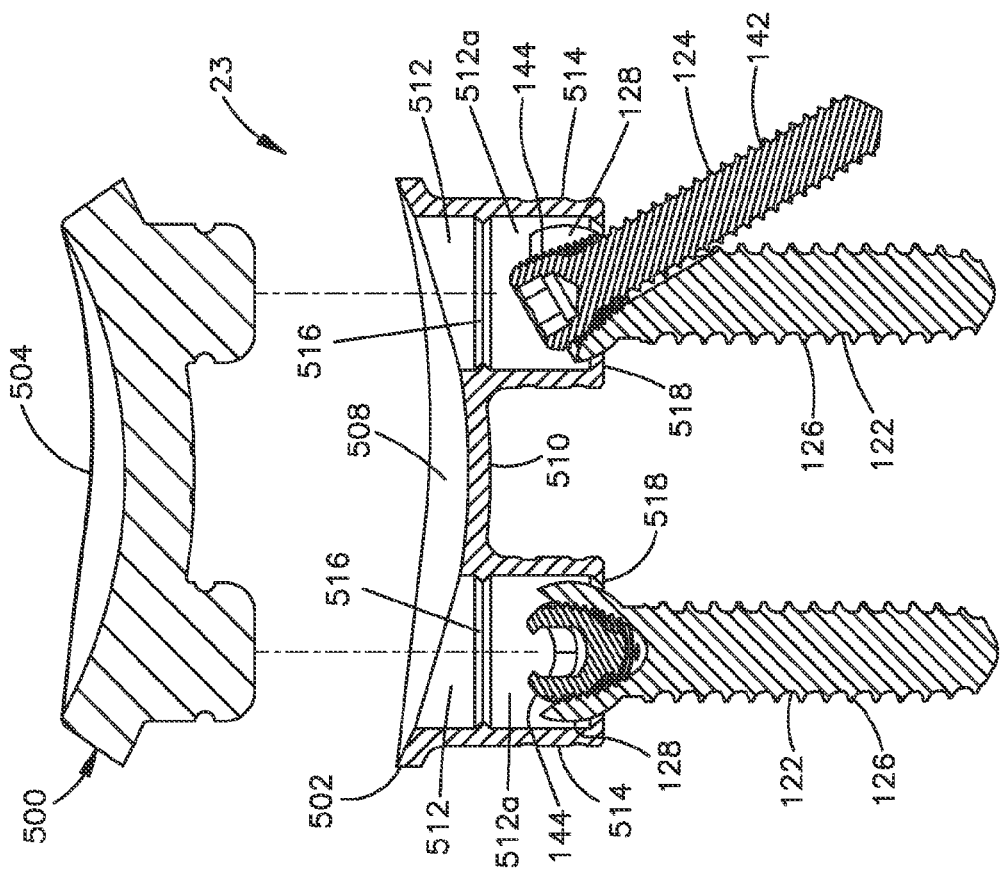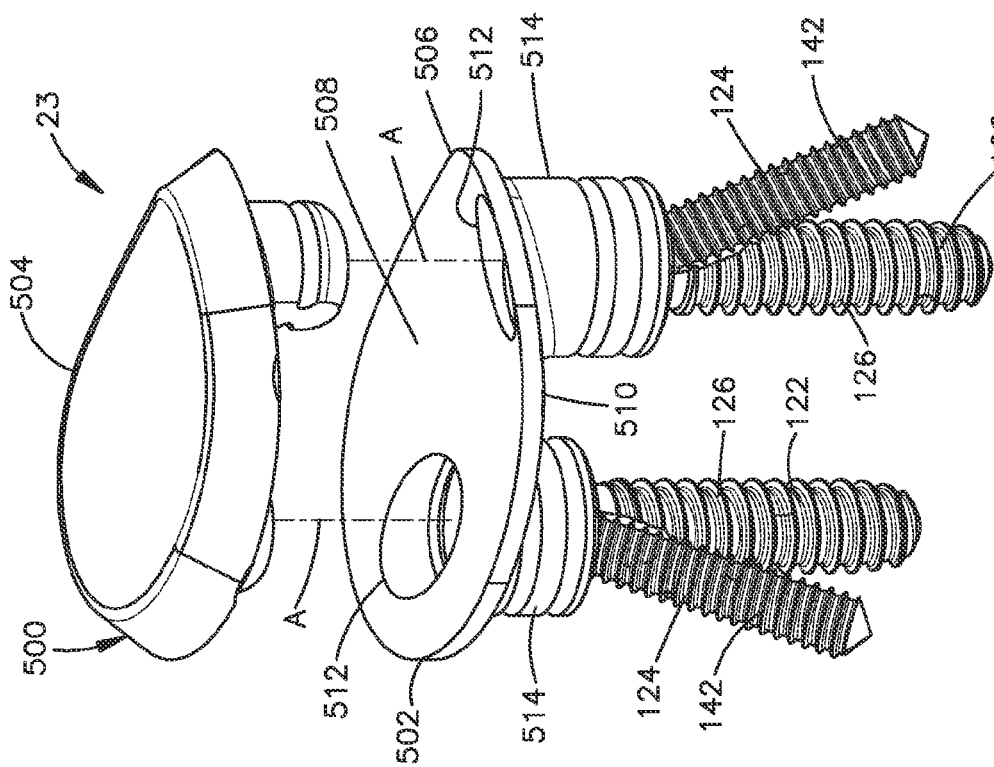

ANCHOR-IN-ANCHOR SYSTEM FOR USE IN BONE FIXATION

CROSS-REFERENCE TO RELATED APPLICATIONS

This claims the benefit of U.S. Patent Application Ser. No. 61/120,138, filed Dec. 5, 2008, the disclosure of which is hereby incorporated by reference as if set forth in its entirety herein.

TECHNICAL FIELD

The present disclosure relates generally to orthopedics, an in particular relates to fixation systems and associated surgical methods and procedures for using same.

BACKGROUND

A variety of fixation devices for the reduction of bone or bone fragments are well known. For instance, external bone fixation devices, or external fixators, are used to reduce fractures of the long bones in the human body. Internal bone fixation devices, such as bone plates, are also commonly used to reduce bone fractures. Spinal fixation devices including intervertebral implants, spinal rods, and the like, are used to replace intervertebral discs, fuse or align adjacent vertebrae, and address other spinal issues.

A large number of fixation devices are attached to underlying bone using bone anchors, which can include screws, pins, nails, and the like. For instance, a typical bone plate includes screw holes that accommodate bone screws which are drilled into underlying bone on opposing sides of a fracture to join bone segments together. A typical cervical spine implant can likewise include screw holes that accommodate screws which are drilled into adjacent vertebral bodies in order to fix the position of the implant. Unfortunately, the attachment of fixation devices to the underlying bone can become compromised if, for instance, the screw becomes dislodged from the bone during normal anatomical function.

What is therefore desirable is an anchor system for use in bone fixation that more reliably fastens a fixation device to underlying bone.

SUMMARY

An anchor-in-anchor fixation system includes a first bone anchor including a first shaft and a first head, the first shaft extending along a first longitudinal shaft axis and configured to attach to underlying structure, and the first head defining a bore extending therethrough along a bore axis, wherein the bore axis and the first longitudinal shaft axis define an acute angle. The anchor-in-anchor fixation system further includes a second bone anchor including a second shaft and a second head, the second shaft extending along a second longitudinal shaft axis and configured to attach to underlying structure, the second bone anchor configured to be inserted into the bore.

BRIEF DESCRIPTION OF THE DRAWINGS

The foregoing summary, as well as the following detailed description of the preferred embodiments of the application, will be better understood when read in conjunction with the appended drawings. For the purposes of illustrating the anchor-in-anchor system, there are shown in the drawings preferred embodiments. It should be understood, however, that the application is not limited to the precise arrangements and instrumentalities illustrated in the drawings, in which:

FIG. 2A is a side elevation view of the first bone anchor of the anchor-in-anchor system illustrated in FIG. 1;

FIG. 2B is another side elevation view of the first bone anchor of the anchor-in-anchor system illustrated in FIG. 1;

FIG. 2C is an end view of the first bone anchor of the anchor-in-anchor system illustrated in FIG. 1 constructed in accordance with an alternative embodiment;

FIG. 2A is;

FIG. 6B is view similar to FIG. 6A, but showing a bone plate configured for attachment to the first anchors;

FIG. 7C is an exploded view of the anchor-in-anchor system illustrated in FIG. 7A;

FIGS. 11A-C are perspective views of anchor-in-anchor fixation assemblies constructed in accordance with alternative embodiments;

FIG. 13A is a side elevation view of an intramedullary rod constructed in accordance with one embodiment;

FIG. 13B is a side elevation view of an anchor-in-anchor fixation assembly including an anchor-in-anchor system attached to the intramedullary rod;

FIG. 20A is an exploded perspective view of an anchor-in-anchor fixation assembly including a shoulder prosthetic;

FIG. 20B is a sectional side elevation view of the anchor-in-anchor fixation assembly illustrated in FIG. 20A.

DETAILED DESCRIPTION

Figure 1:
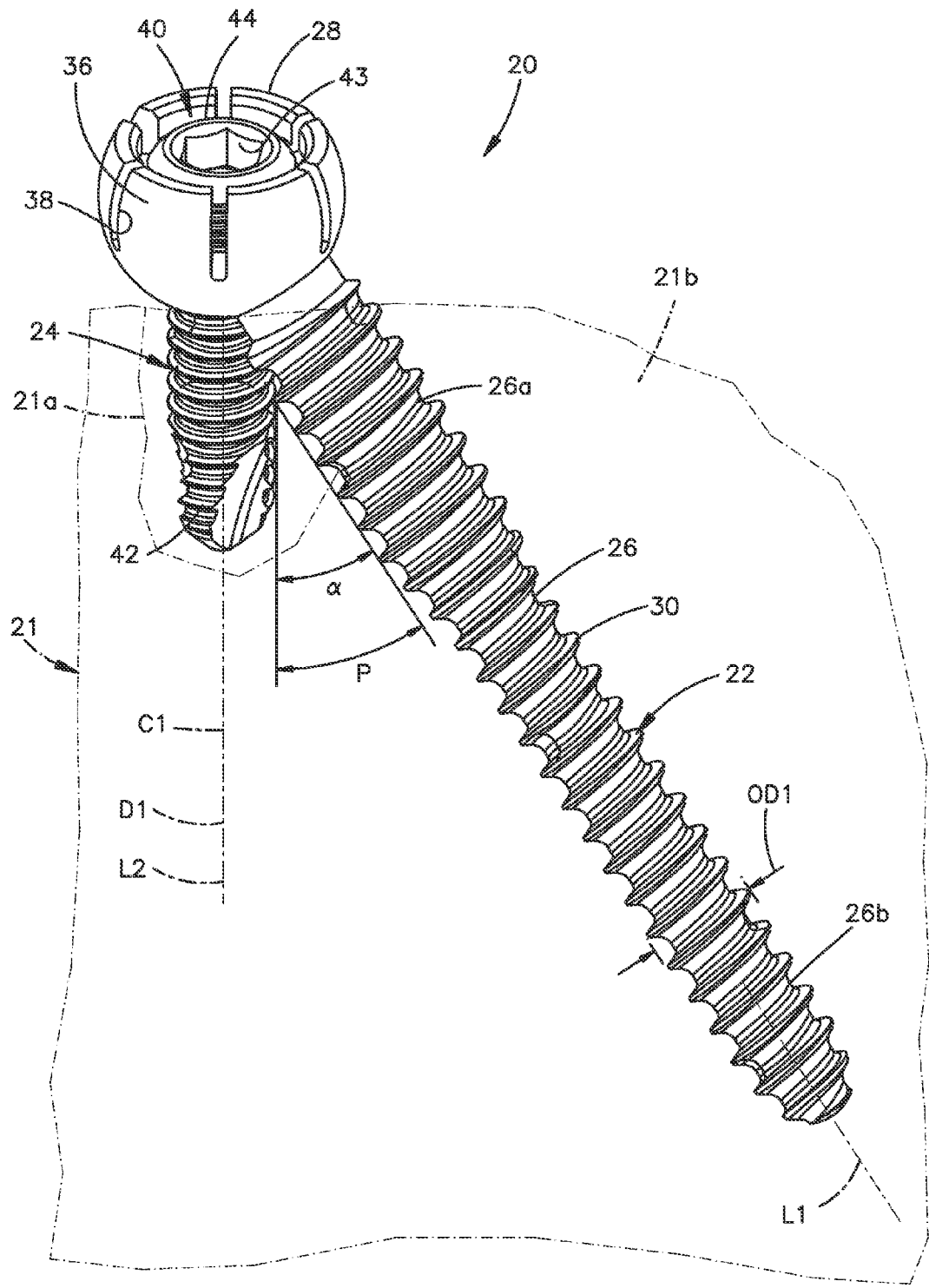
FIG. 1 is a perspective view of an anchor-in-anchor system constructed in accordance with one embodiment and including a first bone anchor receiving and attached to a second bone anchor.

Certain terminology is used in the following description for convenience only and is not limiting. The words "right," "left," "top," and "bottom" designate in the drawings to which reference is made. The words "inwardly" and "outwardly" refer to directions toward and away from, respectively, the geometric center of the device and designated parts thereof. The words "anterior," "posterior," "superior," "inferior," and related words and/or phrases designate preferred positions and orientations in the human body to which reference is made and are not meant to be limiting. The terminology includes the above-listed words, derivatives thereof and words of similar import.

With initial reference to FIG. 1, an anchor-in-anchor fixation system 20 is illustrated as attached to an underlying structure or bone 21. The fixation system 20 is illustrated as a bone fixation system in accordance with one example embodiment that includes a first or primary bone fixation element or bone anchor 22 and a second or auxiliary bone fixation element or bone anchor 24 that is received by the first bone anchor 22. As will become appreciated from the description below, the bone fixation system 20 can be used to securely fasten auxiliary fixation devices such as external fixators, internal bone fixation devices, spinal fixation devices, and the like, to underlying bone. Unless otherwise indicated, the bone fixation system 20 and its components can be manufactured from any suitable biocompatible material known in the art including but not limited to titanium, titanium alloy such as TAN, stainless steel, reinforced plastics, allograft bone, and the like, unless otherwise indicated.

Referring also to FIGS. 2A-C, the first bone anchor 22 includes a shaft 26 that extends longitudinally along a central longitudinal axis L1. The bone anchor 22 includes a shaft 26 that defines longitudinally opposing proximal, or upper, and distal, or lower, ends 26a and 26b, respectively, and a head 28 coupled to the proximal end 26a. Helical threads 30 extend radially out from the shaft 26 at locations at and between the proximal and distal ends 26a-b that are configured to engage underlying bone. Thus, a substantial entirety of the shaft 26 can be threaded. As illustrated in FIG. 1, the threads 30 define an outer diameter OD1 that increases in a direction from the distal end 26b toward the proximal end 26a. Accordingly, the threads 30 disposed at the proximal end 26a define an outer diameter that is greater than the outer diameter of the threads 30 disposed at the distal end 26b. Alternatively, as illustrated in FIGS. 2A-B, the outer diameter OD1 of the threads 30 is constant across the proximal and distal ends 26a-b. It should thus be appreciated that the first bone anchor 22 can provide as a locking screw as illustrated, though it should be appreciated that the first bone anchor can alternatively be provided as a compression screw, a nail, rivet, or pin whose shaft is smooth or ribbed, as desired.

The head 28 includes an annular body 32 that defines a radially inner surface 33, an opposing radially outer surface 35, a proximal, or upper, end 28a and a distal, or lower, end 28b. The annular body 32 can define the shape of a segment of a sphere as illustrated, having a diameter or cross-sectional dimension that is greater at a location between the proximal and distal ends 28a-b than at either of the proximal and distal ends 28a-b. Accordingly, the radially outer surface 35 can be spherical or otherwise convex. Of course, the head 28 can assume any other suitable alternative shape as desired.

The distal end 28b of the head 28 is coupled to the proximal end 26a of the shaft 26, either directly or indirectly via an unthreaded neck 34 that is coupled between the proximal end 26a of the shaft 26 and the distal end 28b of the head 28. The annular body 32 can include a base 37 at the distal end 28b that extends continuously in a circumferential direction about the head 28. The annular body 32 further includes a plurality of circumferentially spaced retention tabs 36 that extend up from the distal end 28b. Thus, the terminal ends of the retention tabs 36 are disposed at the proximal end 28a of the head 28. The retention tabs 36 are configured such that circumferentially adjacent tabs 36 are separated by a slot 38 that extends distally into the proximal end 28a of the head 28 in a direction toward, but not through, the base 37.

The head 28 further defines a bore 40 extending centrally through the annular body 32 along a central bore axis C1. The central axis C1 extends in a direction angularly offset with respect to the longitudinal axis L1. The shaft 26 is coupled to the base 37, and extends radially outward and down from the radially outer surface 35 of the base 37 such that the shaft 26 does not interfere with the bore 40. The head 28 includes a plurality of helical threads 41 in the bore 40 that extend radially inward from the radially inner surface 33 of the annular body 32, including the tabs 36 and the base portion 37. In the illustrated embodiment, the central axis C1 of the bore 40 intersects with the longitudinal axis L1 of the shaft 26 so as to define an acute angle α. The angle α is illustrated as being acute. Thus, in accordance with one embodiment, the angle is between 0° and 90°, for instance between 20° and 60°, for instance between 20° and 40°.

In the illustrated embodiment, the central axis C1 is normal with respect to the proximal and distal ends 28a-b, though it should be appreciated that the proximal and distal ends 28a-b could be configured such that the central axis C1 defines a non-perpendicular angle with respect to one or both of the proximal and distal ends 28a-b. Therefore, with continuing reference to FIGS. 1-2B, the head 28 of the first bone anchor 22 defines a central head axis D1 defined by the proximal and distal ends 28a-b. In particular, central axis D1 extends in a direction normal with respect to the proximal and distal ends 28a-b. Because the central axis C1 of the bore 40 extends parallel to the direction extending between the proximal and distal ends 28a-b in the illustrated embodiment, the axes C1 and D1 are longitudinally aligned and substantially coincident, and thus define the same angle α with respect to the longitudinal axis L1 of the shaft 26. Otherwise stated, the orientation of the head 28 is angularly offset with respect to the shaft 26 equal to the angular offset of the bore 40 with respect to the shaft 26, though it should be appreciated that the axes C1 and D1 may alternatively be angularly offset as desired.

While the inner surface 33 can include threads 41 extending circumferentially continuously within the bore 40 as illustrated in FIGS. 2A-B, it is appreciated that the head 28 can be constructed in accordance with an alternative embodiment that allows the second bone anchor 24 to attached inside the head 28 at variable angles with respect to the central bore axis C1, head axis D1, and longitudinal axis L1. In particular, as illustrated in FIG. 2C, the head 28 can include a plurality of recesses 51 extending into the inner surface 33. The recesses 51 can define a portion of a cylinder, and thus configured to receive a corresponding portion of the second bone anchor 24. The threads 41 extend between adjacent recesses 51. While four recesses 51 are shown as being circumferentially equidistantly spaced at 90° with respect to each other, it should be appreciated that the head 28 can include any number of recesses 51 so as to allow the second bone anchor 24 to be inserted into the head 28 at any desired angle, as will be described below with reference to FIG. 4D.

Figure 3:
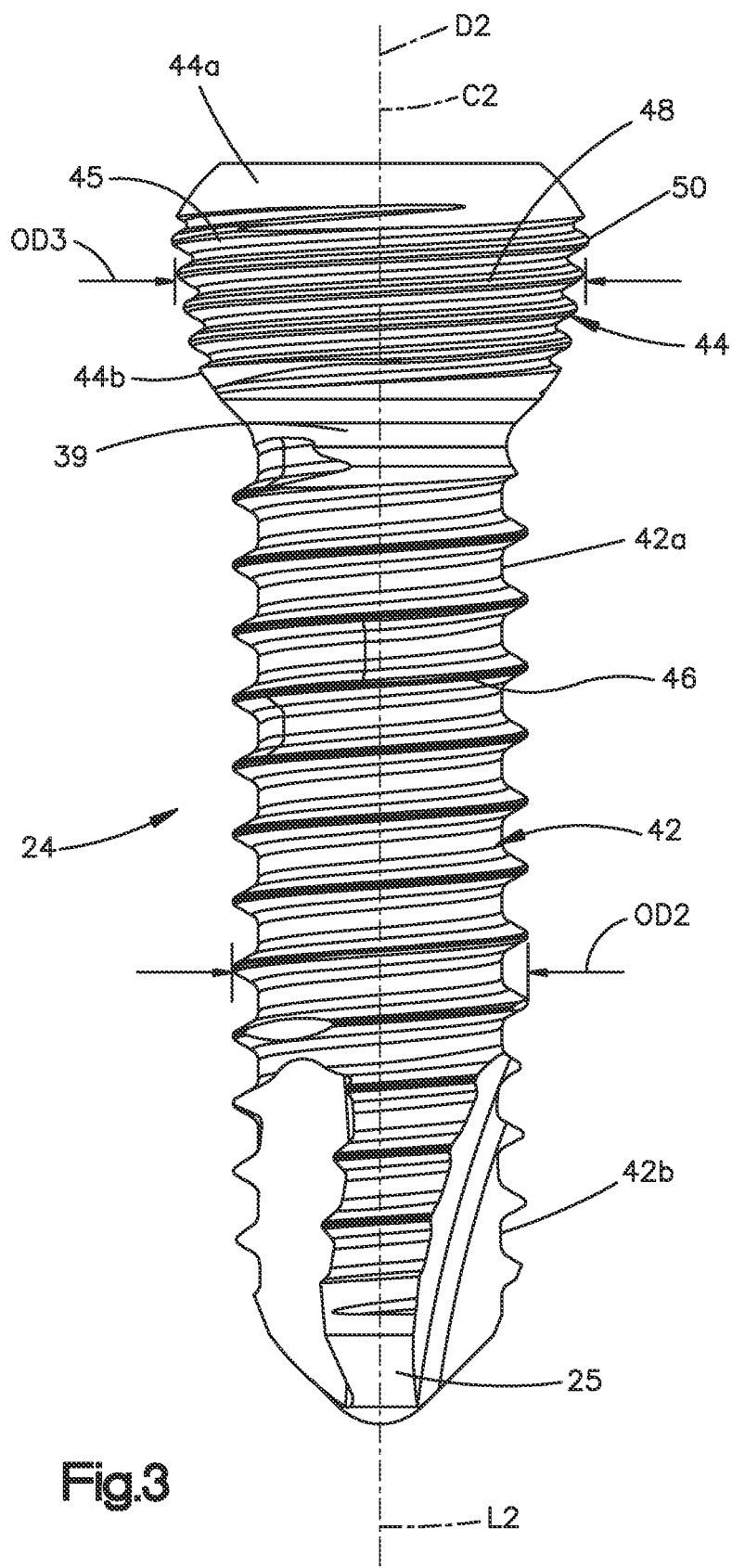
FIG. 3 is a side elevation view of the second bone anchor of the anchor-in-anchor system illustrated in FIG. 1.

Referring now to FIGS. 1 and 3, the second bone anchor 24 includes a shaft 42 that extends longitudinally along a central longitudinal axis L2. The shaft 42 can be longer, shorter, or substantially equal to the longitudinal length of the shaft 26. The shaft 42 defines longitudinally opposing proximal, or upper, and distal, or lower, ends 42a and 42b, respectively. The bone anchor 24 includes a head 44 coupled to the proximal end 42a of the shaft 42. Helical threads 46 extend radially out from the shaft 42 at locations at and between the proximal and distal ends 42a-b that are configured to engage underlying bone. Thus, the substantial entirety of the shaft 42 can be threaded. The threads 46 define an outer diameter OD2 that is constant across the proximal and distal ends 42a-b as illustrated, though the threads 46 can alternatively increases in a direction from the distal end 42b toward the proximal end 42a as described above with respect to the shaft of the bone anchor 22. The outer diameter OD2 can be greater than, less than, or substantially equal to the outer diameter OD1. The threads 46 can define the same pitch or a different pitch with respect to the threads 30 of the first bone anchor 22.

The head 44 includes an annular body 48 that defines a radially inner surface 43 an opposing radially outer surface 45, a proximal, or upper, end 44a and a distal, or lower, end 44b. The outer surface 45 extends concentrically about an axis C2, and can define the shape of a frustum as illustrated having an outer diameter OD3 or cross-sectional dimension that increases in a direction from the distal end 44b of the head 44 toward the proximal end 44a. Alternatively, the head can assume any suitable alternative shape as desired, such as a segment of a sphere as illustrated, having a diameter or cross-sectional dimension that is greater at a location between the proximal and distal ends 44a-b than at either of the proximal and distal ends 44a-b. In the illustrated embodiment, the central axis C2 is parallel and coincident or aligned with the longitudinal axis L2 of the shaft 42, though it should be appreciated that the central axis C2 could be angularly offset from the longitudinal axis L2 if desired.

The distal end 44b of the head 44 is coupled to the proximal end 42a of the shaft 42, either directly as illustrated, or indirectly via an unthreaded neck 39 of the type described above with respect to the first bone anchor 22. The head 44 includes helical threads 50 that extend radially out from the outer surface 45 of the annular body 48. It should thus be appreciated that the second bone anchor 24 can provide as a locking screw as illustrated, though it should be appreciated that the second bone anchor can alternatively be provided as a compression screw, a nail, rivet, or pin whose shaft is smooth or ribbed, as desired.

The head 44 further defines a central axis D2 defined by the proximal and distal ends 44a-b. In particular, the central axis D2 extends in a direction normal with respect to the proximal and distal ends 44a-b. Because the central axis C2 head 44 extends parallel to the direction extending between the proximal and distal ends 44a-b in the illustrated embodiment, the axes C2 and D2 are coincident or aligned, and thus extend parallel and coincident or aligned with the longitudinal L2 in the illustrated embodiment. Of course, it should be appreciated that the proximal and distal ends 44a-b could be geometrically configured such that the axes C2 and D2 are angularly offset from each other.

The threads 50 define an outer diameter OD3 that increases in a direction from the distal end 44b of the head 44 to the proximal end 44a of the head 44. Thus, the outer diameter of the threads 50 is greater at the proximal end 44a than at the distal end 44. The inner diameter of the threads 41 of the bore 40 can define an inner diameter that increases in a direction from the distal end 44b toward the proximal end 44a, such that the threads 50 and 41 are configured to mate. It should be appreciated, of course, that the outer diameter of the threads 50 and 41 could be constant across the corresponding proximal and distal ends.

The assembly of the bone fixation system will now be described with respect to FIGS. 1 and 4A-C. In particular, the bore 40 of the first bone anchor 22 is configured to receive the second bone anchor 24, such that the first and second bone anchors 22 and 24 are fastened together. Thus, during use, the surgeon forms an incision to access a targeted area of the underlying bone 21. Next, the first bone anchor 22 is driven, for instance screwed, into the underlying bone 21 such that the threads 30 engage and attach the bone anchor 22 to a select one of the underlying bone segments 21a-b. Either or both of the bone anchors 22 and 24 can be self-tapping, and thus include cutting flutes 25, or a bore can be pre-drilled into the bone 21 prior to insertion of the shaft 26 into the bone 21. The first bone anchor 22 is inserted into the underlying segment such as a bone segment 21a to a sufficient depth, and is rotated until the axis C1 of the bore 40 is aligned with a desired fixation location of a second underlying segment such as a second bone segment 21b. Once the first bone anchor 22 has been fastened to the underlying bone, the second bone anchor 24 is inserted into the underlying bone 21 through the head 28 of the first bone anchor 22. The second bone anchor 24 can be inserted into the underlying bone 21 through the same incision that received the first bone anchor 22, or through a second incision as desired.

In one embodiment, the first bone anchor 22 is fastened to a first fractured segment 21a of the underlying bone 21, which can be a long bone, such as a femur, humorous, tibia, radius, ulna, or any other bone as desired, and the second bone anchor 24 is fastened to second fractured segment 21b of the underlying bone 21. For instance, the first bone anchor 22 can be fastened to the shaft or intramedullary portion of a patient's femur, while the second bone anchor 24 can be fastened to the head portion of the patient's femur. In this regard, the anchor-in-anchor bone fixation system 20 can be used to fix a femoral fracture, though it should be understood that the fixation system 20 and surgical methods of using the fixation system is equally applicable in other surgical procedures in which a surgeon desires to couple one or more bones or bone fragments.

Figure 4A:
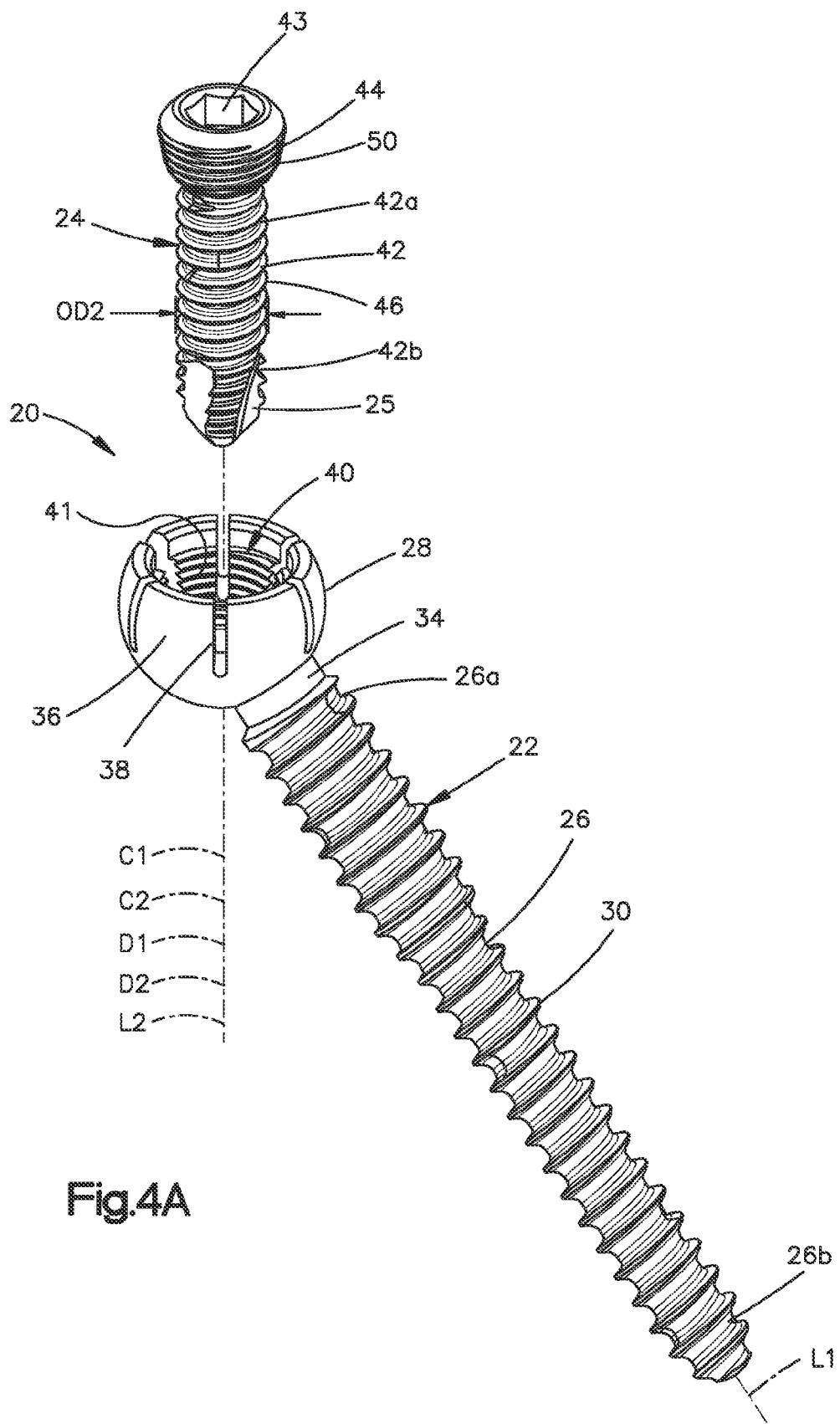
FIG. 4A is an exploded view showing the second bone anchor aligned for insertion in the first bone anchor.
Figure 4B:
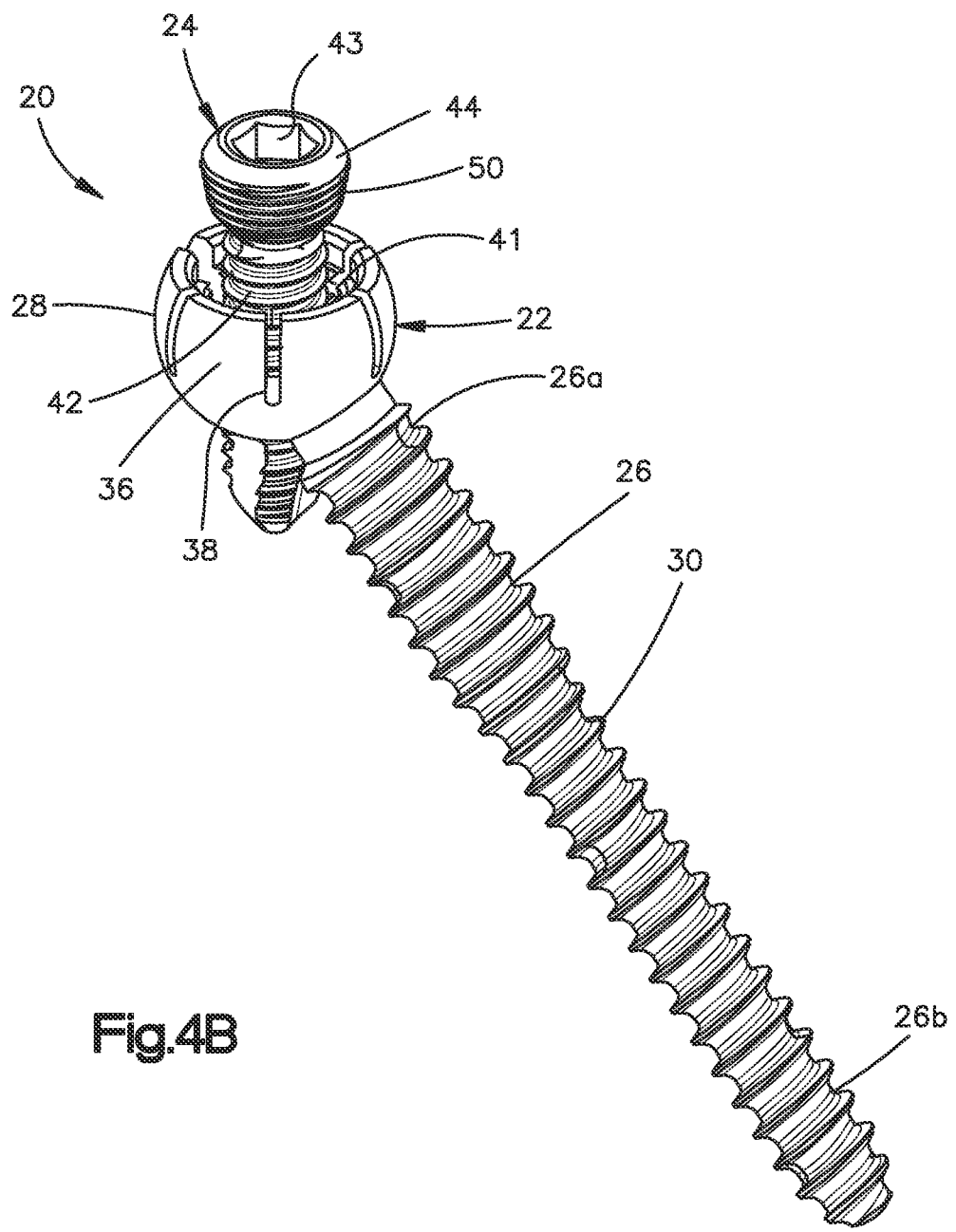
FIG. 4B is a view similar to FIG. 4A but showing the second bone anchor partially inserted in the first bone anchor.
Figure 4C:
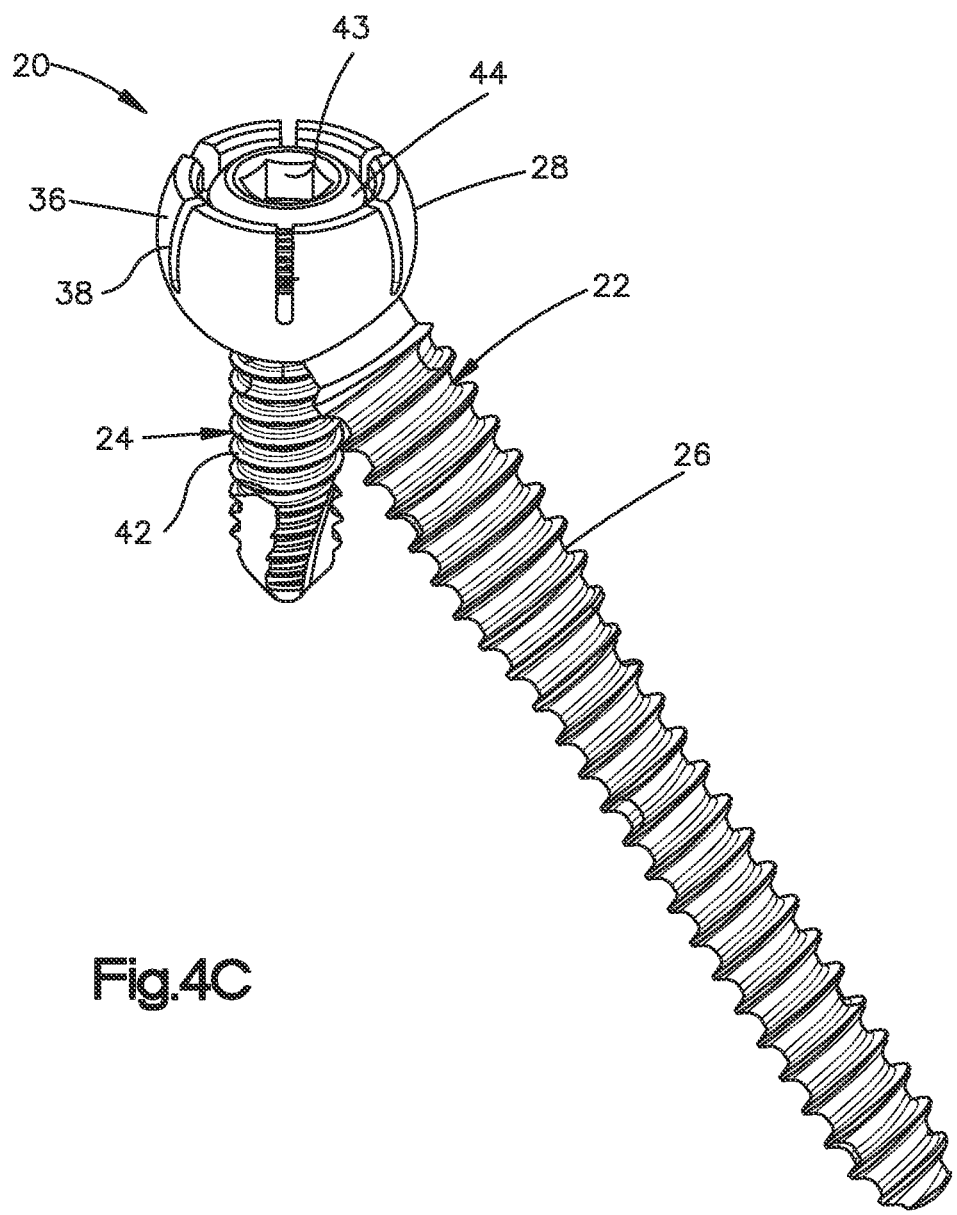
FIG. 4C is a view similar to FIG. 4B but showing the second bone anchor inserted and attached to the first bone anchor.

With continuing reference to FIGS. 1 and 4A-C, the outer diameter OD2 of the threads 46 is less than the inner diameter of the bore 40 extending through the head 28 of the first bone anchor 22, such that the shaft 42 can be driven linearly down through the bore 40 as shown in FIG. 4B. Alternatively, the outer diameter OD2 can be sized such that the threads 46 can engage the threads 41 of the head 28 as the bone anchor 24 is rotated therein. As described above, the outer threads 50 of the head 44 are configured to mate with the inner threads 41 of the head 28. Accordingly, the shaft 42 of the first bone anchor 22 can be driven through the bore 40 until either the distal end 42b of the shaft 42 engages the bone 21, or the threads 41 and 50 engage.

The bone anchors 22 and 24 can then be rotated with respect to each other to longitudinally advance the shaft 42 into the bone 21, and to longitudinally advance the head 44 inside the head 28 of the first bone anchor 22 at the same rate as the advancement of the shaft 42 into the bone, such that the first and second bone anchors 22 and 24 are locked together. Thus, the second bone anchor 24 can attach to the first bone anchor 22 without compressing the first bone anchor 22 against the underlying bone 21. Alternatively, the head 44 can be devoid of threads, and the inner surface 33 of the head 28 can be devoid of threads, such that the engagement of the head 44 against the head 28 causes the first bone anchor 22 to compress against the underlying bone 22. The radially inner surface 43 of the head 44 can define a hexagonal or any alternatively shaped structure that can be engaged by a screw driving instrument to rotate the head 44 inside the head 28. Alternatively or additionally, a tool can be inserted into the slots 38 disposed between the retention tabs 36 to prevent the first bone anchor 22 from rotating along with the second bone anchor 24.

Generally, the second bone anchor 24 engages the underlying bone 21 prior to engagement of the threads 41 and 50. As the distal end 44b of the head 44 of the second bone anchor 24 engages the proximal end 28a of the head 28 of the first bone anchor 22, the retention tabs 36 can flex radially outward. Once the first and second bone anchors 22 and 24 have been fully mated, the head 44 of the second bone anchor 24 is nested inside the head 28 of the first bone anchor 22, and the proximal end 44a of the head 44 is substantially flush with the proximal end 28a of the head 28. The shaft 26 of the first bone anchor 22 extends oblique with respect to the underlying bone 21, while the shaft 42 of the second bone anchor extends substantially normal with respect to the underlying bone 21, though it should be appreciated that both shafts could alternatively extend in a direction oblique to the underlying bone.

The retention tabs 36 have particular utility when locking the head 28 in an aperture of an auxiliary bone fixation device, such as a bone plate, an intramedullary nail or screw, an intervertebral implant, a pedicle screw, or the like as will be described in more detail below. It should be appreciated that the head 28 can alternatively be circumferentially continuous at and between the proximal and distal ends 28a-b of the head.

In this manner, when locked inside one another, the bone anchors form a stable triangular load bearing plane P defined by the longitudinal axes L1 and L2, and a direction extending between the shafts 24 and 42 (for instance, between the terminal ends of the shafts 24 and 42). The triangular load bearing plane P is better able to withstand higher forces and prevent subsidence or migration of the bone anchor within the bone. That is, because the bone anchors 22 and 24 are angled with respect to each other, each bone anchor resists migration within the bone due, for instance, to longitudinal forces applied to the other bone anchor that would tend to pull the bone anchor out of the underlying bone 21. In this manner, the anchor-in-anchor bone fixation system 20 enables a smaller auxiliary fixation device such as, for example, a plate, an intramedullary nail or screw, an intervertebral implant, or the like, to be used while enabling the surgeon to insert a larger number of bone anchors, such as bone anchors 22 and 24, to withstand anticipated loads.

Figure 4D:
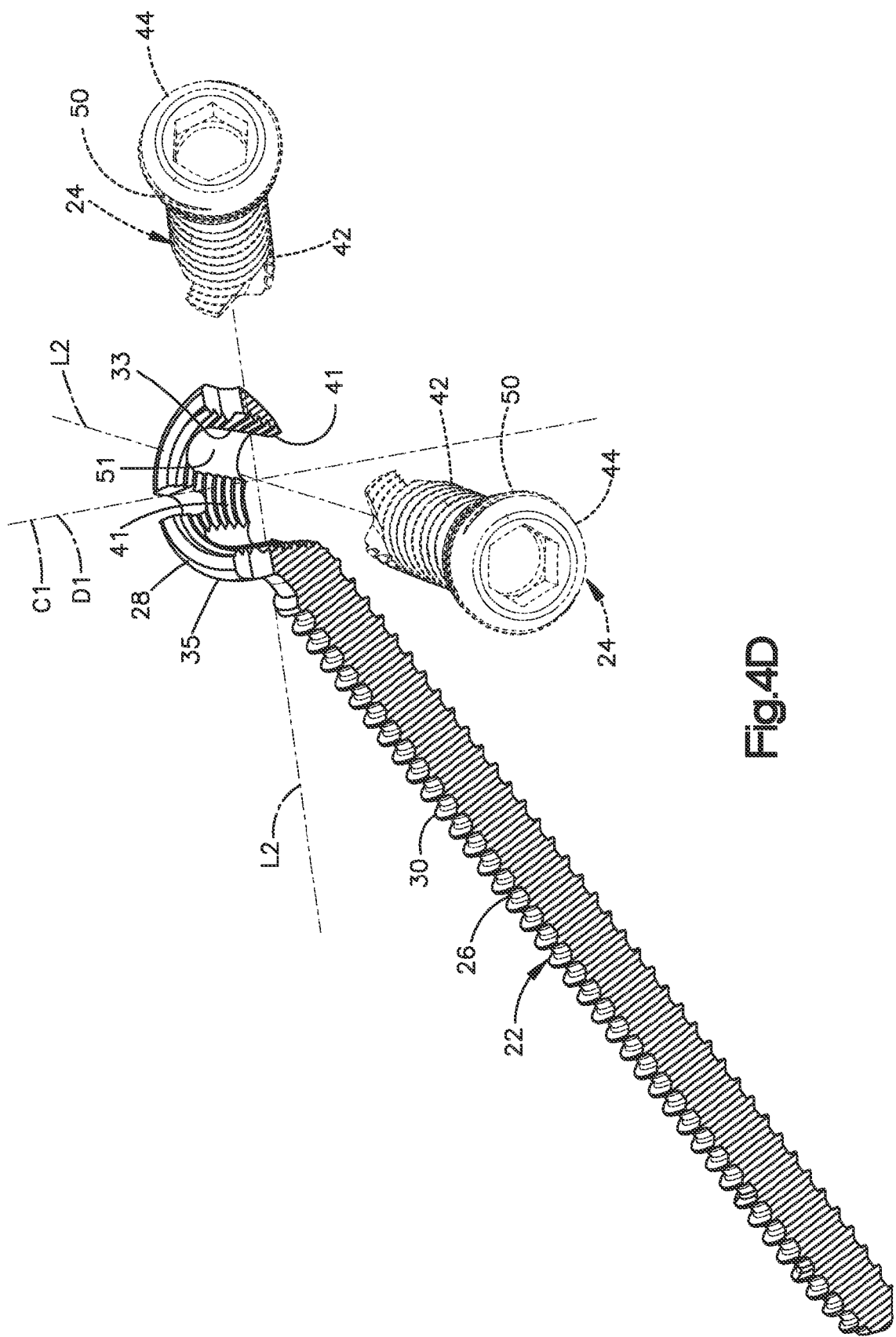
FIG. 4D is a perspective view of the first bone anchor illustrated in FIG. 2C with a portion cut away, and further showing a second bone anchor insertable into the first bone anchor at variable angles.
Figure 5:
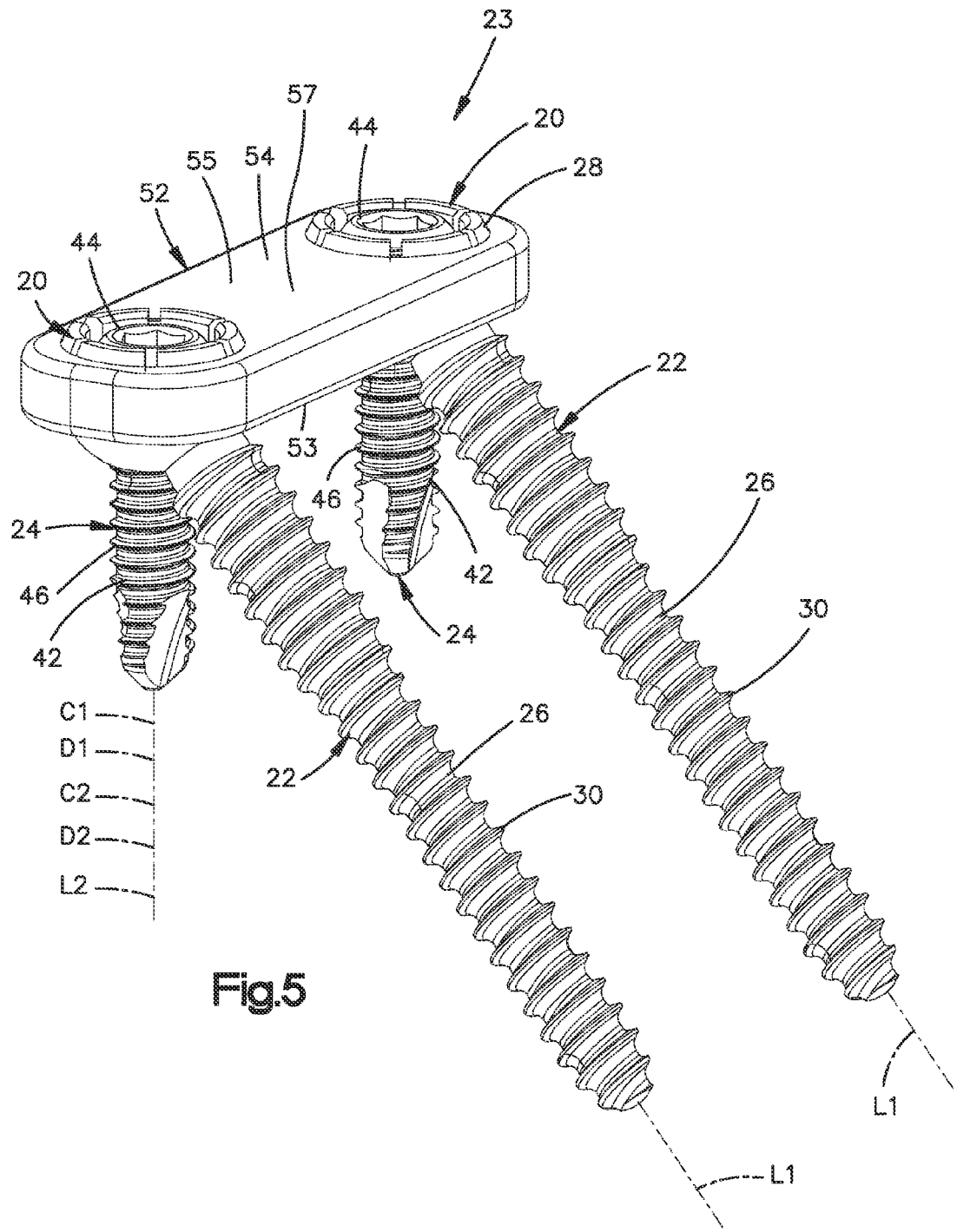
FIG. 5 is a perspective view of an anchor-in-anchor fixation assembly including a pair of an anchor-in-anchor fixation systems as illustrated in FIG. 1 attached to an auxiliary fixation device provided as a bone plate.

Referring now to FIG. 4D, the head 28 illustrated in FIG. 2C allows the second bone anchor to attach to the head 28 such that the second longitudinal axis L2 defines variable angles with respect to the central bore axis C1, the head axis D1, and the first longitudinal axis L1. In particular, the second bone anchor 24 can be inserted into the bore 40 such that a first portion of the bone anchor 24 is disposed in one of the recesses, and a second portion of the bone anchor that is distal with respect to the first portion is disposed in another one of the a recesses that is opposed to the recess through which the first portion of the bone anchor 24 is disposed. In the illustrated embodiment, the head 44 is inserted into the bore 40 such that at a portion the proximal end of the head 44 is disposed in one of the recesses such that the head axis D2, and thus the longitudinal axis L2, is angularly offset with respect to the central bore axis C1 in a direction toward another one of the a recesses that is opposed to the recess through which the proximal end of the head 44 is disposed. It should be appreciated that the head 44 can be disposed in any one of the recesses 51 as desired, such that any one or all of the central axis C2, the head axis D2, and the longitudinal axis L2 defines an angle, for instance between 0° and 30°, with respect to any one or both of the central axis C1 and the head axis D1.

The thread pitch of the threads 50 can vary from narrow-to-wide-to-narrow as measured along the central axis of the anchor 24 from one end (e.g., the proximal end) to the other end (e.g., the distal end). This thread profile allows the anchor 24 to engage the bore 40 at a selectable angle within a range of angles while maintaining the same degree of contact with the inner threads 41 regardless of the angle chosen, as described in U.S. patent application Ser. No. 11/971,358, filed Jan. 9, 2009, the disclosure of which is hereby incorporated by reference as if set forth it its entirety herein. That is, the angle of the anchor 24 with respect to the central bore axis C1 within the permissible range of angles does not affect the engagement of the threads 50 with the threads 41.

As will be described below, anchor-in-anchor bone fixation systems can be used in long bone applications, shoulder prosthesis, spinal applications, and can be used for stand-alone fixation whereby the bone anchors directly affix underlying bone segments, or can include one or more auxiliary fixation devices such as bone plates, intramedullary nails or screws, intervertebral implants or other spinal implants such as pedicle screws, and shoulder prosthesis. The anchor-in-anchor fixation systems of the type described herein can thus be used in long bone fracture fixation to fix two or more bones or segments, can be used in the spine in a facet or laminoplasty fixation procedure, and shoulder prosthesis. It should be noted that it is not intended for any of the anchor-in-anchor systems as described herein to be limited to the particularly identified procedures and/or applications unless specifically noted.

For instance, referring now to FIGS. 5 and 6A-F, one or more anchor-in-anchor bone fixation systems 20 can be used in combination with an auxiliary fixation device such as a bone plate 52 so as to define an anchor-in-anchor fixation assembly 23 configured to fix of one or more long bones or bone fragments in a patient's body. Thus, the fixation assembly 23 includes at least one, such as a plurality of anchor-in-anchor bone fixation systems, configured to be coupled to an auxiliary fixation device. While various embodiments of the fixation assembly 23 are illustrated with respect to one or both of the fixation systems 20 and 120, it should be appreciated that either or both fixation systems 20 or 120 could be coupled to the auxiliary fixation device unless otherwise indicated. The fixation assembly and its components can be manufactured from any suitable biocompatible material known in the art including but not limited to titanium, titanium alloy such as TAN, stainless steel, reinforced plastics, allograft bone, and the like, unless otherwise indicated.

The bone plate 52 can be configured as desired, and includes an elongate planar plate body 54 defining an inner bone-facing surface 53 and an opposing outer surface 55. One or more, such as a plurality, of bone fixation apertures 56 (a pair of apertures 56 as illustrated) extends through the plate body 54 along a central axis A, which extends perpendicular to the inner and outer surfaces 53 and 55 of the plate body 54. The plate body 54 thus defines a central plate portion 57 that is disposed between the apertures 56 and configured to overlay a fracture F that separates the bone segments 21a-b. The plate body 54 can be planar as illustrated, though it could be curved or shaped as desired so as to conform partially or fully to the underlying bone, depending on the type of bone fixation being performed.

The apertures 56 present a spherical or otherwise convex inner surface 58 that matches the contour of the outer radial surface 35 of the head 28. A plurality of first bone anchors 22 is installed in the bone plate 52 such that each head 28 is disposed in a corresponding aperture 56, the central axis C1 of the bore 40 coincides with the central axis A of the corresponding aperture 56, and the longitudinal axis L1 of the shaft 26 extends down from the plate 52 in a direction that defines the angle α with respect to the axis A of the aperture 56. The second bone anchor 24 is fastened to the first bone anchor 22 in the manner described above, such that the shaft 42 extends down from the plate 52 along the axis A.

The method of attaching the bone plate 52 to underlying bone segments 21a-b will now be described with reference to FIGS. 6A-E. In particular, a first bone anchor 22 is inserted into the bone segment 21a, and the second bone anchor 24 is inserted into the bone segment 21b. The bone segments 21a-b can be disposed on opposing sides of a fracture F. The first bone anchors 22 can be inserted into the bone segments 21a-b at an angle such that the head 28 is configured for insertion into the aperture 56 of the bone plate 52. In accordance with one embodiment, the bone anchor 22 is rotated in one of the underlying bone segments 21a-b until the central axis C1 of the bore 40 is oriented substantially vertically, or substantially normal to the surface of the bone segment to which the second bone anchor is to be inserted. The second bone anchor 24 can be inserted into the same bone segment as the first bone anchor 22, or a different bone segment that is separated from the bone segment of the first bone anchor 22 by a fracture. The threads 30 can be self-tapping, such that the bone anchors 22 are directly inserted into the underlying bone segments 21a-b. Alternatively, a guide bore can be drilled into the underlying bone segments 21a-b at a desired angular orientation, and the bone anchors 22 inserted into the pre-drilled guide bores.

Figure 6A:
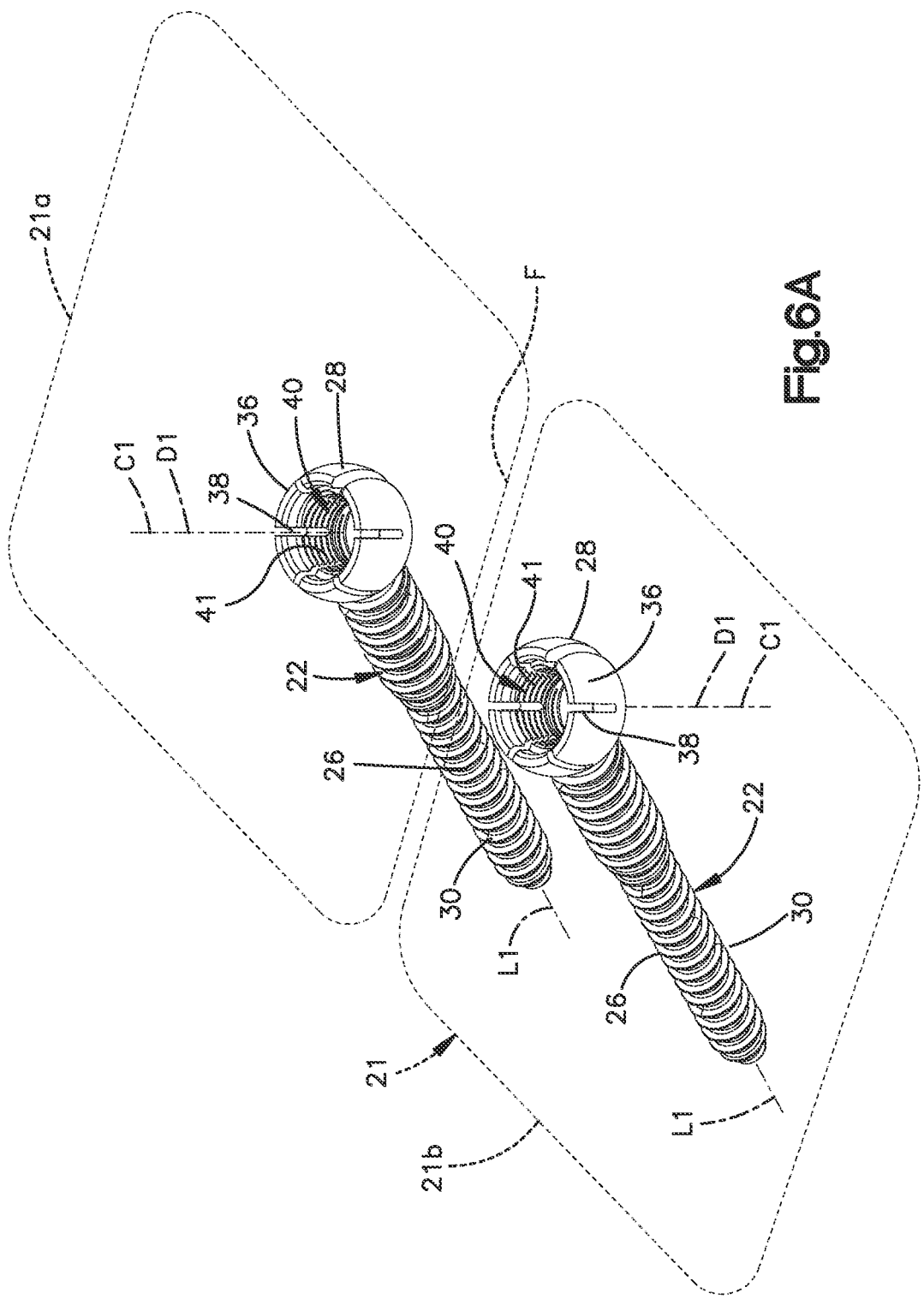
FIG. 6A is an exploded view showing a pair of first anchors fixed to underlying bone segments.
Figure 6C:
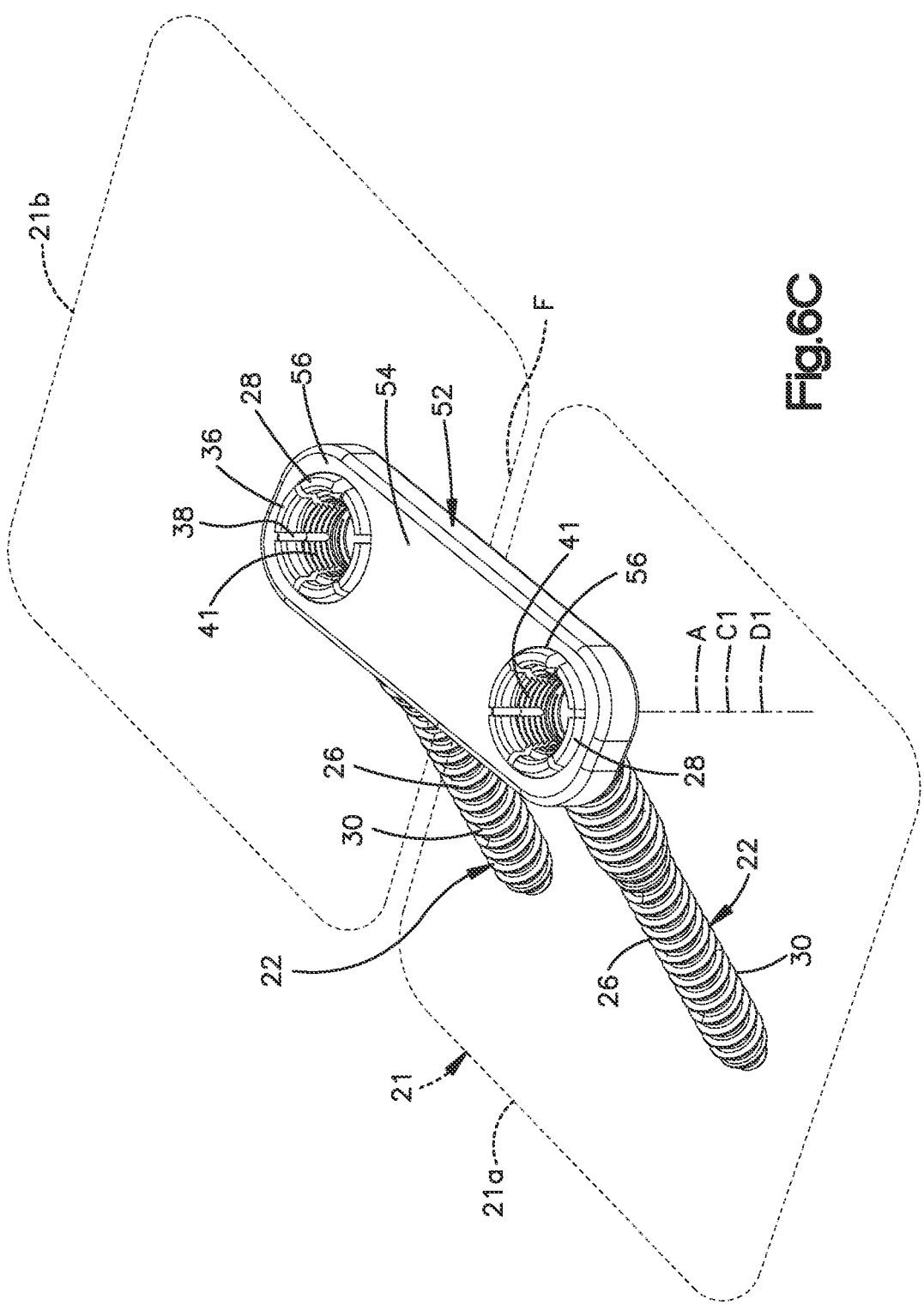
FIG. 6C is a view similar to FIG. 6B, but showing the bone plate attached to the first anchors.

Once the bone anchors 22 have been inserted into the underlying bone segments 21a-b at a desired depth as illustrated in FIG. 6A, the surgeon may operatively couple the bone plate 52 to the pre-inserted first bone anchors 22. In particular, the bone plate 52 is placed over-top of the bone anchors 22 as illustrated in FIG. 6B, and brought down onto the bone anchors 22 such that the apertures 56 receive the corresponding heads 28. The retention tabs 36 compress radially inward until the mating surfaces of the head 28 and the aperture 56 are aligned, thereby causing the plate 52 to be "snapped" or "clicked" onto the head 28 of each bone anchor 22 after the bone anchors 22 have been affixed to underlying bone as shown in FIG. 6C. In this regard, the surgeon is provided with tactile feedback once the bone plate 52 has been mated with the bone anchor heads 28.

Once the heads 28 have been disposed in the apertures 56, the spherical or convex outer surfaces 35 of the heads 28 and the mating inner surface of the aperture 56 allows the bone anchor 22 to polyaxially rotate with respect to the bone plate 52. Otherwise stated, the bone anchor 22 can be inserted into the aperture 56 at any desired angular orientation so long as the second bone anchor 24 is able to pass through the bore 40 of the head 28 and into underlying bone. The first bone anchor 22 can be inserted into the underlying bone to provide compression of the plate 52 against the bone segments if desired.

Figure 6D:
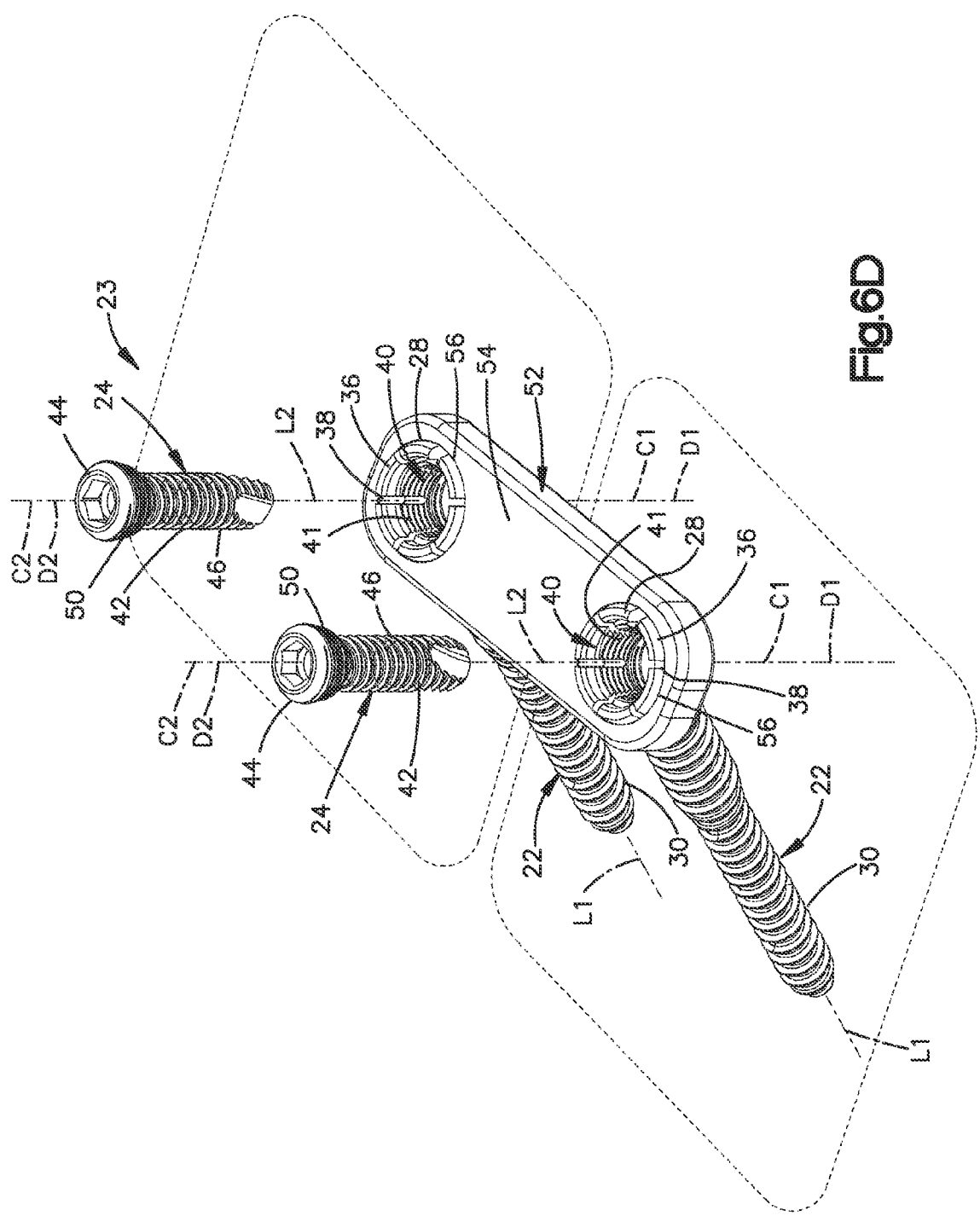
FIG. 6D is a view similar to FIG. 6C, but showing a pair of second anchors aligned for insertion into the first anchors and the underlying bone segments.

Next, referring to FIG. 6D, second bone anchors 24 are inserted into the head 28 of a respective first bone anchor 22 and into the respective underlying bone segments 21a-b. In particular, the shaft 42 of the first bone anchor 22 is driven linearly through the bore 40 until either the distal end 42b of the shaft 42 engages the bone 21, or the threads 41 and 50 engage. It should be appreciated that the shaft 42 of the second bone anchor 24 can extend in a direction substantially perpendicular to the bone plate 52. Typically the shaft 42 engages the underlying bone 21 before the threads 41 and 50 engage. The vertical thickness of the plate body 54 is less than the vertical height of the head 28, such that the proximal end 26a of the shaft 26 does not interfere with the plate 52 when the plate 52 is affixed to the heads 28.

Figure 6E:
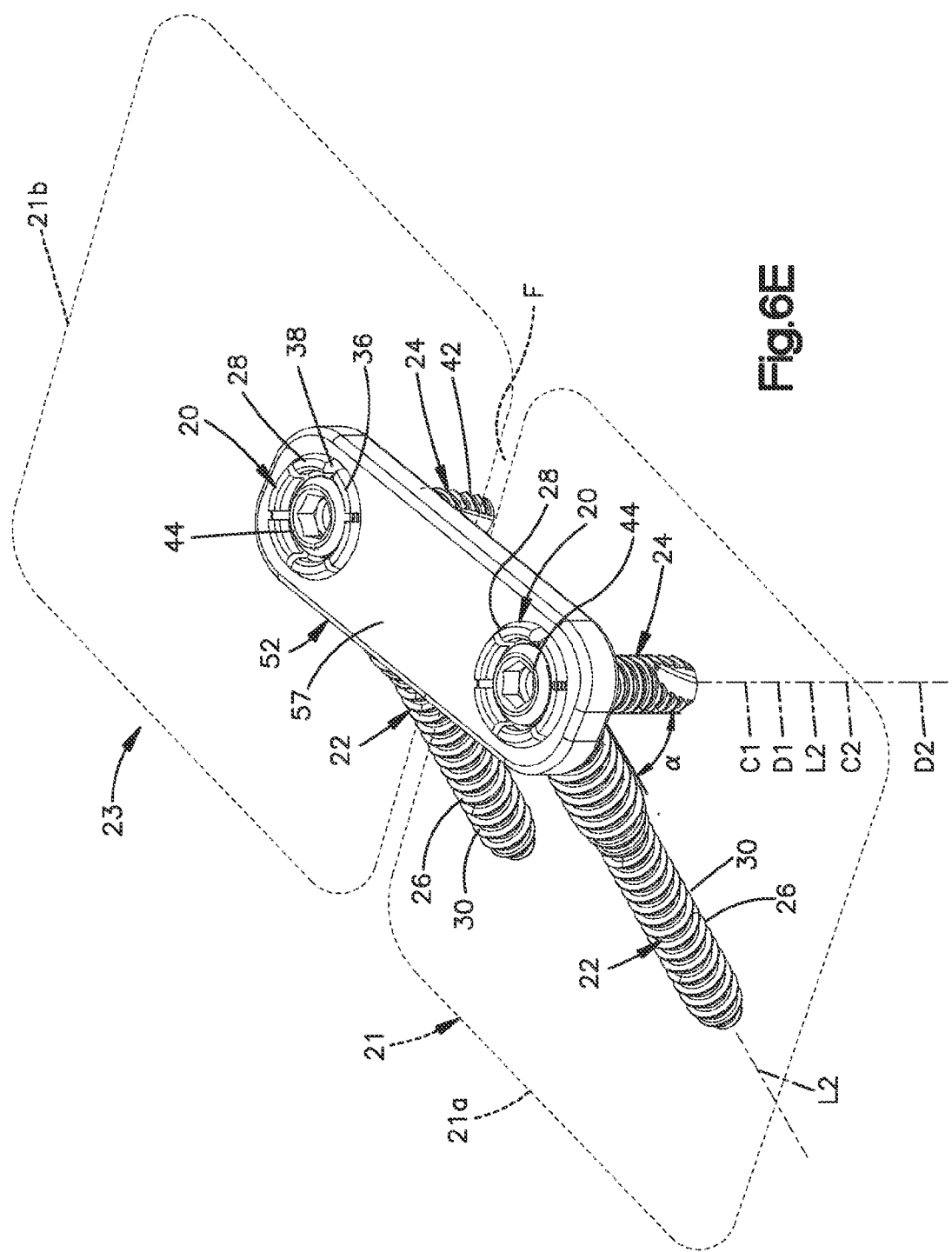
FIG. 6E is a view similar to FIG. 6D, but showing the second anchors inserted and attached to the first anchors, and further attached to the underlying bone segments.

The bone anchor 24 can then be rotated to longitudinally advance the shaft 42 of the second bone anchor 24 into the bone 21, and to longitudinally advance the head 44 inside the head 28 of the first bone anchor 22, such that the threads 50 extending in from the head 28 mate with the threads 41 extending out from the head 44 until the first and second bone anchors 22 and 24 are locked together as illustrated in FIG. 6E. Thus, the shaft 26 of the first bone anchor 22 extends oblique with respect to the bone plate 52 and underlying bone 21, and the shaft 42 of the second bone anchor 24 extends perpendicular with respect to the bone plate 52 and underlying bone 21, though it should be appreciated that both shafts 26 and 42 could alternatively extend in a direction oblique to the bone plate 52 (and the underlying bone 21).

As the distal end 44b of the head 44 of the second bone anchor 24 engages the proximal end 28a of the head 28 of the first bone anchor 22, the retention tabs 36 flex radially outward against the inner surface 58 of the aperture 56, thereby causing a frictional fit that secures the position of the first bone anchor 22 with respect to the plate. Otherwise stated, the head 28 expands against the bone plate 52 as the second bone anchor 24 mates with the first bone anchor 22. In particular, the outer surface 45 of the head 44 can taper radially outward in a direction from the distal end 44b toward the proximal end 44a. Accordingly, insertion of the second bone anchor 24 into and through the bore 40 radially expands the head 28 of the first bone anchor 22 against the inner surface 58 of the aperture 56.

Furthermore, as described above, both the radially inner surface 33 of the bone anchor head 28 and the radially outer surface 45 of the bone anchor head 44 are threaded so that the bone anchors 22 and 24 mate with each other when the first bone anchor 22 receives the second bone anchor 24, thereby securing the second bone anchor 24 to both the first bone anchor and furthermore to the bone plate 52. Thus, in use, the anchor-in-anchor bone fixation system 20 includes a first bone anchor 22 having an expandable head 28 and a locking compression screw mechanism to lock a non-parallel second bone anchor in a bone plate 52. Accordingly, the bone fixation system 20 allows the placing of two non-parallel bone anchors in a relatively small plate area so that a higher level of stability can be achieved with respect to a bone plate that receives a single bone anchor in each aperture to affix the bone plate to underlying bone segments. Because one of the bone anchors (the first bone anchor 22 as illustrated) is angularly offset with respect to the vertical direction of the second bone anchor 24, longitudinal forces applied to the second bone anchor that might otherwise cause migration in the bone 21 are translated to the shaft 26 of the first bone anchor 22, which resists the longitudinal forces that would tend to pull the bone anchor 24 out of the underlying bone 21.

Alternatively, the bone plate 52 can be placed against the bone segments 21a-b, and the shafts 26 can be inserted through the apertures 56 prior to affixing the shafts into the underlying bone. In this alternative embodiment, the bone anchors 20 are inserted into the underlying bone to a desired depth, and the plate 52 is brought up against the heads 28. If the slots 38 separating the retention tabs 36 extend significantly into the distal portion 28b of the heads 28, then the tabs 36 can compress radially inward as the plate is brought up over the heads 28. Alternatively the head 28 can include a single slot 38 that extends vertically through the head 28 so as to define a pair of tabs 36 that are separated at only one circumferentially outer end (see slot 138 in FIGS. 7-8). Alternatively, the outer surface 35 of the head 28 of the first bone anchor 22 can extend substantially linearly, for instance longitudinally, such that the aperture 56 fits easily onto the head 28. Once the head 44 is fixed inside the head 28, the radially outer surface 45 expands radially outward against the bone plate 52 in the manner described above, thereby securely fastening the bone anchors 22 and 24 to the bone plate 52.

While the bone fixation system 20 and the bone fixation assembly 23 have been illustrated and described in accordance with the first and second bone anchors 22 and 24 constructed in accordance with one embodiment, it is envisioned that bone fixation systems and assemblies can be provided in accordance with numerous alternative embodiments whereby a second bone anchor extends through a bore formed in the head of a first bone, such that the first and second bone anchors join to an underlying structure, segments of an underlying structure, or different structures.

Figure 7A:
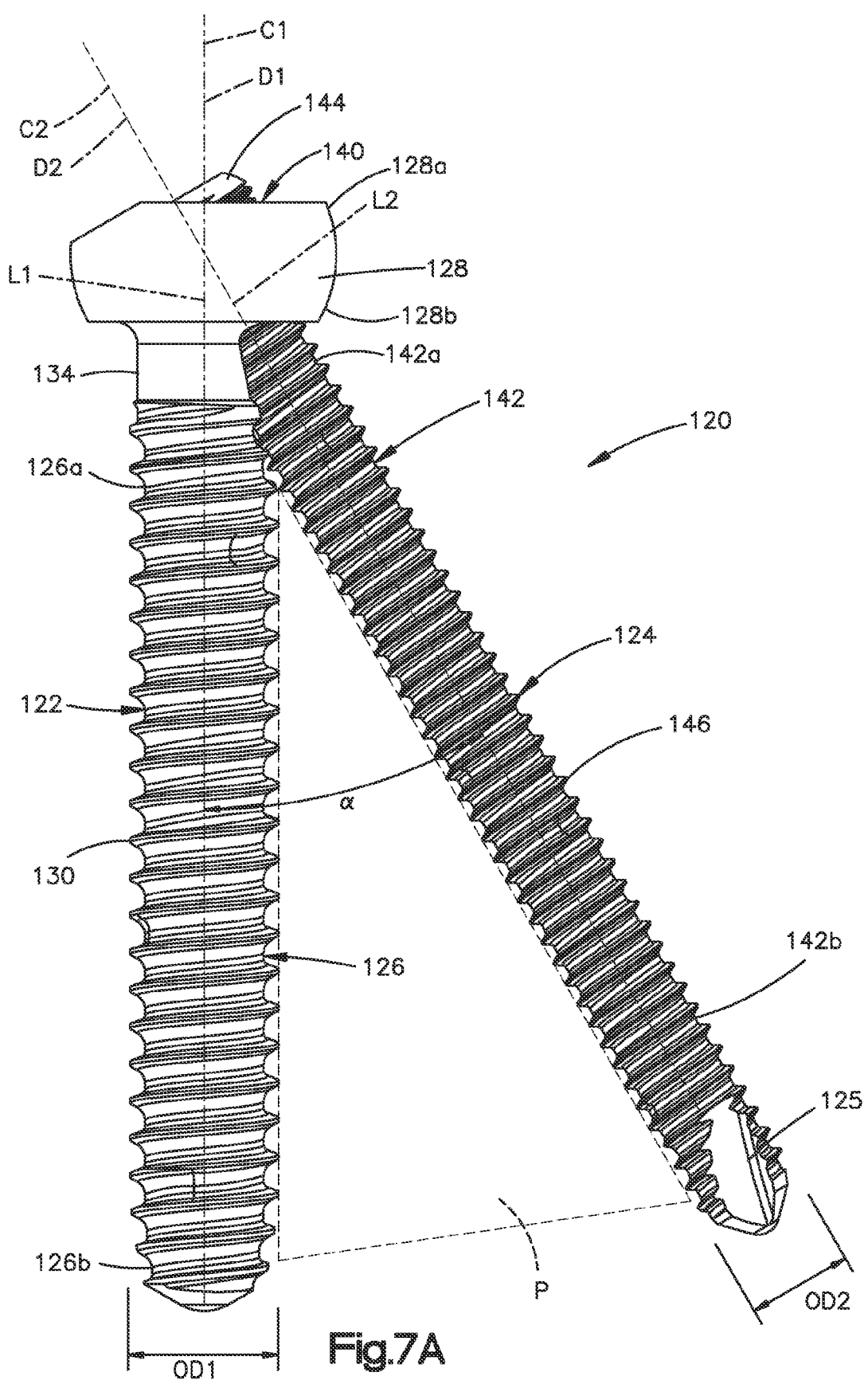
FIG. 7A is a perspective view of an anchor-in-anchor system constructed in accordance with another embodiment and including a first bone anchor receiving and attached to a second bone anchor.
Figure 7B:
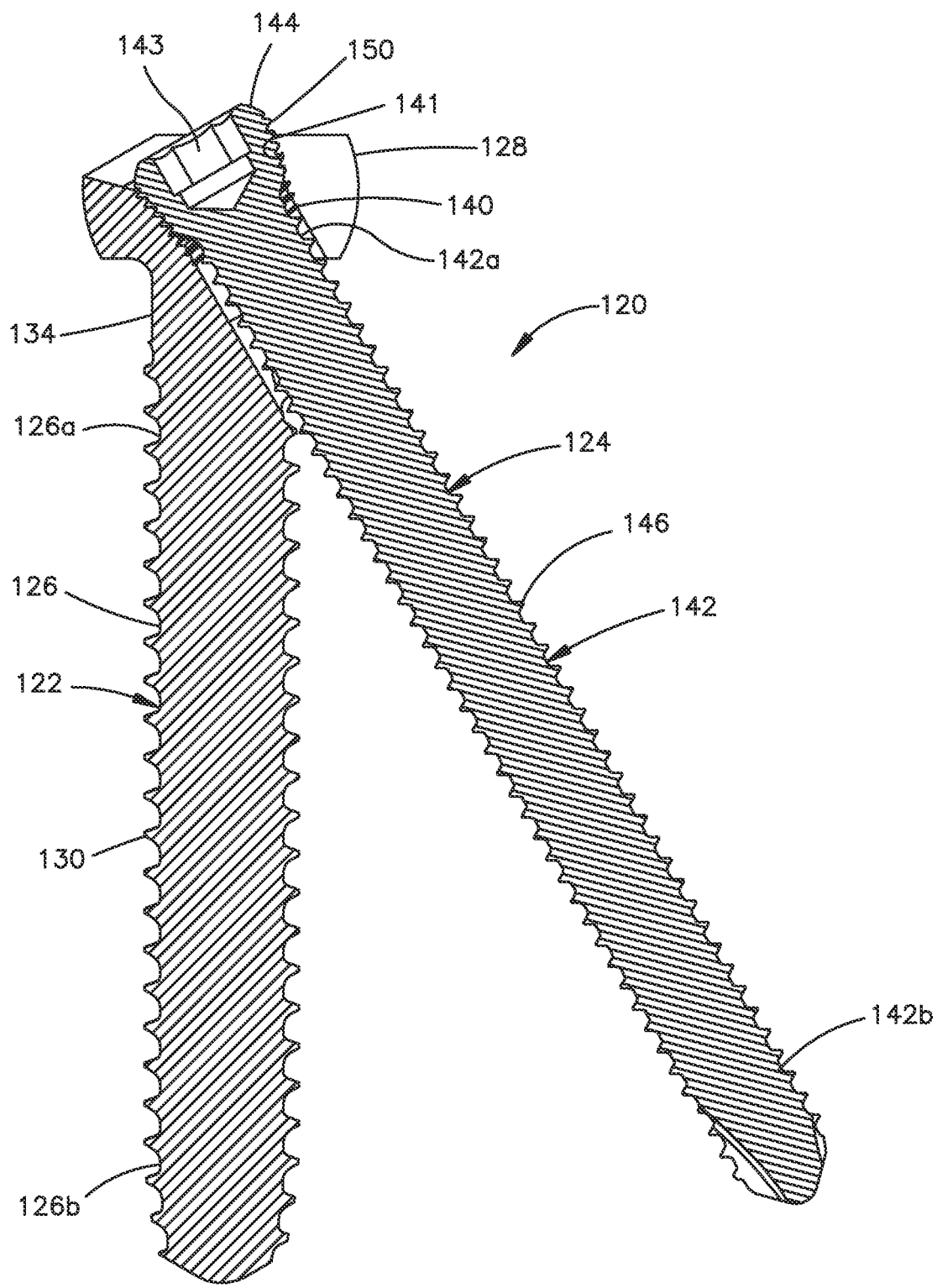
FIG. 7B is a sectional side elevation view of the anchor-in-anchor system illustrated in FIG. 7A.

For instance, referring now to FIGS. 7A-C, an anchor-in-anchor fixation system 120 is illustrated whereby reference numerals corresponding to like elements of the fixation system 20 described above are incremented by 100. Thus, the fixation system 120 includes a first or primary bone anchor 122 and a second or auxiliary bone anchor 124 that is received in the head 128 of the first bone anchor 122. The second bone anchor 124 is constructed as described above with respect to the second bone anchor 24, while the first bone anchor 122 is constructed such that the head 128 is orientated parallel with respect to the shaft 126.

In particular, the proximal end 126a of the shaft 126 is attached to the distal end 128b of the head 128, such that the shaft 126 is centrally disposed with respect to the head 128 and extends longitudinally down from the head 128. Thus, the central axis D1' that extends normal with respect to the proximal and distal ends 128a-b is parallel and coincides with the longitudinal axis L1 of the shaft 26. It should be appreciated, of course, that the shaft 126 could be offset from the central axis D1 of the head 128. The bore 140 extends through the head 128 along a central axis C1 that is angularly offset with respect to both the longitudinal axis L1 of the shaft 126, and the central axis D1 that extends normal with respect to the proximal and distal ends 128a-b of the head 128. In particular, the central axis C1 of the bore 140 forms an acute angle α with respect to the longitudinal axis L1 and the central axis D1'. Thus, the angle α is between 0° and 90°, such as between 40° and 60°. The head 128 can include retention tabs of the type described above with respect to the head 28 of the bone anchor 22, or the head 128 can be circumferentially continuous at and between the proximal and distal ends 128a-b as illustrated in FIG. 7A.

Figure 8A:
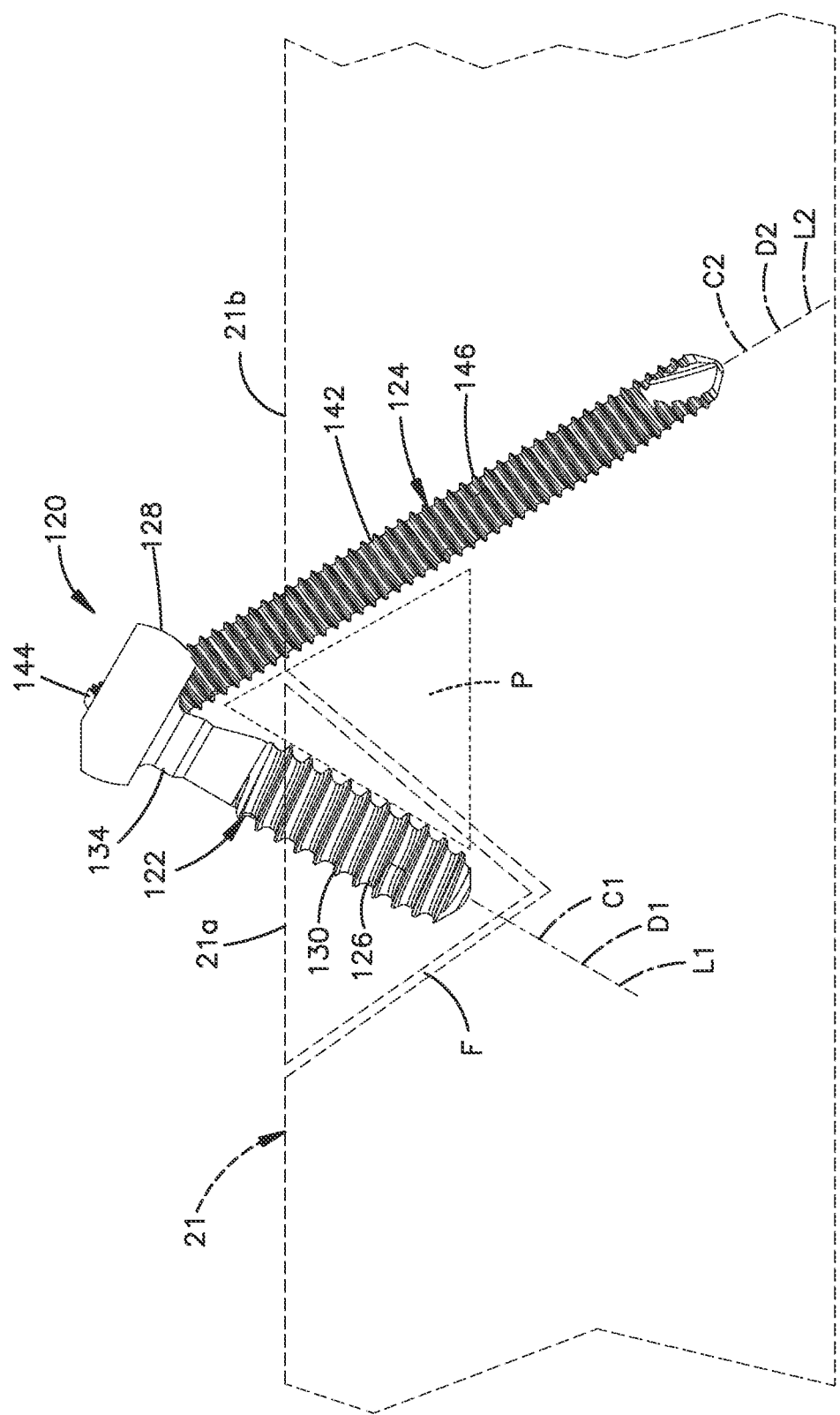
FIG. 8A is a side elevation view of the anchor-in-anchor system illustrated in FIG. 7A attached to underlying bone.

Referring now also to FIG. 8A, the fixation system 120 can be used as a stand-alone system to couple two or more bone fragments together, fir example, in a "butterfly" fracture fixation procedure of a long bone, which may have occurred as a result of traumatic loading. As illustrated, the bore 140 of the first bone anchor 122 is configured to receive the second bone anchor 124, such that the first and second bone anchors 122 and 124 are fastened together, and are also fastened to underlying bone 21. Thus, during use, the surgeon forms an incision to access a targeted area of the underlying bone 21. Next, the first bone anchor 122 is driven, for instance screwed, into the underlying bone 21 or bone segment 21a, such that the threads 130 engage and attach the bone anchor to the underlying bone 21.

The first bone anchor 22 is inserted into the underlying segment such as a bone segment 21a at a sufficient depth, and is rotated until the axis C1 of the bore 140 is aligned with a desired insertion location of a second underlying segment such as a second bone segment 21b. In this regard, it should be appreciated that the first bone segment 122 can be inserted into the bone segment 21a in a direction normal to the plane defined by the underlying bone 21, or can be inserted in a direction angularly offset with respect to a direction normal to the plane defined by the underlying bone 21.

Once the first bone anchor 122 has been fastened to the underlying bone such that the axis C1 is aligned with a target location for the second bone anchor 124, the second bone anchor 124 is inserted into the underlying bone 21, such as segment 21b, through the head 128 of the first bone anchor 122. The second bone anchor 124 can be inserted into the underlying bone 21 through the same incision that received the first bone anchor 122, or through a second incision as desired. Thus, the first bone anchor 122 can be inserted, for instance, into a fragmented long bone segment 21a, while the second bone anchor 124 can be inserted, for instance, into a non-fragmented long bone segment 21b, thereby securing the fragmented bone segment 21a to the non-fragmented bone segment 21b. As illustrated, the shafts 126 and 142 of the first and second bone anchors 122 and 124 each extend oblique with respect to the underlying bone 21, though one of the shafts could alternatively extend substantially perpendicular with respect to the underlying bone in the manner described above.

While the fixation system 120 has been illustrated and described as being used to secure a free-floating bone fragment to a long bone, it should be appreciated that the anchor-in-anchor fixation systems as described herein can also be used to secure a bone fragment in other parts of the body as well, including but not limited to the cranium, face, hands, feet, pelvis, and the like. The anchor-in-anchor fixation systems of the type described herein can also be used to secure one fragment to another fragment (for instance one bone fragment to another bone fragment), or one structure to another structure (for instance one bone to another bone).

It will also be appreciated that anchor-in-anchor bone fixation systems enable a smaller auxiliary fixation device such as, for example, a plate, an intramedullary nail or screw, an intervertebral implant, or the like, to be used while enabling the surgeon to insert a larger number of bone anchors, such as bone anchors 122 and 124, to withstand anticipated loads. Moreover, when locked inside one another, the bone anchors form a stable triangular load bearing plane P and are thus better able to withstand higher forces and prevent subsidence or migration. That is, because the bone anchors 122 and 124 are angled with respect to each other, each bone anchor resists migration within the bone due, for instance, to longitudinal forces applied to the other bone anchor that would tend to pull the bone anchor out of the underlying bone 21.

Referring now to FIGS. 7A-C and 8B-C, the anchor-in-anchor fixation assembly 23 can alternatively or additionally include one or more anchor-in-anchor bone fixation systems 120 in combination with an auxiliary fixation device such as a bone plate 152 configured for fixation of one or more long bones or bone fragments in a patient's body generally in the manner described above with respect to the bone fixation system 20. In particular, a plurality of first bone anchors 122 is installed in the bone plate 152 such that each head 128 is disposed in a corresponding aperture 156. When installed, the shafts 126 extend down from the plate 152 such that the longitudinal axis L1 extends in a direction substantially parallel and coincident with the central axis A of the corresponding aperture 156, and the central axis C1 of the bore 140 defines the angle α with respect to the central axis A. It should thus be appreciated that the shafts 126 therefore extend in a direction substantially perpendicular to the bone plate 152, though it should be appreciated that the shafts 126 could alternatively define a non-perpendicular angle with respect to the bone plate 152.

Figure 8B:
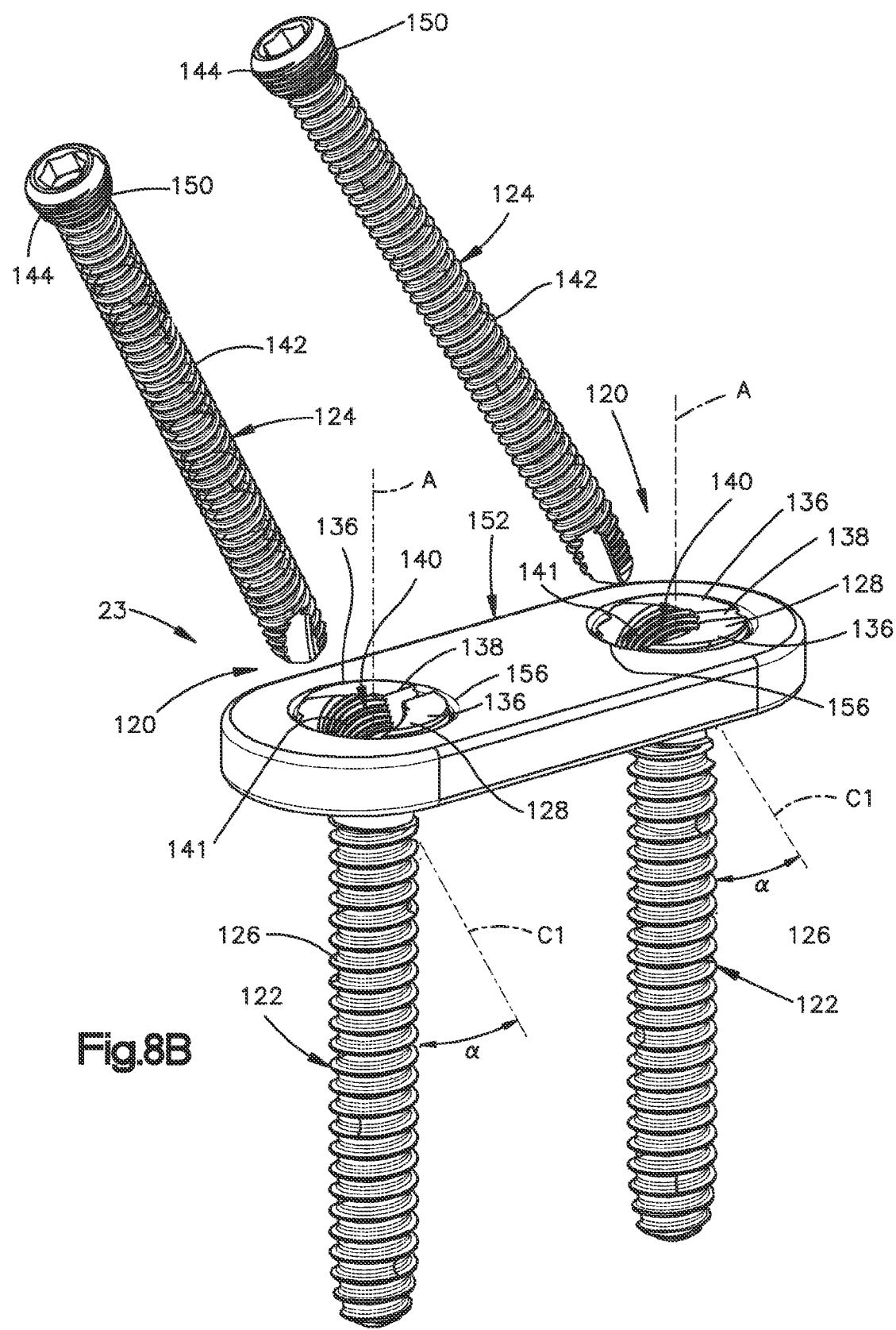
FIG. 8B is an exploded view showing the first anchor illustrated in FIG. 7A attached to a bone plate, and the second anchor illustrated in FIG. 7A aligned for insertion into the first anchor.
Figure 8C:
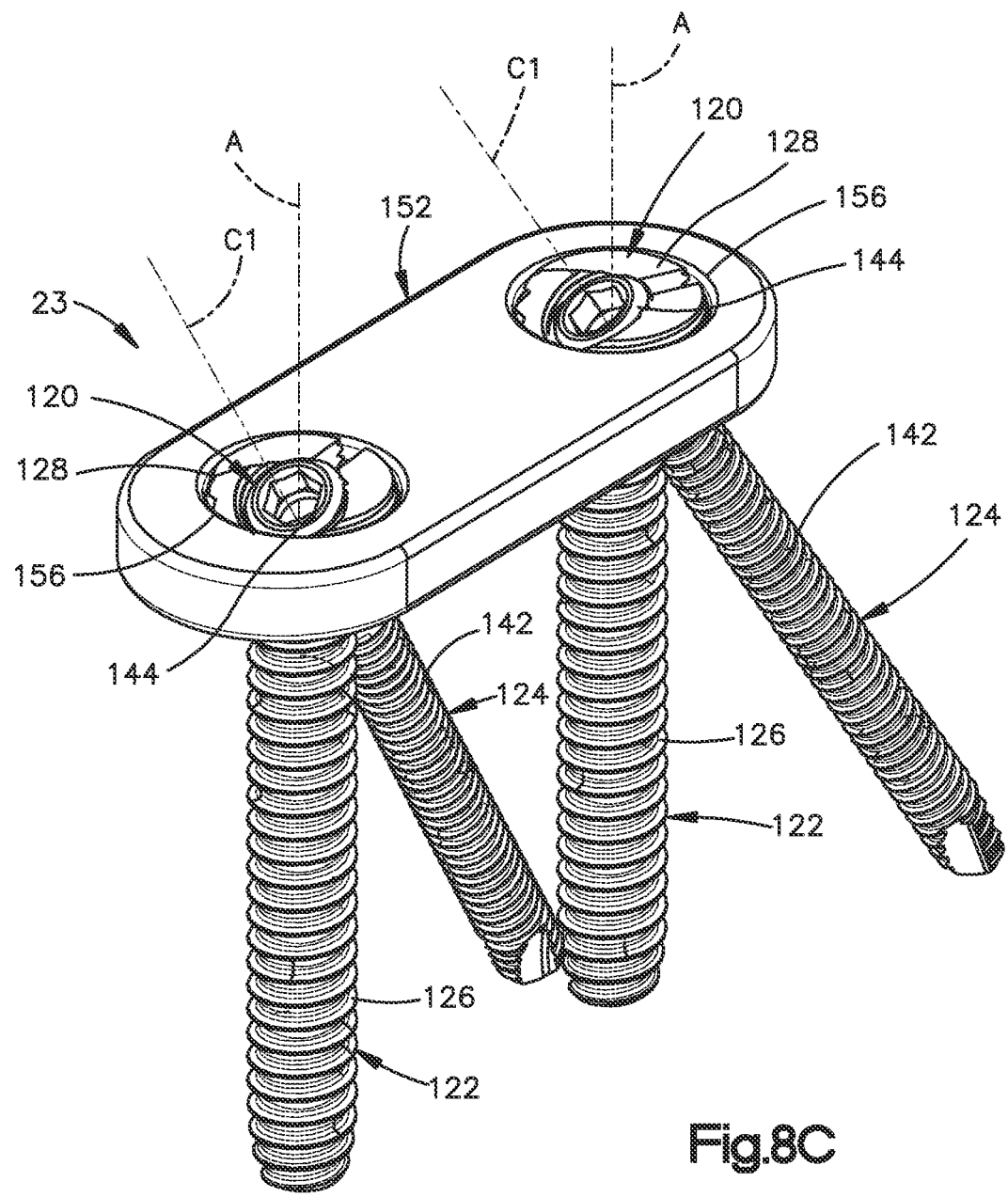
FIG. 8C is an exploded view similar to FIG. 8B, but showing the second anchor inserted in, and attached to, the first anchor.

Once the first bone anchor 122 has been positioned such that the central axis C1 is aligned with a target location of the second bone anchor 124, the second bone anchor 124 is fastened to the first bone anchor 122 in the manner described above, such that the shaft 142 extends down from the plate 152 in a direction coincident with the central axis C1, so as to define the angle α with respect to the axis A. As illustrated in FIGS. 8B-C, a slot 138 extends vertically through the head 128 so as to define a pair of retention tabs 136 separated by the slot 138. Accordingly, the tapered head 144 causes the head 128 to flex radially outward against the inner surfaces of the apertures 156 so as to lock the head 128 against the plate 152 in the manner described above. The shaft 126 of the first bone anchor 122 thus extends perpendicular with respect to the bone plate 152 and underlying bone 21, and the shaft 142 of the second bone anchor 124 extends oblique with respect to the bone plate 152 and underlying bone 21, though it should be appreciated that both shafts 126 and 142 could extend oblique with respect to the bone plate 152 and underlying bone 21.

Alternatively, the bone plate 152 can be placed against the bone segments 21a-b, and the shafts 126 can be inserted through the apertures 156 prior to affixing the shafts into the underlying bone. In this alternative embodiment, the heads 128 are brought down into the apertures 156 of the bone plate 152. Once the head 144 is coupled to the head 128, the radially outer surface 145 expands radially outward against the bone plate 152 in the manner described above, thereby securely fastening the bone anchors 122 and 124 to the bone plate 152.

Furthermore, while the bone anchors 22, 24, 122, and 124 have been described in accordance with particular illustrated embodiments whereby the threads extend along an entirety of the shaft, for instance at and between the proximal and distal ends of the shaft, the bone anchors used in combination with any of the bone fixation systems described herein can be alternatively constructed.

Figure 9A:
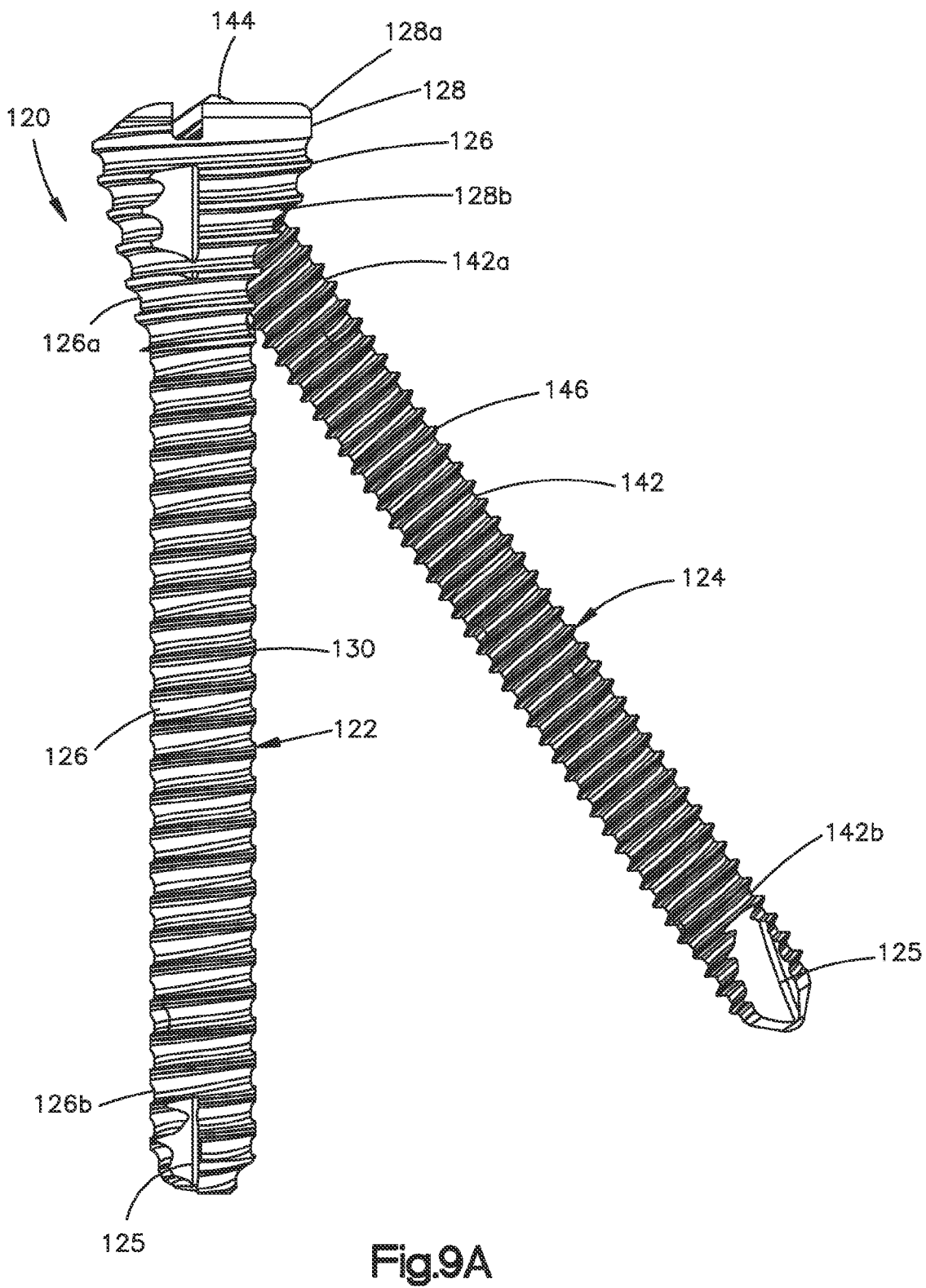
FIG. 9A is a side elevation view of the anchor-in-anchor system illustrated in FIG. 7A constructed in accordance with an alternative embodiment.
Figure 9B:
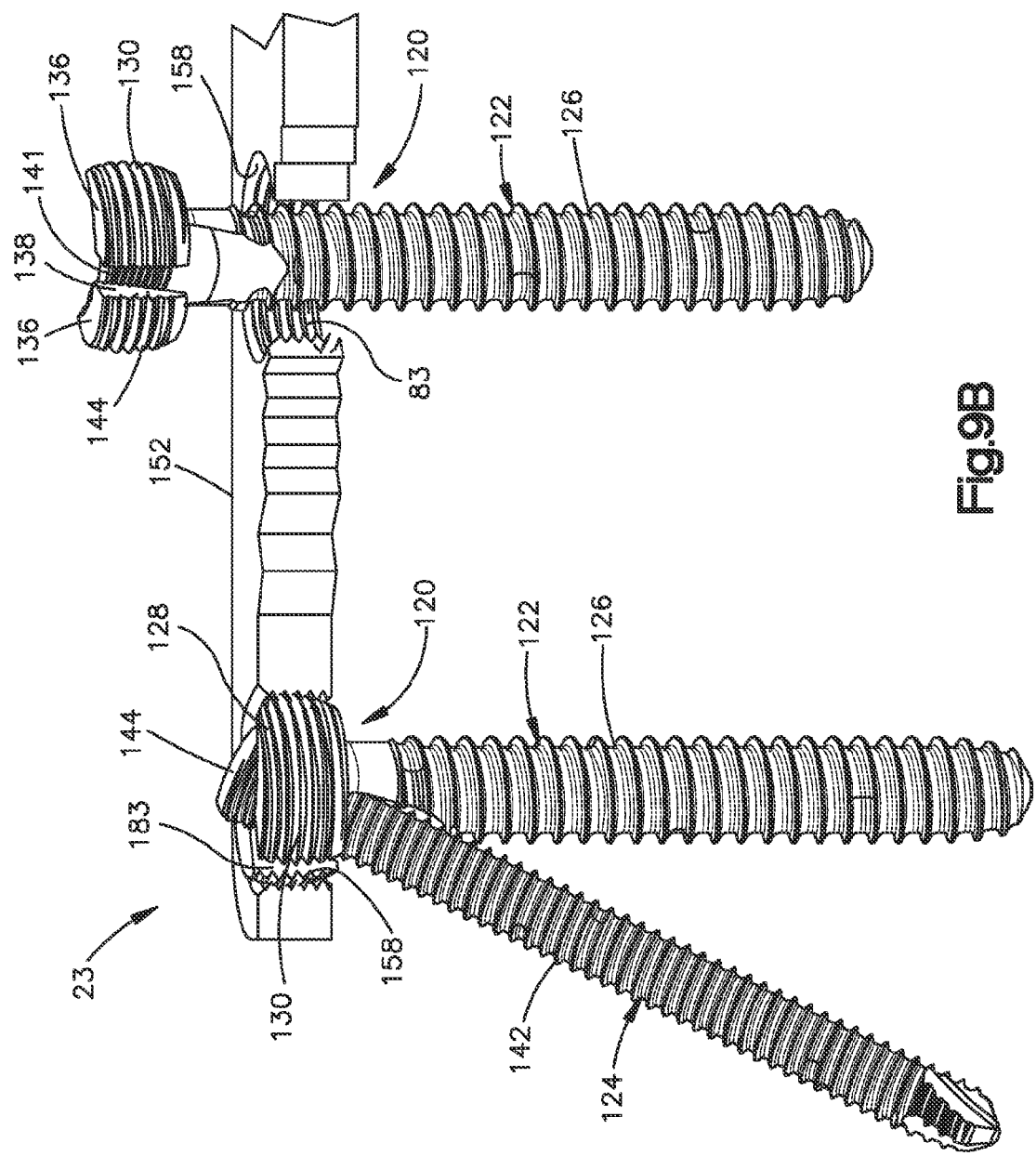
FIG. 9B is a sectional side elevation view of a bone plate incorporating the anchor-in-anchor system illustrated in FIG. 9A.

For instance, referring to FIGS. 9A-B, the first bone anchor 122 is illustrated as including a plurality of threads 130 that extend radially out from the shaft 126 along the full length of the shaft 126 in the manner described above, and also extend radially out from the head 128, thereby providing a locking screw. The threads 130 extending out from the head 128 are configured to engage complementary threads 183 extending radially in from the inner surface 158 of the aperture 156 to further affix the first bone anchor 122 to the bone plate 152. Thus, the first bone anchor 122 is threadedly coupled to the bone plate 152, and the second bone anchor 124 is threadedly coupled to the first bone anchor 122.

In this manner, the first bone anchor 122 is inserted into the underlying bone and through the aperture 156, the shaft 126 is first inserted through the apertures 156 such that the threads 130 extending out from the head 128 engage the threads in the inner surface 158 to secure the bone anchor 122 to the bone plate 152. In this regard, it should be appreciated that the threaded engagement between the head 128 and the bore 156 fixes the angular position of the first bone anchor 122 relative to the bone plate 152 such that the second bone anchor head 144 need not expand the head 128 against the inner surface 158 in the manner described above. Furthermore, the threaded engagement between the head 128 and the bone plate 152 allows the bone anchors 122 and 124 to attach the plate 152 to the underlying bone without compressing the plate 152 against the underlying bone.

While the bone plate 52 has been illustrated as attached to underlying bone 21 via the fixation systems 20 and the bone plate 152 has been illustrated and described as attaching to underlying bone 21 via the fixation systems 120, it should be appreciated that one or more fixation systems 20 and 120 could be used in combination to attach either of the bone plates 52 and 152 to the underlying bone 21.

Whether the fixation system 120 is provided as a stand-alone construct (i.e., without an auxiliary fixation device) or in combination with an auxiliary fixation device such as the bone plate 152 to provide a fixation assembly 23, the threaded engagement between the second bone anchor 124 and the first bone anchor 122 allows the head 144 of the second bone anchor 124 to be countersunk within the head 128 of the first bone anchor 122, such that the proximal end 128a of the head 128 is substantially flush to provide a low profile and minimize the trauma associated with the fixation system 120.

Figure 10A:
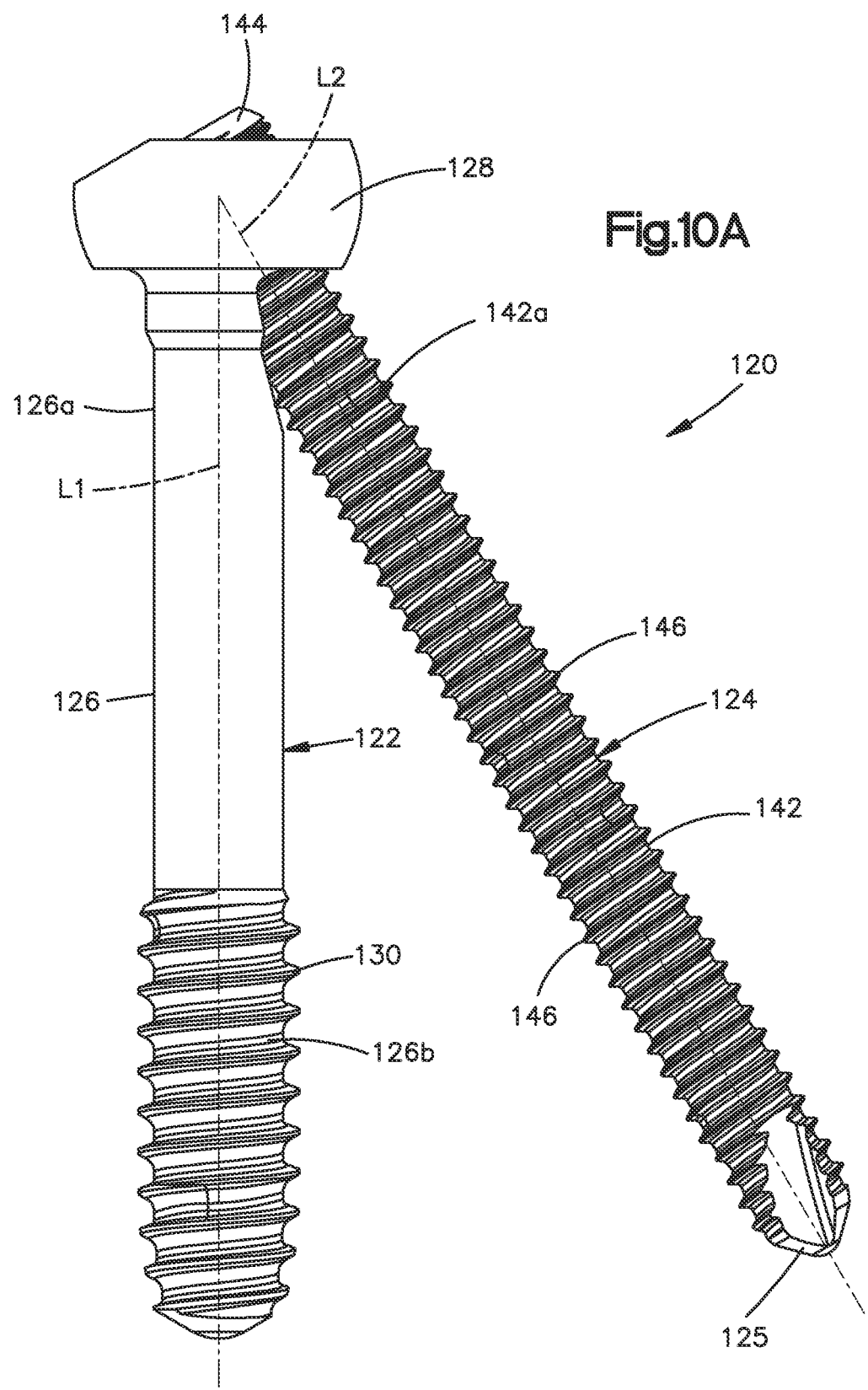
FIG. 10A is a side elevation view of the anchor-in-anchor system illustrated in FIG. 7A constructed in accordance with another alternative embodiment.

Alternatively, referring to FIG. 10A, the first bone anchor 122 can be provided having threads 130 that extend only partially along the shaft 126. As illustrated, the threads 130 extend radially out from the distal end 126b of the shaft, such that the proximal end 126a of the shaft 126 is smooth and devoid of threads. It should be appreciated that the bone anchor 122 could alternatively include one or more fixation ribs extending radially out from the proximal end 126a that engage surrounding bone and resist migration of the bone anchor 122 within the bone. It should be further appreciated that the second bone anchor 124 can likewise present threads 130 that extend only partially along the shaft 142, and in particular extend radially out form the distal end 142b of the shaft 142, such that the proximal end 142a of the shaft is devoid of threads. Threads could additionally or alternatively extend from the heads 128 and 144 in the manner described above.

Figure 10B:
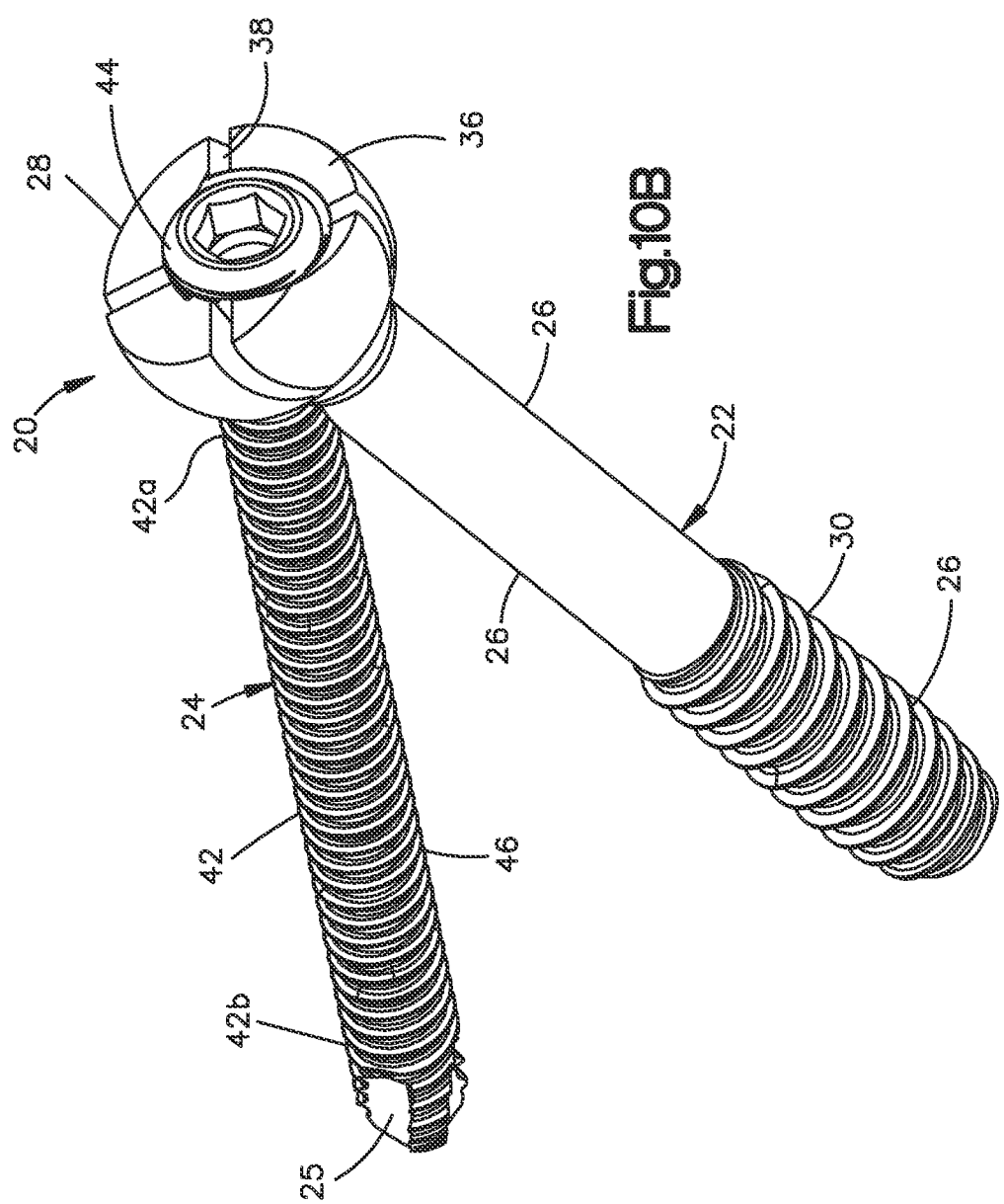
FIG. 10B is a side elevation view of the anchor-in-anchor system illustrated in FIG. 1 constructed in accordance with an alternative embodiment.

Referring to FIG. 10B, the first bone anchor 22 can be provided having threads 30 that extend only partially along the shaft 26. As illustrated, the threads 30 extend radially out from the distal end 26b of the shaft 26, such that the proximal end 26a of the shaft 26 is smooth and devoid of threads. It should be appreciated that the bone anchor 22 could alternatively include one or more fixation ribs extending radially out from the proximal end 26a that engage surrounding bone and resist migration of the bone anchor 22 within the bone. It should be further appreciated that the second bone anchor 24 can likewise present threads 46 that extend only partially along the shaft 42, and in particular extend radially out form the distal end 42b of the shaft 42, such that the proximal end 42a of the shaft is devoid of threads. Threads could additionally or alternatively extend from the heads 28 and 44 in the manner described above.

It should alternatively be appreciated that one or more, up to all of the bone anchors 22, 24, 122, and 124 could be constructed having fully threaded shafts, partially threaded shafts, or shafts that are entirely devoid of threads. For instance, FIGS. 11A-C illustrate example embodiments of the fixation system 20 as including bone anchors 22 and 24 whose shafts 26 and 42 are constructed in accordance with alternative embodiments, though the bone anchors 122 and 124 can be constructed as illustrated and described with respect to the bone anchors 22 and 24.

For instance, referring to FIG. 11A the shaft 26 of the first bone anchor 22 is threaded along its entirety as described above with respect to FIG. 1, however the shaft 42 of the second bone anchor 24 is devoid of threads so as to define an unthreaded nail, rivet, or unthreaded pin. The use of such unthreaded bone anchors can be particularly useful in applications where the fixation system 20 or 120 is being implemented for fixation in cancellous bone. It should be appreciated that the unthreaded bone anchor 24 can include one or more locking teeth 47 projecting radially out from the shaft 42. The teeth 47 can define a screw helix pattern about the shaft 42, but also allow the bone anchor 24 to be hammered into the underlying bone. The radially outer surface 45 of the head 44 flares radially outward in a direction from the distal end 44b toward the proximal end 44a. Accordingly, once the first bone anchors 22 are attached to underlying bone in the manner described above, the shaft 42 of the second bone anchor 24 is inserted into the head 28 of the first bone anchor, and subsequently hammered into the underlying bone. As the head 44 is inserted into the head 28, the outer surface 45 causes the retention tabs 36 to flex radially outward so as to lock the fixation member 22 in the plate 52 as described above.

Referring now to FIG. 11B, the shaft 42 of the second bone anchor 24 is threaded along its entirety as described above with respect to FIG. 1, however the shaft 26 of the first bone anchor 22 is devoid of threads so as to define an unthreaded nail, rivet, or unthreaded pin. The shaft 26 can have a substantially constant diameter as illustrated in FIG. 11A, or the outer diameter can differ along the length of the shaft. For instance, as illustrated, the proximal end 26a of the shaft 26 defines an outer diameter that is greater than the outer diameter at the distal end 26b of the shaft 26a. It should be appreciated that the unthreaded bone anchor 22 can include one or more locking teeth projecting radially out from the shaft 26. Accordingly, the first bone anchors 22 can be hammered into the underlying bone, and the bone plate 52 can be attached to the heads 28 of the bone anchors 22 in the manner described above. The second bone anchors 24 can then be inserted into the underlying bone, and the heads 44 can be attached to the heads 28 of the first bone anchors 22 in the manner described above.

Figure 11C:
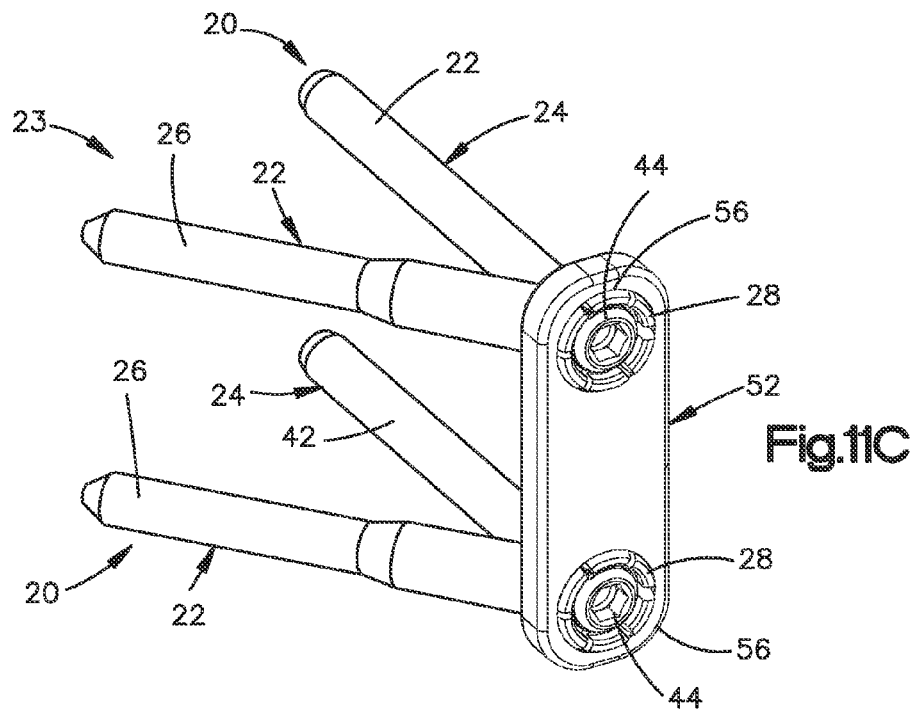

Alternatively still, as illustrated in FIG. 11C, the shafts 26 and 42 of both bone anchors 22 and 24 can be devoid of threads. One or both of the shafts 26 and 42 can present constant outer diameters along their lengths, or can present different outer diameters along their lengths. For instance, the proximal ends 26a of the shafts 26 present an outer diameter greater than that of the distal ends 26b of the shafts 26. During operation, the shaft 26 of the first bone anchor 22 can be hammered into underlying bone, and the bone plate 52 can be attached to the head in the manner described above. Subsequently, the shaft 42 of the second bone anchor 24 can be inserted through the head 28 and driven into underlying bone until the head 44 nests within the head 28, in the manner described above with reference to FIG. 11A.

Figure 12:
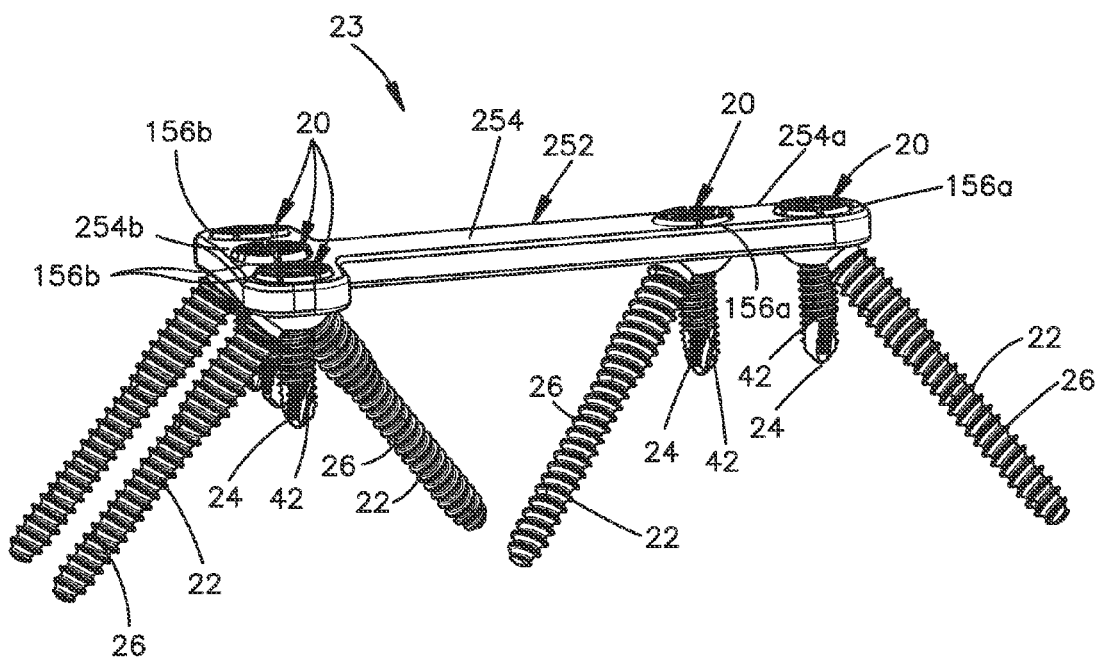
FIG. 12 is a perspective view of an anchor-in-anchor fixation assembly including a plurality of anchor-in-anchor systems attached to a t-shaped bone plate.

While the anchor-in-anchor bone fixation systems 20 and 120 have been described in combination with an elongate plate configured to provide long bone fixation, it should be appreciated that the anchor-in-anchor bone fixation systems of the type described herein could alternatively include bone plates of any suitable size and shape. For instance, referring to FIG. 12, a bone plate 252 is illustrated having reference numerals corresponding to like elements of the bone plate 52 incremented by 200. Therefore, the plate 252 includes a plate body 254 having a first longitudinally elongate section 254a that is configured to extend parallel to the underlying long bone, and a laterally elongate second section 254b disposed at one end of the first elongate section 254a and elongate in a direction perpendicular to the first elongate section 254a. Thus, the plate 252 is T-shaped such that the second elongate section 254b extends generally perpendicular to the underlying long bone. The plate sections 254a-b can further be curved so as to conform to the long bone.

A plurality of longitudinally spaced apertures 256a extends through the first plate section 254a, and a plurality of laterally spaced apertures 256b extends through the second plate section 254b. In one embodiment, it is envisioned that the T-shaped bone fixation plate is configured to attach to a tibia having a fracture that is disposed longitudinally between the plurality of apertures 256a and the plurality of apertures 256b. Either or both of the fixation systems 20 and 120 can be inserted into one or more, up to all, of the apertures 256a-b. As illustrated, the fixation system 20 is inserted into the apertures 256a-b in the manner described above with respect to bone plate 52. It can be appreciated that the shafts 26 of the first bone anchors 22 can be aligned in any angular direction as desired, and can be constructed sufficiently long so as to extend through overlaid bone segment, through the fracture, and into the opposing fractured bone segment.

Figure 13C:
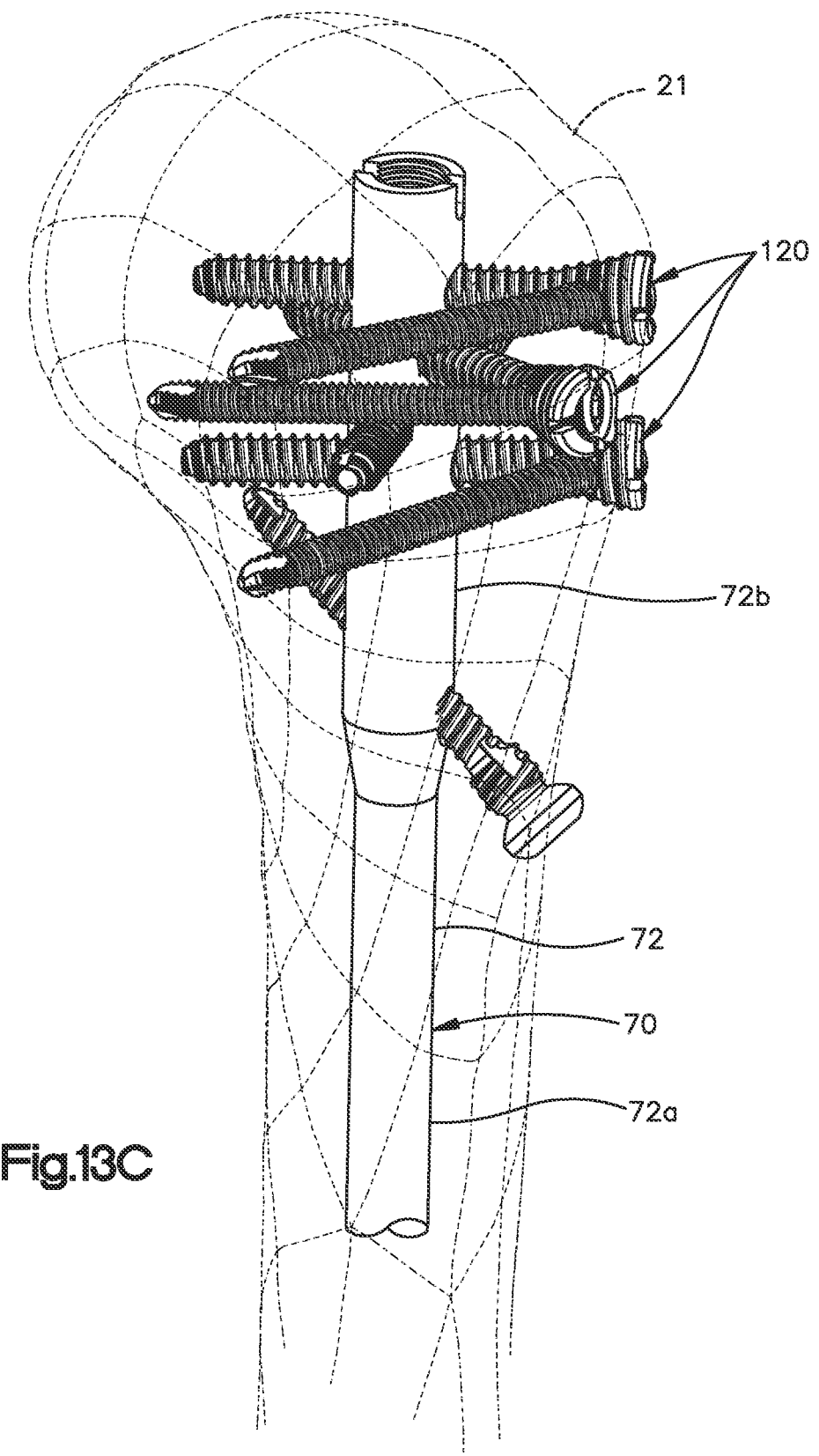
FIG. 13C is a side elevation view of the anchor-in-anchor fixation assembly including a plurality of anchor-in-anchor systems attached to the intramedullary rod and further attached to a long bone.

Referring now to FIGS. 13A-C, the anchor-in-anchor fixation assembly 23 can include one or both fixation systems 20 and 120 and an auxiliary fixation device provided as intramedullary nail, screw, or rod 70 (collectively referred to herein as a "rod") for use in long bone fixation. As generally understood in the art, the intramedullary rod 70 is configured to be inserted into the intramedullary canal of the long bone to be fixed. Referring in particular to FIG. 13A, the intramedullary rod 70 includes a longitudinally extending tubular rod body 72 including a first segment 72a and a second segment 72b coextensive with the first segment 72a. The second segment 72b is illustrated as a head portion of the rod body 72 that defines an outer diameter greater than that of the first segment 72a. The rod defines one or more first bone fixation apertures 74a extending through the first rod segment 72b, and one or more second bone fixation apertures 74b extending through the second rod segment 72b.

The apertures 74a can be longitudinally displaced from each other along the length of the rod segment 72a, and can further be angularly displaced from each other about the circumference of the rod segment 72a. Likewise, the apertures 74b can be longitudinally displaced along the length of the rod segment 72b, and can further be angularly displaced from each other about the circumference of the rod segment 72b. The apertures 74a-b can extend centrally through the rod body segments 72a-b coextensive with the diameter of the segments 72a-b, or offset from the center of the segments 72a-b coextensive with a chord of the segments 72a-b. The apertures 74a-b can also define a longitudinal directional component such that one end of a given aperture is longitudinally displaced with respect to the opposing end of the aperture. While the rod 70 is illustrated as substantially cylindrical as illustrated, it should be appreciated that the rod 70 could assume any suitable alternative shape and size as desired.

As illustrated in FIG. 13B, the anchor-in-anchor bone fixation system 120 is configured to attach the intramedullary rod 70 to surrounding bone. In particular, one of the bone anchors, for instance the first bone anchor 122, is driven into a selected one of the apertures 74, for instance using a screwing, drilling, hammering, or like mechanism to insert the shaft 26 into the selected aperture 74. The bone anchor shaft 126 can define a length so as to terminate inside the rod 70 or extend through the rod 72 without passing through the opposing bone surface, or can define a length sufficient to pass through both the rod 72 and the opposing bone surface. Once the shaft 126 is inserted at a desired rotational position such that the central axis C1 of the bore 140 is aligned with a target location on the bone for fixation, the second bone anchor 124 is attached to the first bone anchor 122 and directly to the bone that surrounds the intramedullary rod 72 without also attaching to the intramedullary rod. It should be appreciated, of course, that the second bone anchor 124 could also attach to an aperture 74 extending through the intramedullary rod 72 if desired.

In accordance with the illustrated embodiment, the shaft 142 is inserted through the bore 140 and driven into the surrounding bone 21, for instance using a screwing, drilling, hammering, or like mechanism to insert the shaft 142 into the surrounding bone 21. In this regard, it should be appreciated that, as in all embodiments of the of anchor-in-anchor bone fixation systems described herein unless otherwise noted, either or both of the bone anchors 122 and 124 could be provided with threaded heads, unthreaded heads, heads including locking tabs 136 or heads that are circumferentially continuous at and between the proximal and distal ends, fully threaded shafts, partially threaded shafts, or unthreaded shafts defining a smooth radially outer surface or including teeth 47 projecting out from the radially outer surface.

While the first bone anchor 122 is configured to be attached to the rod 70 and the second bone anchor 124 is configured to be attached to the surrounding bone, it should be appreciated that the second bone anchor 124 could alternatively be attached to the rod 70 in the manner described above, and the first bone anchor 122 could be attached to the surrounding bone. In this alternative embodiment, the first bone anchor 22 is driven into the bone 21 such that the central axis C1 of the bore 140 is aligned with one of the apertures 74. The second bone anchor 124 is then inserted through the bore 140 such that the shaft 142 extends through and is coupled to the aligned aperture 74.

It should further be appreciated that while the second fixation system 120 has been illustrated as attached to the intramedullary rod 70 and surrounding bone 21 in the manner described above, the first fixation system 20 could alternatively or additionally attach to the intramedullary rod 70 and surrounding bone. For instance, the first bone anchor 22 could attach to one of the apertures 74 and the second bone anchor could attach to the surrounding bone 21 in the manner described above, or the first bone anchor 22 could attach to the surrounding bone 21, and the first bone anchor could attach to one of the apertures 74 in the manner described above.

Referring also now to FIG. 13C, the intramedullary rod 72 can be inserted into the canal 49 of a fractured long bone 21 that defines fracture segments 21a and 21b. The rod 72 is inserted into the canal 49 such that the fracture F is disposed between the first apertures 74a and the second apertures 74b. It should be appreciated that one or more of the fixation systems 120 can attached to the surrounding bone 21 and further attach to one or more, up to all, of the one apertures 74a-b in accordance with any of the embodiments described above. Alternatively or additionally, one or more of the fixation system 120 can attached to the surrounding bone 21 and further attach to one or more, up to all, of the one apertures 74a-b in accordance with any of the embodiments described above.

Thus, the fixation systems 20 and 120 can be used alone or in combination to fasten the intramedullary rod 72 to the surrounding bone. It should be further appreciated in all embodiments described herein, unless otherwise, noted, that the fixation systems 20 and 120 can be used in combination when attaching directly to bone as a stand-alone construct, or when affixing an auxiliary fixation device to an underlying structure such as bone, bone-substitutes or bone-spacers, allografts, autografts, synthetic grafts, and metal or titanium grafts. It should be further appreciated that the bone anchors that attach to the intramedullary rod 72 can be rotated to any desired position, such that the other bone anchor can extend into the surrounding bone at any angular orientation as desired.

In the embodiments illustrated, in FIGS. 13A-C, bone anchors are attached directly to an intramedullary rod and the surrounding bone 21 as stand-alone constructs, wherein the bone anchors are not joined by any additional auxiliary fixation device. However, it should be appreciated that the anchor-in-anchor fixation assembly 23 can further include a second auxiliary fixation device, such as a bone plate usable in combination with a first auxiliary fixation device, such as an intramedullary rod, as will now be described in more detail below with reference to FIGS. 14A-C.

Figure 14A:
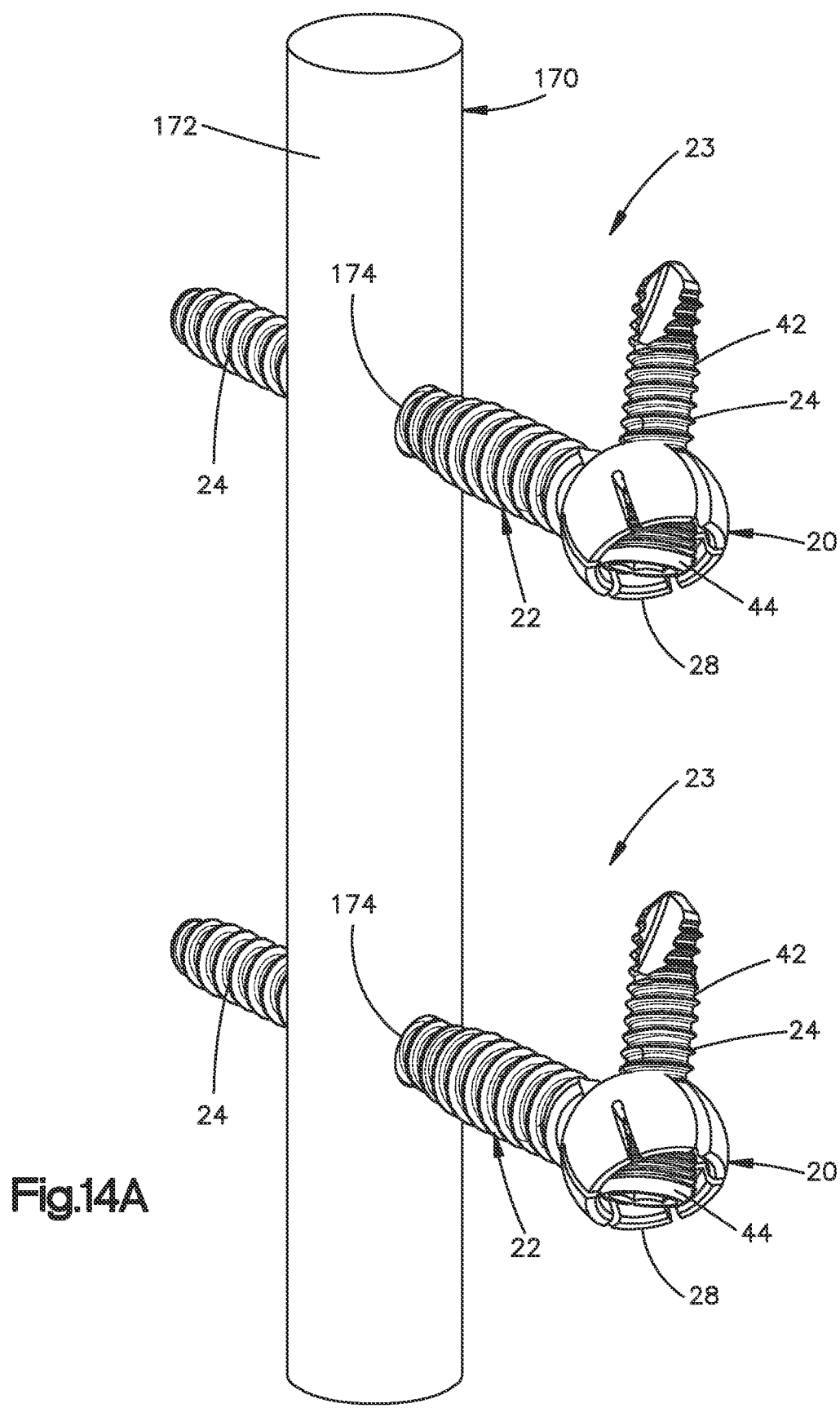
FIG. 14A is a side elevation view of an anchor fixation assembly including a plurality of anchor-in-anchor systems attached to an intramedullary in accordance with an alternative embodiment.

Referring now to FIG. 14A, the anchor-in-anchor fixation assembly 23 is illustrated as including a plurality of bone fixation systems 20 attached to an intramedullary rod 170 constructed in accordance with an alternative embodiment whereby reference numerals corresponding to like elements of the intramedullary rod described above are incremented by 100. The intramedullary rod 170 includes a tubular rod body 172 that defines a substantially constant outer diameter along its length. The rod 172 defines one or more apertures 174 extending through the rod body 172. The rod 172 is configured to be placed in the canal of a long bone such that the apertures 174 are separated by a fracture in the manner described above. As illustrated, the bone fixation system 20 is attached to the apertures 174, and is configured to attach to the surrounding bone in the manner described above, though it should be appreciated that the bone fixation system 120 can be used in combination with the bone fixation system 20 or alone to attach the intramedullary rod 170 to the surrounding bone in the manner described herein.

Figure 14B:
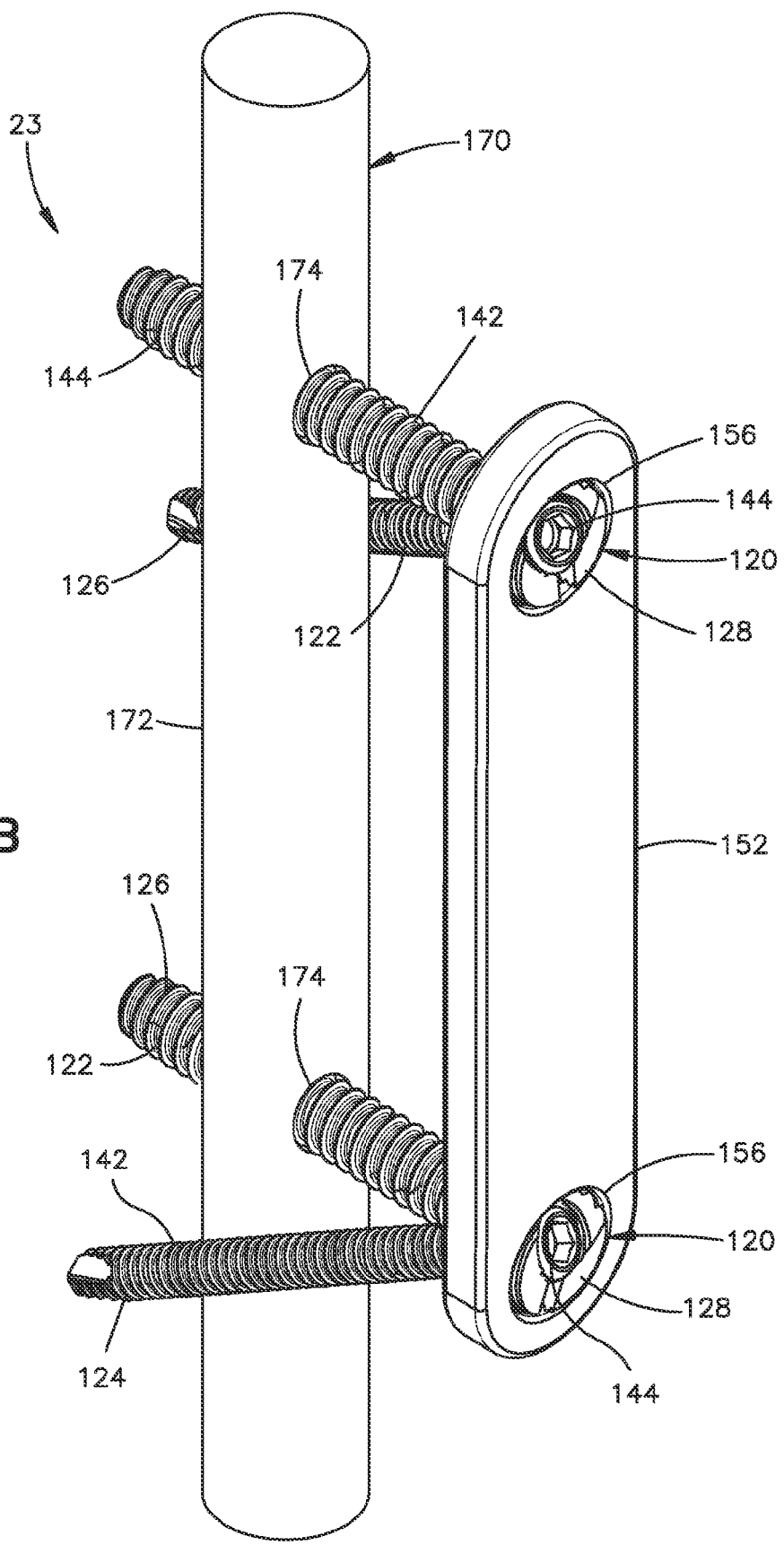
FIG. 14B is a side elevation view of the anchor fixation assembly illustrated in FIG. 14, but including a plate attached to anchor-in-anchor systems.
Figure 14C:
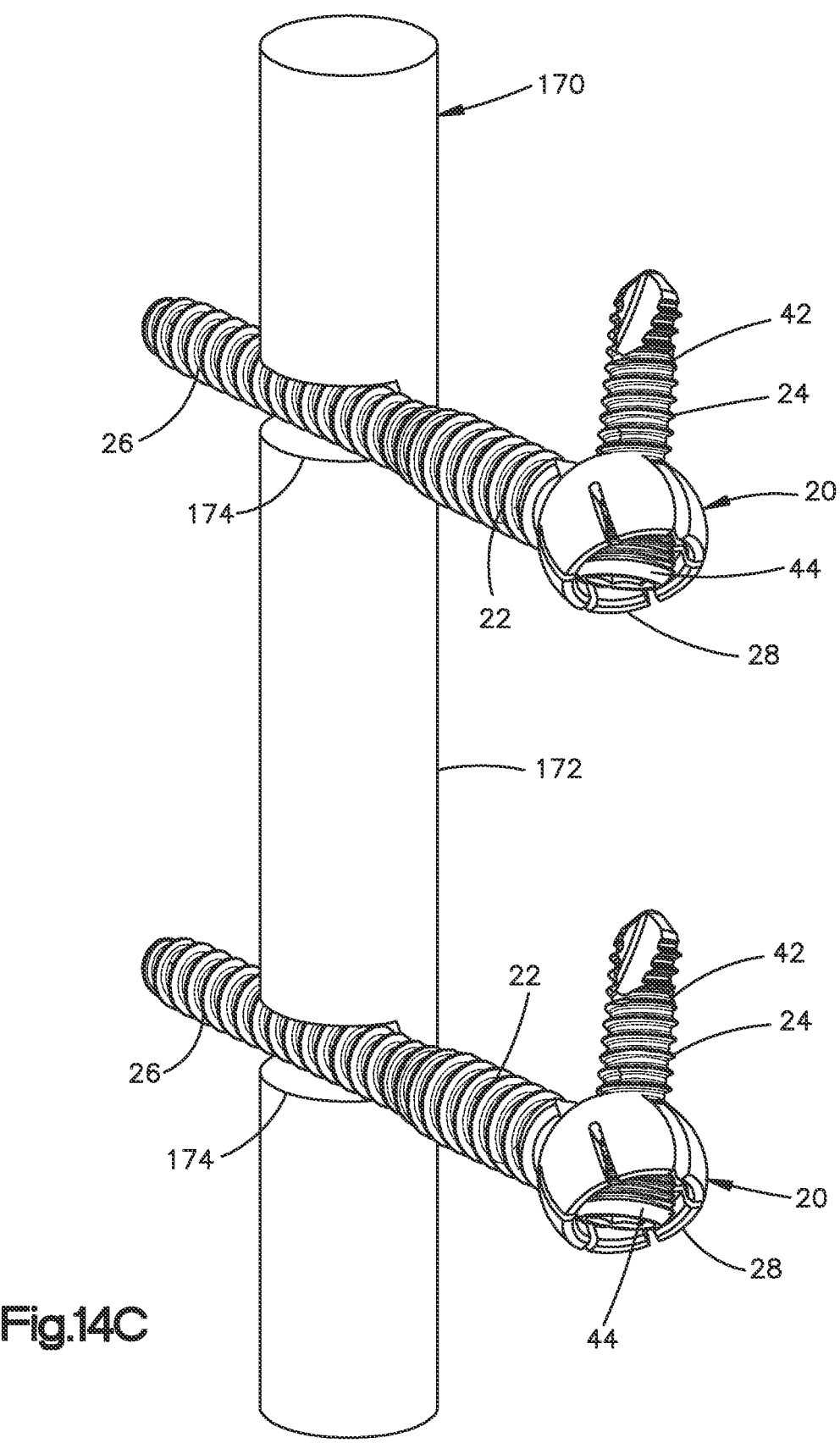
FIG. 14C is a side elevation view of an anchor fixation assembly including a plurality of anchor-in-anchor systems attached to an intramedullary in accordance with another alternative embodiment.

As illustrated in FIG. 14B, the anchor-in-anchor fixation assembly 23 can include a second auxiliary bone fixation device in the form of a bone plate 52. The bone plate can be constructed as desired, and includes a plate body 54 and a plurality of apertures 56 extending through the plate body 54 and configured to attach to the bone fixation system 20 in the manner described above. The bone plate 52 can be placed over the fracture that extends across the intramedullary rod such that the fracture is disposed between apertures 56 of the bone plate 52. For instance, the first bone anchor 22 is illustrated as attached to the intramedullary rod 170 in the manner described above with respect to the intramedullary rod 70. The head 128 of the anchor 122 includes retention tabs that are inserted into one of the apertures 56 of the bone plate 52 in the manner described above. Accordingly, the bone anchor 122 is attached to both the bone plate 52 and the intramedullary rod 70. The second bone anchor 124 can attach directly into the bone 21 without attaching to the intramedullary rod 170 in the manner described above.

It should be appreciated, alternatively, that the head 128 of the first bone anchor 122 can attach to the bone plate 52 in the manner described above, and the shaft 126 can attach to the bone 21 without passing through the intramedullary rod 170, and that the second bone anchor can pass through the head 128 and attach to one of the apertures 174 of the intramedullary rod 170. Alternatively or additionally, it should be appreciated that the bone fixation system 20 can be used in combination with the bone fixation system 120 or alone to attach the intramedullary rod 170 to the bone plate 52 and the surrounding bone in the manner described herein. It should further be appreciated that the intramedullary rod 70, or any intramedullary rod constructed as desired, can be attached to surrounding bone by one or both of the fixation systems 20 and 120 alone, or in combination with a second auxiliary bone fixation device such as a bone plate. The bone plates of the type described herein can be provided with any thickness as desired. For instance, the bone plates can be constructed sufficiently thin so as to provide an in-between member for suture attachment between a pair of bone anchors provided as screws, for instance, in order to fasten and reposition soft tissue structures such as tendons, ligaments, and muscles.

As illustrated in FIGS. 14A-B, it is appreciated that the apertures 174 can extend through the rod body 172 such that the apertures are defined on all sides by the rod body 172. Alternatively or additionally, referring to FIG. 14C, the apertures 174 can be provided as notches that extend into the rod body 172. As illustrated, the notches 174 are generally rectangular in cross-section and have a thickness substantially equal to the outer diameter of the bone anchor shaft that is inserted therein. The notches 174 extend laterally into the rod body 172 and terminate at a depth that is substantially equal to or slightly greater than the outer diameter of the bone anchor shaft 26 that is inserted therethrough. The notches 174 can thus provide a friction fit with the inserted shafts, or can be threaded so as to threadedly engage the inserted shafts.

Figure 15A:
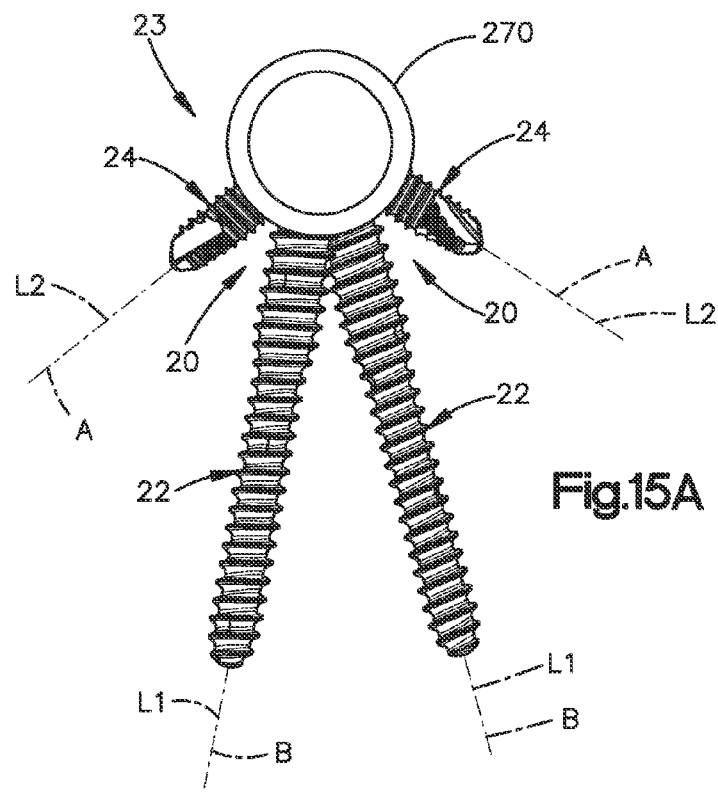
FIG. 15A is an end view of an anchor fixation assembly including a pair of anchor-in-anchor systems attached to a nail with one embodiment.
Figure 15B:
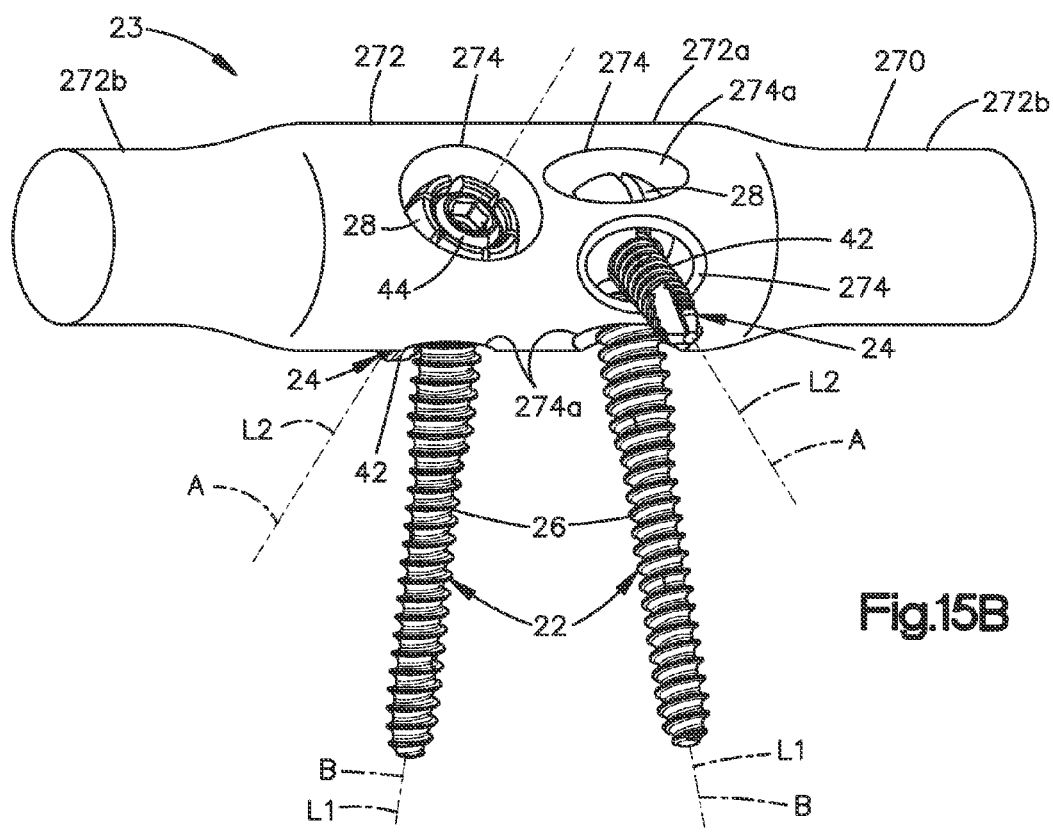
FIG. 15B is a side elevation view of the anchor fixation assembly illustrated in FIG. 15A.

Referring now to FIGS. 15A-B, the anchor-in-anchor fixation assembly 23 includes a nail 270 illustrated as including reference numerals corresponding to like elements of the intramedullary rod 70 incremented by 200. The nail 270 is configured for fixation to a pair of bone fragments separated, for instance, by a fracture of the distal radius. The nail 270 includes a tubular or alternatively shaped nail body 272 having a central portion 272a that has an outer diameter greater than the remaining region 272b of the nail body 272 that is disposed on both longitudinally outer sides of the central portion 272a. One or more longitudinally spaced apertures 274 extends into and through the central portion 272a of the nail body 272. Each aperture 274 is provided with an associated oblique aperture 274a that extends from the aperture 274 at a location inside the nail body 272 and through the outer surface of the nail body 272. The oblique aperture 274a extends along a central axis B that defines an angle with respect to the central axis A of the associated aperture 274 that is equal to the angle α defined between the shafts 26 and 42 of the bone anchors 22 and 24. Each aperture 274 can be provided with a pair of oblique apertures 274a so as to provide for fixation flexibility.

The fixation system 20 is installed into the nail 270 by first inserting the bone anchor 22 into the aperture 274 such that the shaft 26 extends into the proximal end of the aperture 274 and is then directed through the distal end of the associated auxiliary aperture 274a. The aperture 274 can define a diameter that is substantially equal to or slightly greater than the outer diameter of the anchor head 28, such that the anchor head is recessed within the aperture 274. It should be appreciated that any of the auxiliary fixation devices could include apertures configured such that the received bone anchor heads are recessed therein. Once the bone anchor 22 has been installed, the secondary bone anchor 24 is inserted into the bore 40 of the anchor head 22 in the manner described above, thereby causing the head 22 to expand and lock against the inner surface of the aperture 274. In particular, the shaft 42 extends into the proximal end of the aperture 274, through the anchor head 28, and through the distal end of the aperture 274. In this manner, the shaft 42 extends substantially normal to the underlying bone, while the shaft 26 extends oblique with respect to the underlying bone. The distal ends of the apertures 274 and auxiliary apertures 274a can be widened greater than the diameter of the respective shafts as desired, or can be provided as elongate slots so as to provide for angular flexibility.

Figure 16A:
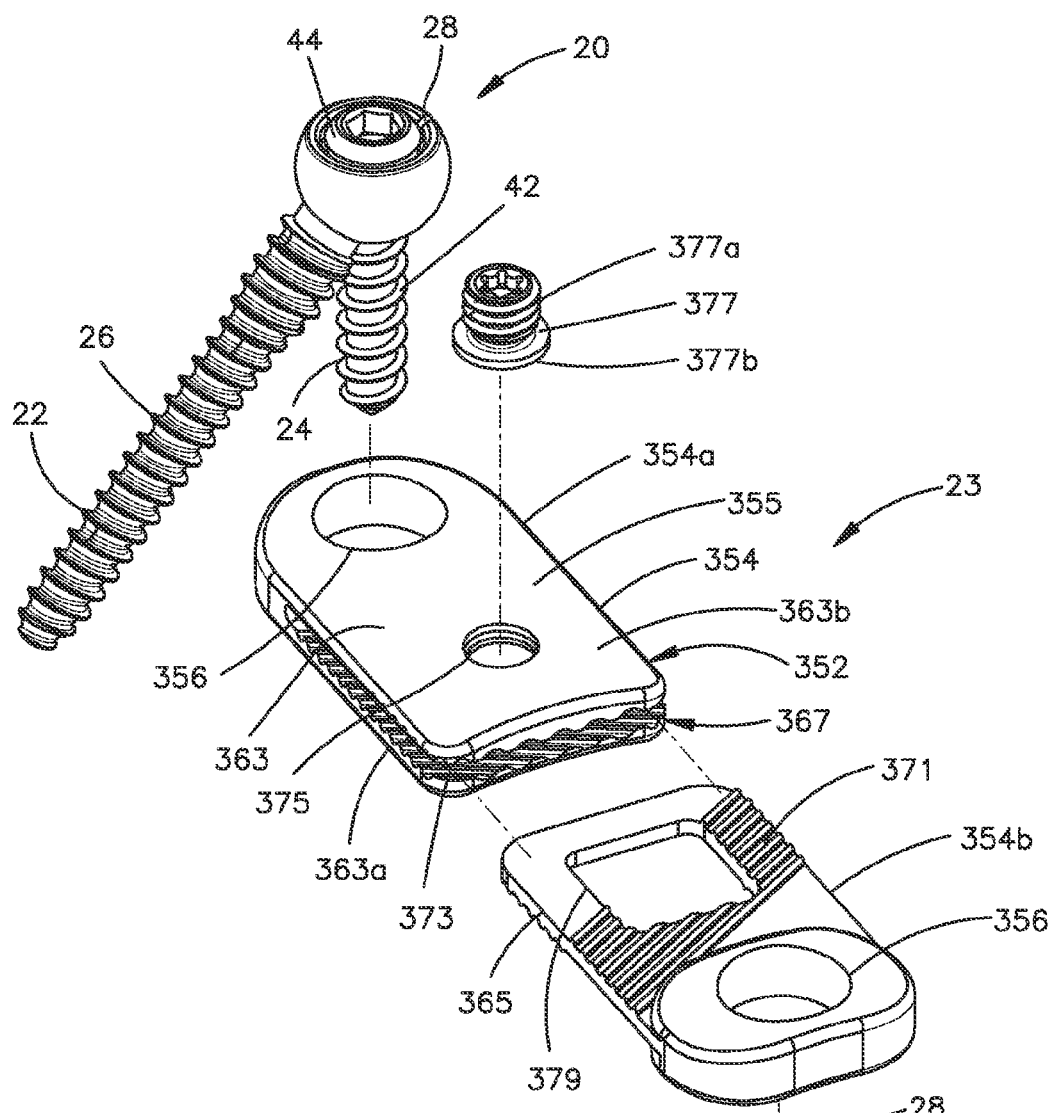
FIG. 16A is an exploded perspective view of an anchor-in-anchor fixation assembly including an expandable bone plate.
Figure 16B:
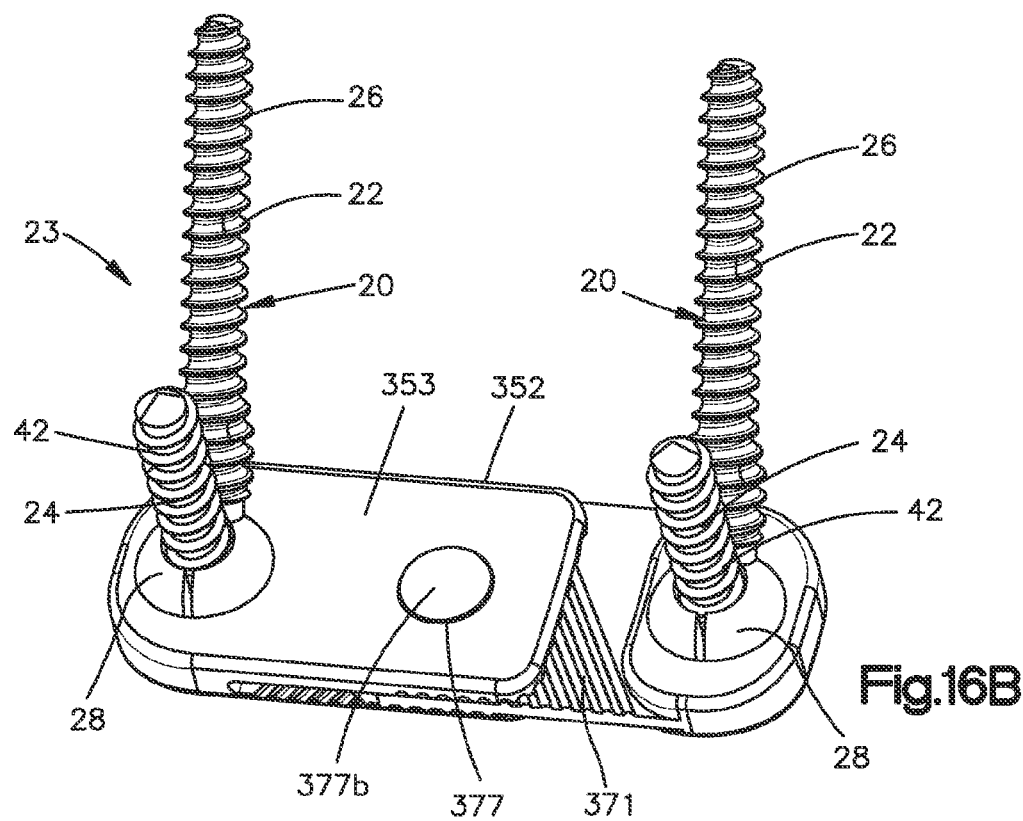
FIG. 16B is a bottom perspective view of the anchor-in-anchor fixation assembly illustrated in FIG. 16A.
Figure 16C:
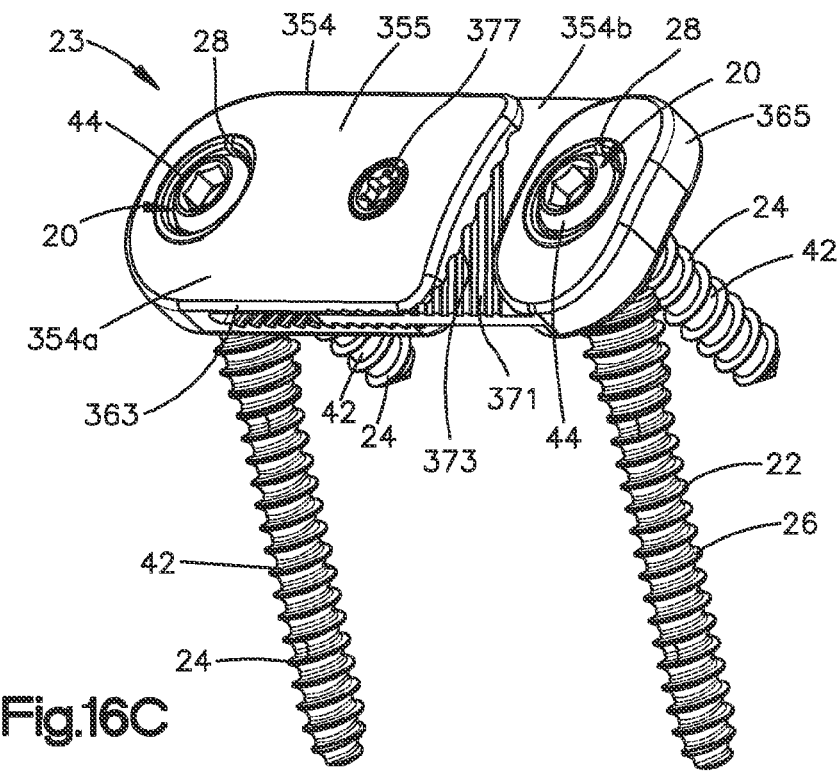
FIG. 16C is a top perspective view of the anchor-in-anchor fixation assembly illustrated in FIG. 16A.
Figure 17A:
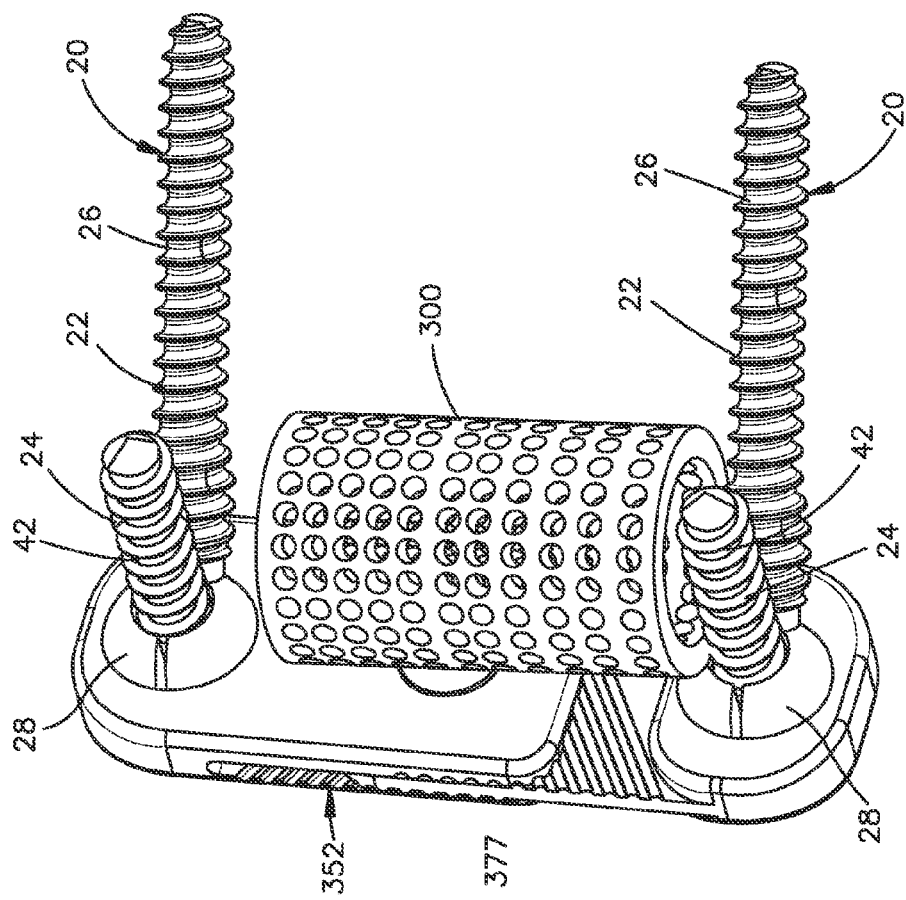
FIG. 17A is a top perspective view of the anchor-in-anchor fixation assembly illustrated in FIGS. 16A-C further including an intervertebral implant.
Figure 17B:
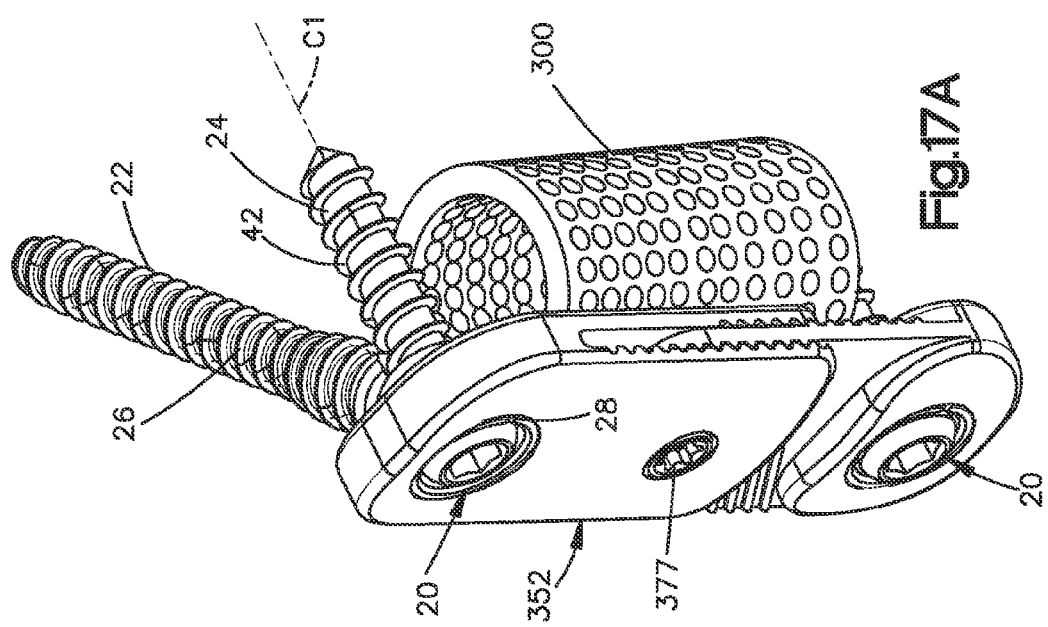
FIG. 17B is a bottom perspective view of the anchor-in-anchor fixation assembly illustrated in FIG. 17A.
Figure 17C:
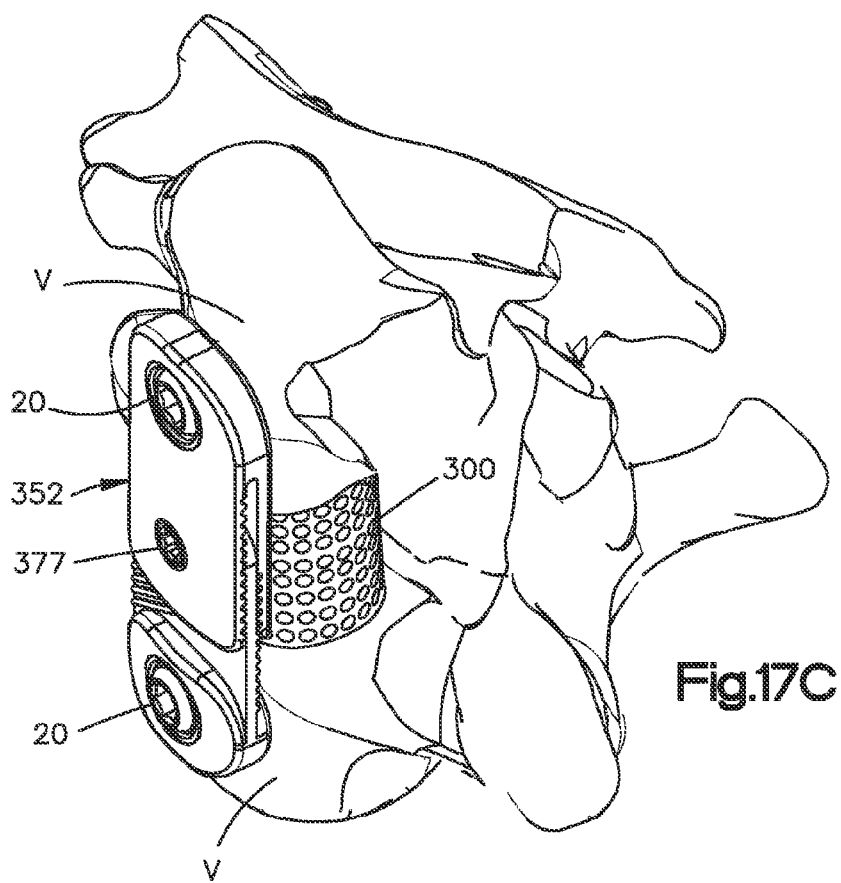
FIG. 17C is a perspective view of the anchor-in-anchor fixation assembly illustrated in FIG. 17B implanted in a spine.
Figure 17D:
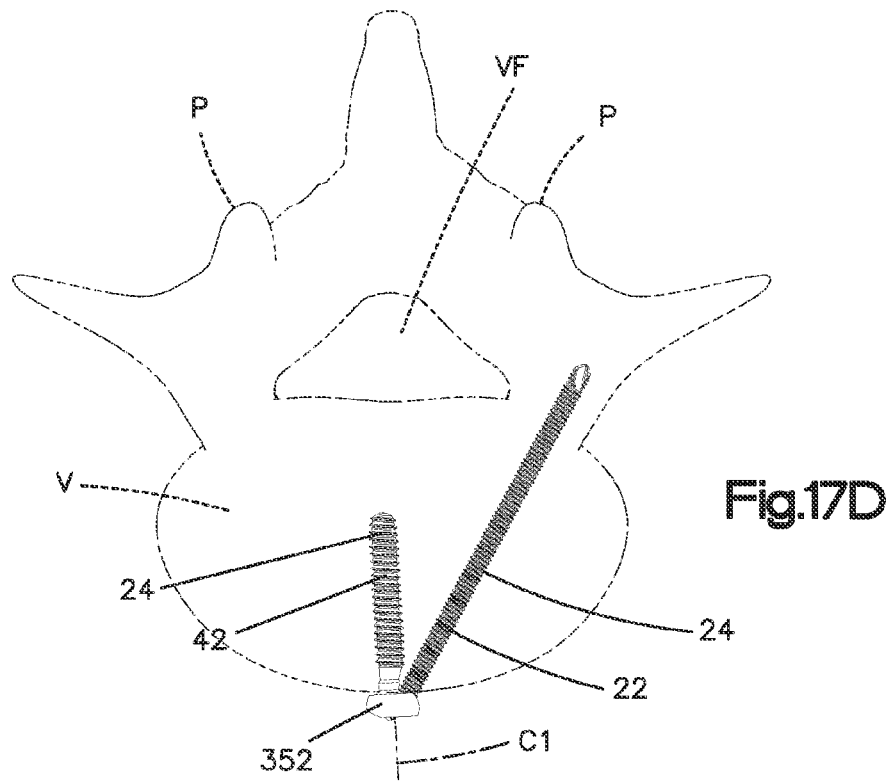
FIG. 17D is a schematic top view of the anchor-in-anchor fixation assembly as illustrated in FIG. 17C.

Referring now to FIGS. 16A-C generally, while anchor-in-anchor bone fixation systems have been illustrated and described in accordance with various fixation procedures, it is recognized that the fixation systems can also be implemented for spinal fixation, for instance in cervical and/or lumbar posterior facet screw fixation for management of instabilities resulting from, for example, a fracture, a degenerative disorder, a tumor, or the like.

Referring now to FIGS. 16A-C, the anchor-in-anchor fixation assembly 23 of the type described herein can include an auxiliary fixation device provided as an expandable bone plate 352 and a pair of fixation systems, illustrated as fixation systems 20. The bone plate 352 is illustrated whereby reference numerals corresponding to like elements of bone plate 352 are incremented by 100. Thus, the bone plate 352 includes a bone plate body 354 defining a bone-facing surface 353 and an opposing surface 355, and a pair of apertures 356 extending through the plate body 354.

The bone plate body includes a pair of body segments 363 and 365. The body segment 363 includes an inner segment plate 263a and an outer segment plate 363b, and an interior groove 367 disposed between the plates 363a-b that is sized to receive the body segment 365 therein. At least one or both inner surfaces 369 that define the groove 367 include teeth 373 extending out therefrom into the groove 367. Likewise, one or both of the surfaces of the body segment 365 define teeth 371 extending outwardly therefrom and configured to engage the teeth 373. The first body segment 363 defines a threaded locking aperture 375 that is threaded at the outer plate 363b. Accordingly, the shaft 377a of a threaded locking pin 377 can be inserted through the aperture 375 in a direction from the inner surface 353 toward the outer surface 355, and engage the threads of the outer plate 363b so that the head 377b can compress the plates 363a-b against each other, thereby causing the teeth 371 and 373 to engage and prevent relative movement between the body segments 363 and 365.

During operation, the body segment 365 is inserted into the groove 367, and extended or retracted so that the apertures 356 define a desired length therebetween. The second body segment 365 includes a cutout 379 that allows the segment 365 to slide without interfering with the locking pin 377. The locking pin 377 is then rotated within the aperture 375 to advance within the aperture 375 and lock the position of the body segments 365 and 367. In this regard, it should be appreciated that a bone fixation system 20 can be locked within the apertures 356, such that the shafts 26 and 42 of the bone anchors 22 and 24 are inserted into underlying bone in the manner described above. It should be appreciated that once the fixation systems 20 have been attached to the plate 352 and to the underlying bone, the body segment 365 can be retracted within the groove 367 so as to reduce the underlying fracture, or otherwise compress a pair of bones or bone fragments joined to the fixation systems 20 toward each other. Alternatively, the body segment 365 can be extended within the groove so as to further space the bones or bone fragments joined to the fixation systems 20.

The plate 352 can thus be attached to a fractured long bone in the manner described above, or can be used in combination with a corpectomy, whereby a vertebral body is replaced by a vertebral implant. For instance, referring now to FIGS. 17A-D, the fixation assembly 23 includes the fixation systems 20 and the auxiliary fixation device in the form of the bone plate 352 along with a second fixation member in the form of a vertebral implant 300. The implant 300 is illustrated as an annular mesh cage, though it should be appreciated that any vertebral implant could be incorporated. As illustrated, the implant 300 is disposed between the fixation systems, and is thus configured to be inserted into an intervertebral space, for instance, after a vertebral body has been removed.

Once the implant 300 is disposed within the intervertebral space, the fixation systems 20 are affixed to the adjacent vertebral bodies V, for instance in the cervical spine region, via an anterior approach. In particular, both bone anchors 22 and 24 extend into the vertebral body, such that one of the bone anchors extends through the respective vertebral body V and into one of the pedicles P. In accordance with the illustrated embodiment, the shafts 26 of the first bone anchors 22 are inserted through the corresponding vertebral body V and into a target one of the pedicles P. Once each shaft 26 has reached its approximate desired depth in the pedicle P, it is rotated until the central axis C1 is aligned with the vertebral body V at the desired angle of entry. Next, the bone fixation plate 352 is attached to the heads 28 in the manner described above with respect to plate 52. For instance, the apertures 356 are fitted over the heads 28 until the heads 28 are disposed within the apertures 356. Finally, the shafts 42 of the second bone anchors 24 are inserted into respective heads 28 and into the corresponding vertebral bodies V. The shafts 42 have a length sufficient so as to not extend into the vertebral foramen VF.

If desired, the plate 352 can be extended or compressed in the manner described above if it is desired to adjust the spacing between the adjacent vertebral bodies that define the intervertebral space in which the implant 300 is disposed. In this regard, it should be appreciated that the fixation system 23 allows all bone anchors to be inserted into the vertebral bodies V via an anterior approach, and that the angular offset of the bone anchors 22 and 24 define a triangular load bearing plane in the manner described above, and are thus better able to withstand higher forces and prevent subsidence or migration of the bone anchors within vertebral bodies without requiring additional spinal fixation via a posterior approach. The bone anchors 22 can be inserted into vertically aligned pedicles P as illustrated, or can be inserted into pedicles P disposed on opposing sides of the vertebral foramen VF depending on the angular orientation of the central axis C1 of the first bone anchors 22. Alternatively still, a pair of side-by-side apertures could be disposed at opposing longitudinal ends of the bone plate 252, such that a pair of fixation assemblies 20 includes a corresponding pair of bone anchors 24 that extend into both pedicles of the respective vertebra.

Figure 18:
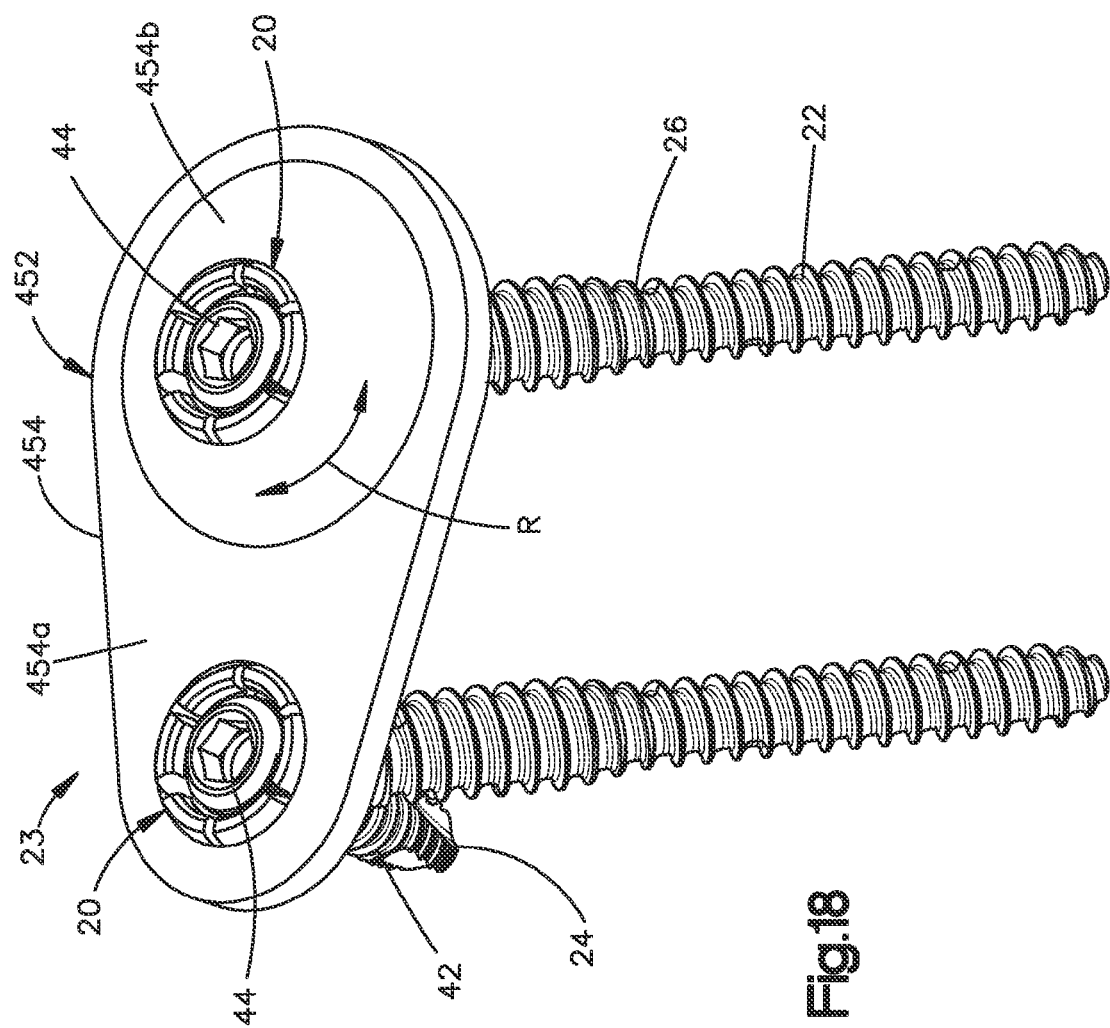
FIG. 18 is a perspective view of an anchor-in-anchor fixation assembly including an eccentric bone plate.

Referring now to FIG. 18, a bone plate 452 constructed in accordance with an another alternative embodiment is illustrated as including reference numerals corresponding to like structure of bone plate 52 incremented by 400. Thus, the bone plate 452 includes a plate body 454. The plate body 454 includes a first segment 454a and a second segment 454b that is cylindrical and thus rotatable within the first segment 454a. One of the apertures 456 extends through the second segment 454b at a location off-center with respect to the axis of rotation of the second segment 454b. Otherwise stated, the aperture 456 extending through the second segment 454b is eccentrically positioned, such that the longitudinal position of the bone anchors 22 and 24 mounted in the eccentric aperture 456 is adjustable.

For instance, a first fixation system such as system 20 is affixed within the aperture 456 extending through the first segment 454a in the manner described above, such that the shaft 26 of the first bone anchor 22 extends in a direction oblique with respect to the bone plate 452, and the shaft 42 of the second bone anchor 24 extends substantially normal with respect to the plate 452, though it should be appreciated that both shafts 26 and 42 could alternatively extend in a direction oblique with respect to the bone plate 452. A second fixation system such as system 20 is likewise affixed within the aperture 456 that extends through the second segment 454b in the manner described above. Thus, the respective shaft 24 extends in a direction oblique with respect to the bone plate 452 and the shaft 42 extends substantially normal with respect to the bone plate 452, though both shafts 26 and 42 could extend oblique with respect to the plate 452. Before or after the fixation assemblies 20 are affixed to the apertures 456, the second segment 454b can be rotated in the direction of Arrow R within the first segment 454a so as to adjust the longitudinal position of the respective shafts 26 and 42 with respect to the shafts 26 and 42 joined to the aperture 456 extending through the first segment 454a, thereby increasing or decreasing the longitudinal distance between the fixation assemblies 20.

While the fixation system 20 is illustrated as coupled to the plate 452, it should be appreciated that, as with all auxiliary fixation devices described herein, the other fixation system, in this case the second fixation system 120, could alternatively or additionally be coupled to the plate 452.

Figure 19A:
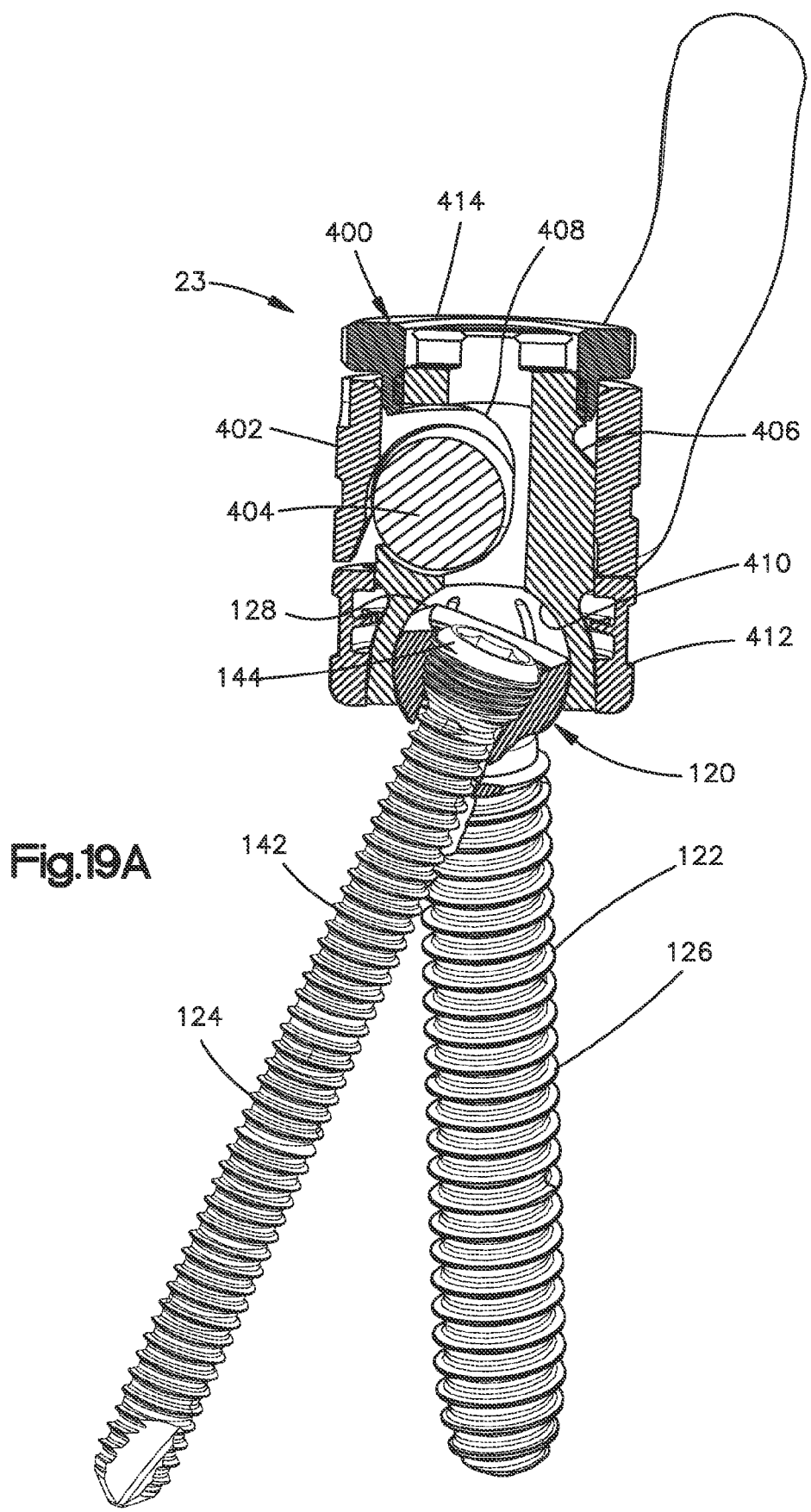
FIG. 19A is a sectional side elevation view of an anchor-in-anchor fixation assembly including a pedicle screw assembly.
Figure 19B:
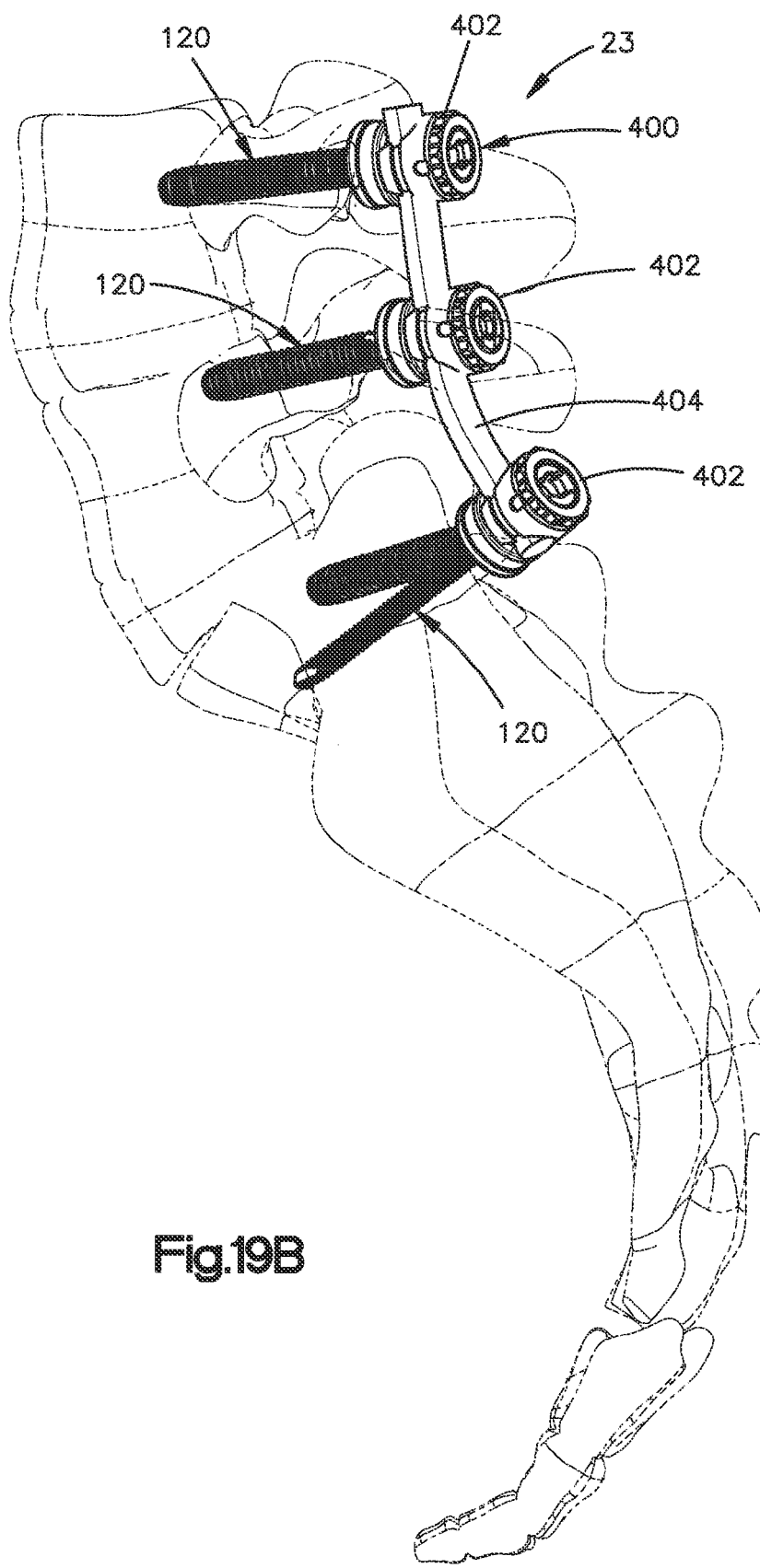
FIG. 19B is a perspective view of the anchor-in-anchor fixation assembly illustrated in FIG. 19A implanted into a spine.
Figure 19C:
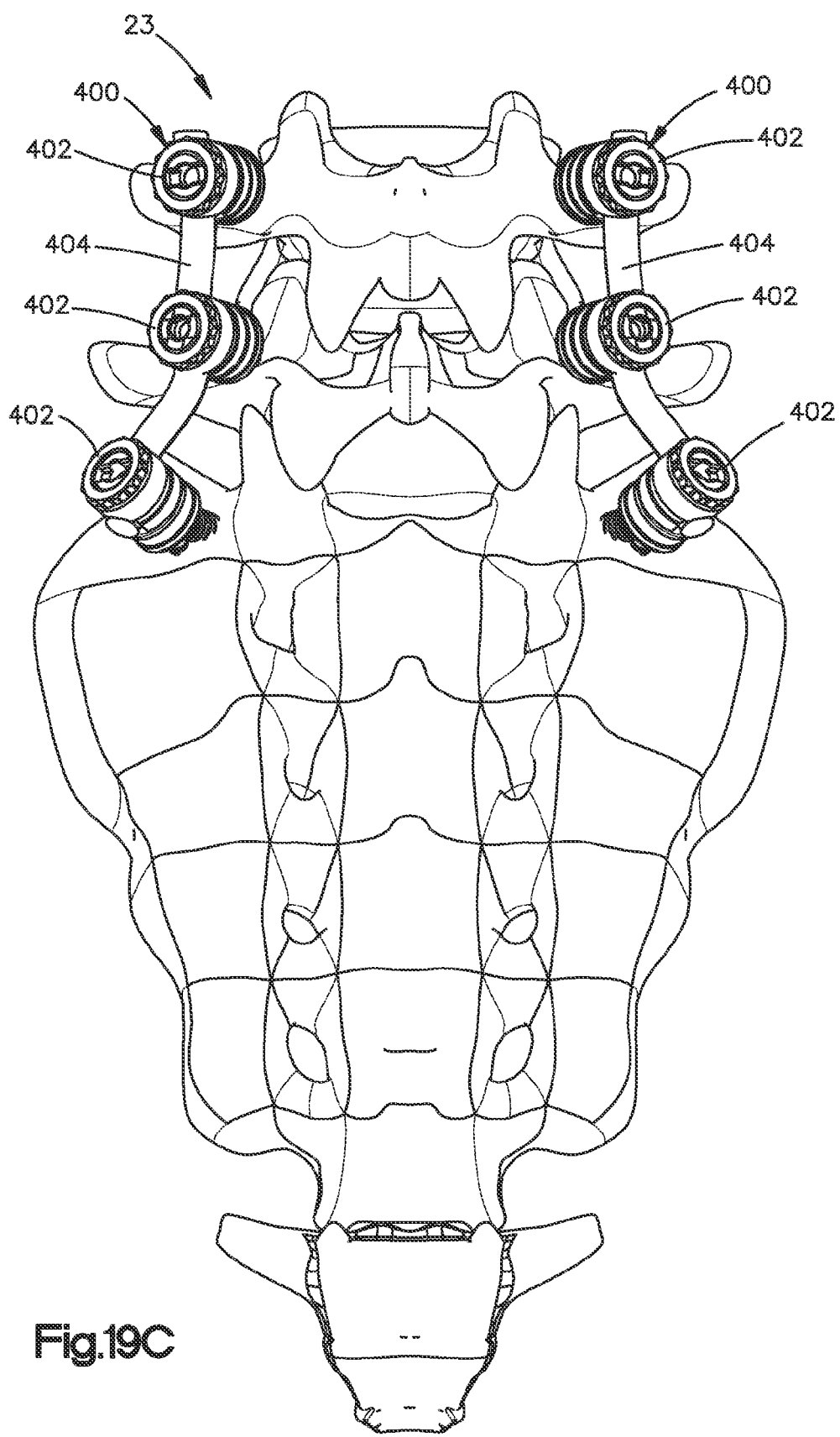
FIG. 19C is a side elevation view of the anchor-in-anchor fixation assembly illustrated in FIG. 19A implanted into a spine.

Referring now to FIGS. 19A-C, it should be appreciated that the anchor-in-anchor fixation assembly 23 can include a plurality of bone fixation systems such as bone fixation systems 120 in combination with an auxiliary fixation device provided as a pedicle screw assembly 400. The pedicle screw assembly 400 includes a plurality of pedicle screws 402 attached via a fixation rod 404. Each pedicle screw 402 includes an internal opening 408 configured to receive the fixation rod 404, and a lower opening 410 configured to receive the head 128 of the first bone anchor 122. In accordance with the illustrated embodiment, an anchor body 406 defines both the internal opening 408 and the lower opening 410. A collet 412 surrounds the anchor body 406 so as to provide compression against the lower opening 410, and a cap 414 is threadedly inserted into the upper end of the anchor body 406 so as to provide compression to the internal opening 408, and locking the fixation rod 404 in the pedicle screw 402.

During operation, the shaft 126 of the first bone anchor 122 is inserted into the underlying sacral spine area and into a vertebral body through the pedicle, or could alternatively be inserted into a facet, lamina, the spinous process, or alternative vertebral structure as desired, so as to affix the first bone anchor 122 at a location offset with respect to the pedicle. The bone anchor 122 is rotated until the central axis C1 is aligned with the pedicle. Next, the shaft 142 of the second bone anchor 124 is inserted through the head 128 and inserted into the pedicle until the head 144 is disposed in the head 128 in the manner described above. The lower opening 410 is then fitted over the head 128 so as to operatively couple the fixation system 120 to the fixation rod 404. The angular offset of the shafts 126 and 142 define a triangular load bearing plane in the manner described above, and are thus better able to withstand higher forces and prevent subsidence or migration of the pedicle screw 140 within the vertebral body. As illustrated in FIG. 19C, the fixation assembly 23 includes a pair of pedicle screw assemblies 400 mounted onto both opposing pedicles of the fused vertebral bodies, which can be disposed in any spinal region as desired.

Figure 20C:
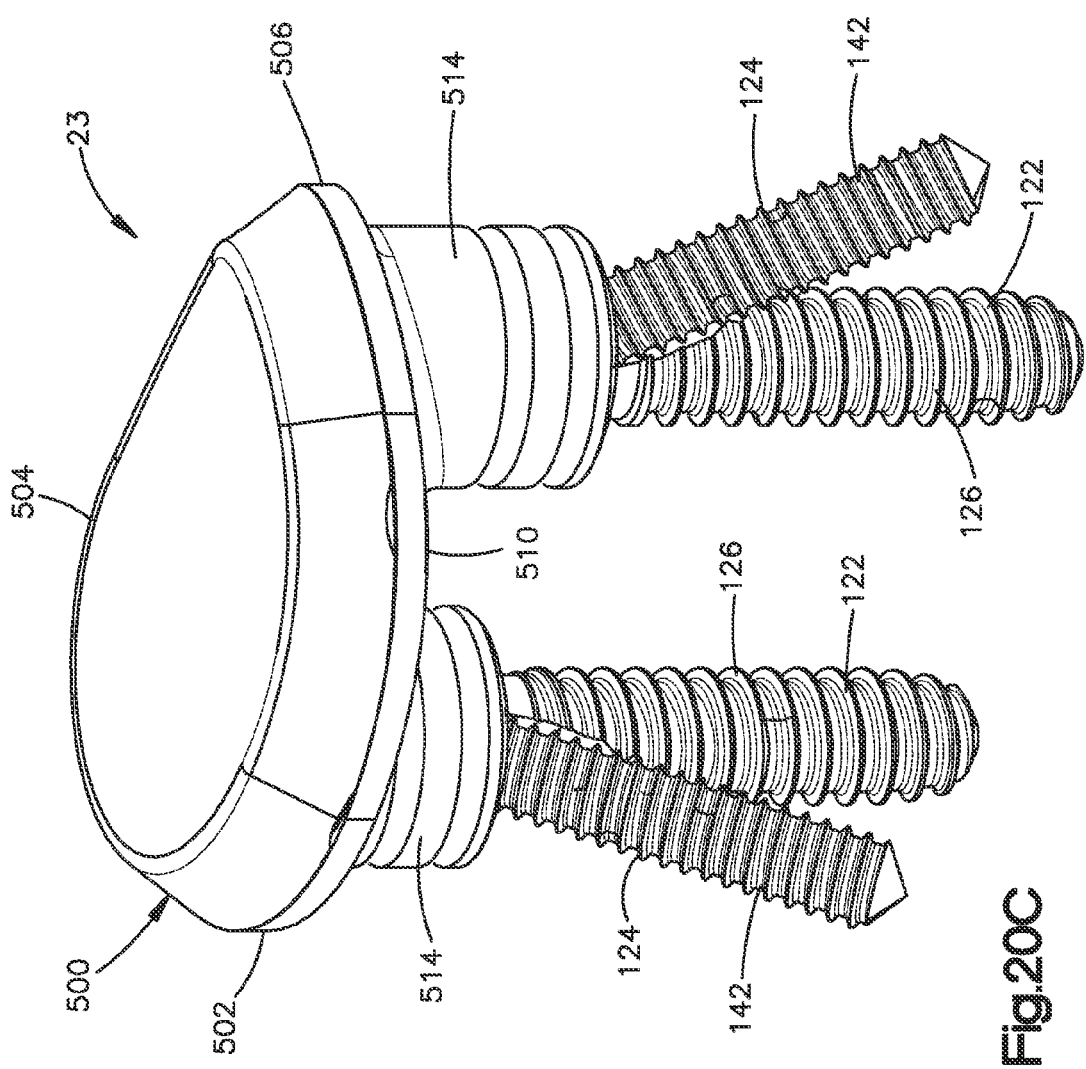
FIG. 20C is a perspective view of the assembled anchor fixation assembly illustrated in FIG. 20A.

Referring now to FIGS. 20A-C, the anchor-in-anchor fixation assembly 23 includes first and second bone anchor-in-anchor fixation systems such as systems 120 coupled to an auxiliary fixation device provided as an implant, such as a shoulder prosthesis 500 configured to mate with a humeral implant. The prosthetic 500 includes a backing plate 502 that is coupled to an insert 504. The backing plate can be made from an implant-grade metal such as titanium, while the insert 504 can be made from poly-ethylene.

The backing plate 502 defines a backing plate body 506 that presents a concave insert-engaging surface 508 and an opposing convex surface 510. A pair of spaced apertures 512 extends through the body 506 along respective central axes A. A pair of cylindrical extensions 514 projects down from the opposing surface 510 at a location aligned with the apertures 512, and each define aperture extensions 512a. A radial projection 516 extends inward from the inner surface of each cylindrical extension, and assists in affixing the insert 504 to the backing plate 502. A lip 518 projects radially inward from the distal end of each cylindrical extension 514, and presents a mounting surface for the respective fixation systems 120.

The fixation systems 120 are attached to the backing plate 502 and to underlying bone by first inserting the shaft 126 of the first bone anchor 122 into underlying scapular bone in the manner described above. Next, the shaft 142 of the second bone anchor 124 is inserted through the head 128 and into the underlying scapular bone such that the head 144 is disposed inside the head 128 in the manner described above. Next, the backing plate 502 is placed down over the head 128 such that the lips 518 snap over the respective heads 128 and lock the heads 128 therein. The shafts 126 can be aligned with the axis A of the aperture 512, and the shafts 142 can be angulated with respect to the axis A, though it should be appreciated that both shafts 126 and 142 could be angulated with respect to the axis A.

The insert 504 defines a bearing surface 520 that is concave so as to provide an artificial or prosthetic glenoid, and an opposing surface 522. A pair of locking pegs 524 project down from the opposing surface 522 at locations aligned with the apertures 512. The pegs 524 define a circumferential recess 526 that receive the projections radial projections 516 to attach the insert 504 to the backing plate 504, at which point the artificial glenoid 520 provides an articulation surface for a humeral implant.

While the concavity of the bearing surface 520 is suitable to provide an artificial or prosthetic glenoid as described above, it should be appreciated that the bearing surface 520 can be provided with any curvature as desired. For instance, the concavity of the bearing surface 520 can be constructed so as to provide a hip cup usable as a ball-and-socket joint, usable for instance in hiparthroplasty.

It should be appreciated that a kit can be provided that includes one or more bone fixation assemblies 23 or components thereof as described above. The components of the kit can be configured the same or differently. For instance, bone anchors 22 and 24 can be provided having different lengths and outer diameters of the shafts 42 and 26, differently constructed shafts and threads depending on the needs of the surgeon and the surgical procedure being performed, and different angles α defined between the shafts and heads. The kit can further include one or more auxiliary fixation devices of the type described above.

Although the invention has been described with reference to preferred embodiments or preferred methods, it is understood that the words which have been used herein are words of description and illustration, rather than words of limitation. For instance, it should be appreciated that the structures and features of the various bone fixation assemblies and systems described herein and their components can be incorporated into any of the other bone fixation assemblies and systems described herein and their components, unless otherwise indicated. Furthermore, although the invention has been described herein with reference to particular structure, methods, and embodiments, the invention is not intended to be limited to the particulars disclosed herein, as the invention extends to all structures, methods and uses that are within the scope of the present invention, along with kits having one or more fixation systems, assemblies, or components thereof as described herein. Those skilled in the relevant art, having the benefit of the teachings of this specification, may effect numerous modifications to the invention as described herein, and changes may be made without departing from the scope and spirit of the invention, for instance as recited in the appended claims.

What is claimed:

1. An anchor-in-anchor fixation assembly comprising:
at least one anchor-in-anchor system including:
a first bone anchor including a first shaft and a first head, the first shaft extending along a first longitudinal shaft axis, and the first head defining a bore extending therethrough along a bore axis, wherein the bore axis and the first longitudinal shaft axis define an angle; and
a second bone anchor including a second shaft and a second head, the second shaft extending along a second longitudinal shaft axis and configured to attach to underlying structure, the second bone anchor configured to be inserted into the bore; and
an intramedullary nail configured to be inserted into a bone canal, the intramedullary nail including a body, the intramedullary nail defining a plurality of apertures that extend through the body, wherein one of the apertures receives at least a portion of the first bone anchor when the intramedullary nail is disposed in the bone canal and the anchor-in-anchor system is coupled to the intramedullary nail.

2. The anchor-in-anchor fixation assembly as recited in claim 1, wherein the first head defines a curved outer surface, and the plurality of apertures define an inner curved surface that mates with the curved outer surface of the first head.

3. The anchor-in-anchor fixation assembly as recited in claim 2, wherein one of the plurality of apertures is eccentrically located on the body.

4. The anchor-in-anchor fixation assembly as recited in claim 2, wherein the second head is configured to be disposed within the bore, and the second head causes the first head to expand against the inner curved surface of the bore.

5. The anchor-in-anchor fixation assembly as recited in claim 2, wherein the bore includes a plurality of threads configured to engage corresponding threads extending out form the second head.

6. The anchor-in-anchor fixation assembly as recited in claim 2, wherein the first head is expandable.

7. The anchor-in-anchor fixation assembly as recited in claim 6, wherein the first head defines at least one slot that defines a pair of expendable retention tabs.

8. The anchor-in-anchor fixation assembly as recited in claim 7, wherein the slot extends entirely through the first head.

9. The anchor-in-anchor fixation assembly as recited in claim 7, wherein a plurality of slots extend partially through the first head.

10. The anchor-in-anchor fixation assembly as recited in claim 1, wherein the first head defines a first head axis that defines an acute angle with respect to the first longitudinal axis.

11. The anchor-in-anchor fixation assembly as recited in claim 1, wherein the first head defines a first head axis that is substantially parallel with the first longitudinal axis.

12. The anchor-in-anchor fixation assembly as recited in claim 1, wherein the first head defines a first head axis that is substantially parallel with the bore axis.

13. The anchor-in-anchor fixation assembly as recited in claim 1, wherein the first head defines a first head axis that defines an acute angle with respect to the bore axis.

14. The anchor-in-anchor fixation assembly as recited in claim 1, wherein the underlying structure comprises bone.

15. The anchor-in-anchor fixation assembly as recited in claim 1, wherein the intramedullary nail is configured to fix a distal radius fracture.

16. The anchor-in-anchor fixation assembly as recited in claim 1, wherein the second bone anchor is configured to be inserted into the bore such that the second longitudinal shaft axis is substantially coincident with the bore axis.

17. The anchor-in-anchor fixation assembly as recited in claim 1, wherein the body includes a first segment that defines a first aperture, and a second segment that defines a head of the body and further defines a second aperture.

18. The anchor-in-anchor fixation assembly as recited in claim 17, wherein the second segment defines an outer diameter greater than that of the first segment.

19. The anchor-in-anchor fixation assembly as recited in claim 17, wherein the second aperture is configured to receive the first bone anchor.

20. The anchor-in-anchor fixation assembly as recited in claim 19, wherein the second bone anchor is configured to be attached directly to bone that surrounds the intramedullary nail without also attaching to the intramedullary nail.

21. The anchor-in-anchor fixation assembly as recited in claim 17, wherein the intramedullary nail is configured such that a fracture of the bone is disposed between the first aperture and second aperture when the intramedullary nail is inserted into the canal.

22. The anchor-in-anchor fixation assembly as recited in claim 17, further comprising a plurality of the anchor-in-anchor systems, wherein the second segment further defines a plurality of second apertures each configured to receive a first bone anchor of a respective one of the plurality of anchor-in-anchor systems.

23. The anchor-in-anchor fixation assembly as recited in claim 22, wherein the second apertures are angularly displaced from each other.

24. The anchor-in-anchor fixation assembly as recited in claim 1, wherein the first and second bone anchors are not joined by any additional auxiliary fixation device.

25. The anchor-in-anchor fixation assembly as recited in claim 1, further comprising an additional auxiliary fixation device that is configured to be attached to the anchor-in-anchor system.

26. The anchor-in-anchor fixation assembly as recited in claim 25, wherein the additional auxiliary fixation device comprises a bone plate.

27. The anchor-in-anchor fixation assembly as recited in claim 1, wherein the angle is acute.

* * * * *